(12) United States Patent
Cheung et al.

(10) Patent No.: US 7,141,569 B2
(45) Date of Patent: *Nov. 28, 2006

(54) ANTIVIRAL PYRAZOLOPYRIDINE COMPOUNDS

(75) Inventors: Mui Cheung, Durham, NC (US); Kristjan Gudmundsson, Durham, NC (US); Brian A. Johns, Durham, NC (US)

(73) Assignee: SmithKline Beecham Corporation, Philadelphia, PA (US)

( * ) Notice: Subject to any disclaimer, the term of this patent is extended or adjusted under 35 U.S.C. 154(b) by 314 days.

This patent is subject to a terminal disclaimer.

(21) Appl. No.: 10/473,491

(22) PCT Filed: Mar. 21, 2002

(86) PCT No.: PCT/US02/08793

§ 371 (c)(1),
(2), (4) Date: Sep. 25, 2003

(87) PCT Pub. No.: WO02/083672

PCT Pub. Date: Oct. 24, 2002

(65) Prior Publication Data

US 2004/0167335 A1 Aug. 26, 2004

Related U.S. Application Data

(60) Provisional application No. 60/282,749, filed on Apr. 10, 2001.

(51) Int. Cl.
*C07D 471/04* (2006.01)
*A61K 31/435* (2006.01)
*C07D 401/04* (2006.01)

(52) U.S. Cl. ............ 514/235.8; 514/252.18; 514/274; 514/275; 544/122; 544/315; 544/331

(58) Field of Classification Search ........... 544/122, 544/316, 331; 514/235.8, 274, 252.18, 275
See application file for complete search history.

(56) References Cited

U.S. PATENT DOCUMENTS

| | | | |
|---|---|---|---|
| 4,576,952 A | 3/1986 | Hurst et al. | |
| 4,621,089 A | 11/1986 | Ward et al. | |
| 4,670,432 A | 6/1987 | Ward et al. | |
| 4,985,444 A | 1/1991 | Shiokawa et al. | |
| 5,155,114 A | 10/1992 | Shiokawa et al. | |
| 5,204,346 A | 4/1993 | Shiokawa et al. | |
| 5,234,930 A | 8/1993 | Shiokawa | |
| 5,296,490 A | 3/1994 | Shiokawa et al. | |
| 5,300,478 A | 4/1994 | Michaely et al. | |
| 5,498,774 A | 3/1996 | Mitsudera et al. | |
| 5,552,422 A | 9/1996 | Gauthier et al. | |
| 5,700,816 A | 12/1997 | Isakson et al. | |
| 5,773,530 A | 6/1998 | Akahane et al. | |
| 5,990,148 A | 11/1999 | Isakson et al. | |
| 6,136,839 A | 10/2000 | Isakson et al. | |
| 6,207,675 B1 | 3/2001 | Carry et al. | |
| 6,919,352 B1 | 7/2005 | Chamberlain et al. | |
| 6,962,914 B1 | 11/2005 | Gudmundsson et al. | |
| 2004/0053942 A1 | 3/2004 | Alberti et al. | |

FOREIGN PATENT DOCUMENTS

| | | |
|---|---|---|
| EP | 0 364 204 A1 | 10/1989 |
| EP | 0 404 190 A1 | 6/1990 |
| EP | 0 404 190 B1 | 6/1990 |
| EP | 0 379 979 | 8/1990 |
| EP | 0 467 248 B1 | 7/1991 |
| EP | 0 497 258 A2 | 1/1992 |
| FR | 2 757 059 | 6/1998 |
| WO | WO 91 00092 | 1/1991 |
| WO | WO 91 19497 | 12/1991 |
| WO | WO 95 00501 | 1/1995 |
| WO | WO 96 06840 | 3/1996 |
| WO | WO 96 21667 | 7/1996 |
| WO | WO 96 31509 | 10/1996 |
| WO | WO 96 41625 | 12/1996 |
| WO | WO 96 41626 | 12/1996 |
| WO | WO 96 41645 | 12/1996 |
| WO | WO 98 56377 | 12/1998 |
| WO | WO 99 12930 | 3/1999 |
| WO | WO 99/58523 | 11/1999 |
| WO | WO 99/59585 | 11/1999 |

(Continued)

OTHER PUBLICATIONS

Bosseray et al., PubMed Abstract (Pathol Biol (Paris) 50(8):483-92), Oct. 2002.*

(Continued)

*Primary Examiner*—Deepak Rao
(74) *Attorney, Agent, or Firm*—Lorie Ann Morgan

(57) ABSTRACT

The present invention provides compounds of formula (I):

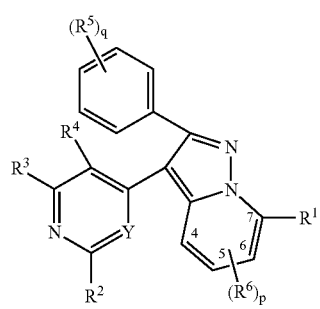

pharmaceutical compositions containing the same, processes for preparing the same and their use as pharmaceutical agents.

25 Claims, No Drawings

FOREIGN PATENT DOCUMENTS

| | | |
|---|---|---|
| WO | WO 99 64419 | 12/1999 |
| WO | WO 00/26216 | 5/2000 |
| WO | WO 00/52008 | 9/2000 |
| WO | WO 01/00615 | 1/2001 |
| WO | WO 01 14375 | 3/2001 |
| WO | WO 02/16359 | 2/2002 |
| WO | WO 02 16359 | 2/2002 |
| WO | WO 02 18382 | 3/2002 |
| WO | WO 02/18382 | 3/2002 |
| WO | WO 02 48147 | 6/2002 |
| WO | WO 02/048148 | 6/2002 |
| WO | WO 02 066481 | 8/2002 |
| WO | WO 02/066481 | 8/2002 |
| WO | WO 03/00682 | 1/2003 |

OTHER PUBLICATIONS

Razonable et al., PubMed Abstract (Herpes 10(3):60-5), Dec. 2003.*

Vippagunta et al., Crystalline Solids, Advanced Drug Delivery Reviews 48:3-26, 2001.*

West, Solid Solutions, Solid State Chemistry and Its Applications, pp. 365, 1988.*

Douglas, Jr. Introduction to Viral Diseases, Cecil Textbook of Medicine, 20th Edition, vol. 2, pp. 1739-1747, 1996.*

Vane, J. et al. "Towards a Better Aspirin." Nature, vol. 367, Jan. 20, 1994, pp. 215-216.

Carter, J. et al. "Recently Reported Inhibitors of Cyclooxygenase-2." Exp. Opin. Ther. Patents (1998), 8(1), pp. 21-29.

Talley, JJ., "Review Pulmonary-Allergy, Dermatological, Gastrointestinal & Arthritis, Selective Inhibitors of Cyclooxygenase-2." Exp. Opin. Ther. Patents (1997) 7(1), pp. 55-62.

Roy, P., "A New Series of Selective Cox-2 Inhibitors: 5,6-Diarylthiazolo [3,2-b][1,22,4] Triazoles," *Bioorganiz & Med. Chem. Ltrs.*, vol. 7, No. 1, 1997, pp. 57-62.

Therien, Michael, Synthesis and Biological Evaluation of 5, 6-Diarylimidazo[2.1-b]Thiazole As Selective Cox-2 Inhibitors, *Bioorganic & Med. Chem. Ltrs.*, vol. 7, No. 1, 1997, pp. 47-52.

Akahane, Atsushi, "Discovery of 6-Oxo-3-(2-Phenlypyrazolo[1,5-a]pyridin-3-yl)-1(6H)-pyridazinebutanoic Acid (FR 838): A Novel Xanthine Adenosine $A_1$ Receptor Antagonist with Potent Diuretic Activity," *Journal of Medicinal Chemistry*, vol. 42, No. 5, 1999, pp. 779-783.

Talley, John J., 5 Selective Inhibitors of Cyclooxygenase-2 (COX-2) *Progress in Medicinal Chemistry*, vol. 36, (1999): pp. 201-234.

Boehm, J.C., et al. "1-Substituted 4-Aryl-5-pyridinylimidazoles: A New Class of Cytokine Suppressive Drugs with Low 5-Lipoxygenase and Cyclooxygenase Inhibitory Potency." J. Med. Chem. 1996, 39, pp. 3929-3937.

Hanson, G.J., et al. "Pulmonary-Allergy, Dermatological, Gastrointestinal & Arthritis, Inhibitors of p. 38 kinase." Expert Opinion Ther. Patents, 1997, 7(7):729-733.

Roizman et al., "The Family Herpesviridae: A Brief Introduction," *Field Virology* vol. 2, 4th Edition, pp. 2381-2397, 2001.

\* cited by examiner

ANTIVIRAL PYRAZOLOPYRIDINE COMPOUNDS

CROSS REFERENCES TO RELATED APPLICATIONS

This application is a 371 Application of PCT/US02/08793, filed 21 Mar. 2002, which claims priority to U.S. application Ser. No. 60/282,749, filed 10 Apr. 2001.

BACKGROUND OF THE INVENTION

The present invention relates to novel compounds, pharmaceutical formulations comprising these compounds, and the use of these compounds in therapy. More particularly, the present invention relates to compounds for the prophylaxis and treatment of herpes viral infections.

Of the DNA viruses, those of the herpes group are the sources of the most common viral illnesses in man. The group includes herpes simplex virus types 1 and 2 (HSV1 and 2), varicella zoster virus (VZV), cytomegalovirus (CMV), Epstein-Barr virus (EBV), human herpes virus type 6 (HHV-6), human herpes virus type 7 (HHV-7) and human herpes virus type 8 (HHV-8). HSV-1 and HSV-2 are some of the most common infectious agents of man. Most of these viruses are able to persist in the host's neural cells; once infected, individuals are at risk of recurrent clinical manifestations of infection which can be both physically and psychologically distressing.

Herpes simplex viruses (HSV-1 and -2) are the causative agents of herpes labialis and genital herpes. HSV infection is often characterised by extensive and debilitating lesions of the skin, mouth and/or genitals. Primary infections may be subclinical although tend to be more severe than infections in individuals previously exposed to the virus. Ocular infection by HSV can lead to keratitis or cataracts thereby endangering the host's sight. Infection in the new-born, in immunocompromised patients or penetration of the infection into the central nervous system can prove fatal. In the US alone, 40 million individuals are infected with HSV-2, a number that is expected to increase to 60 million by 2007. Over 80% of individuals infected with HSV-2 are unaware they carry and spread the virus, and of those diagnosed less than 20% received oral therapies. The net result is that less than 5% of the infected population are treated. Likewise of the 530 million individuals worldwide who carry HSV-1, 81% of the symptomatic population remain untreated. No cure exists for HSV infection, and once infected, individuals carry the virus for life in a dormant state. Reactivation of the virus from latency occurs periodically and may be triggered by stress, environmental factors, and/or suppression of the host immune system. Currently, the use of nucleoside analogs such as valaciclovir (Valtrex®) and aciclovir (Zovirax®) is the standard of care for managing genital herpes virus outbreaks.

Varicella zoster virus (VZV) (also know as herpes zoster virus) is a herpes virus which causes chickenpox and shingles. Chickenpox is the primary disease produced in a host without immunity, and in young children is usually a mild illness characterised by a vesicular rash and fever. Shingles or zoster is the recurrent form of the disease which occurs in adults who were previously infected with VZV. The clinical manifestations of shingles are characterised by neuralgia and a vesicular skin rash that is unilateral and dermatomal in distribution. Spread of inflammation may lead to paralysis or convulsions. Coma can occur if the meninges become affected. VZV is of serious concern in patients receiving immunosuppressive drugs for transplant purposes or for treatment of malignant neoplasia and is a serious complication of AIDS patients due to their impaired immune system.

In common with other herpes viruses, infection with CMV leads to a lifelong association of virus and host. Congenital infection following infection of the mother during pregnancy may give rise to clinical effects such as death or gross disease (microcephaly, hepatosplenomegaly, jaundice, mental retardation), retinitis leading to blindness or, in less severe forms, failure to thrive, and susceptibility to chest and ear infections. CMV infection in patients who are immunocompromised for example as a result of malignancy, treatment with immunosuppressive drugs following transplantation or infection with Human Immunodeficiency Virus, may give rise to retinitis, pneumonitis, gastrointestinal disorders and neurological diseases. CMV infection is also associated with cardiovascular diseases and conditions including restenosis and atherosclerosis.

The main disease caused by EBV is acute or chronic infectious mononucleosis (glandular fever). Examples of other EBV or EBV associated diseases include lymphoproliferative disease which frequently occurs in persons with congenital or acquired cellular immune deficiency, X-linked lymphoproliferative disease which occurs namely in young boys, EBV-associated B-cell tumours, Hodgkin's disease, nasopharyngeal carcinoma, Burkitt lymphoma, non-Hodgkin lymphoma, thymomas and oral hairy leukoplakia. EBV infections have also been found in association with a variety of epithelial-cell-derived tumours of the upper and lower respiratory tracts including the lung. EBV infection has also been associated with other diseases and conditions including chronic fatigue syndrome, multiple sclerosis and Alzheimer's disease.

HHV-6 has been shown to be a causative agent of infantum subitum in children and of kidney rejection and interstitial pneumonia in kidney and bone marrow transplant patients, respectively, and may be associated with other diseases such as multiple sclerosis. There is also evidence of repression of stem cell counts in bone marrow transplant patients. HHV-7 is of undetermined disease aetiology.

Hepatitis B virus (HBV) is a viral pathogen of world-wide major importance. The virus is aetiologically associated with primary hepatocellular carcinoma and is thought to cause 80% of the world's liver cancer. Clinical effects of infection with HBV range from headache, fever, malaise, nausea, vomiting, anorexia and abdominal pains. Replication of the virus is usually controlled by the immune response, with a course of recovery lasting weeks or months in humans, but infection may be more severe leading to persistent chronic liver disease outlined above.

BRIEF SUMMARY OF THE INVENTION

According to a first aspect of the invention there is provided a compound of formula (I):

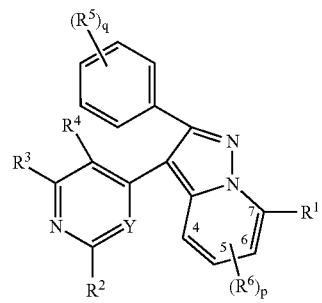

wherein:
$R^1$ is H;

R² is selected from the group consisting of halo, alkyl, cycloalkyl, alkenyl, cycloalkenyl, Ay, Het, —OR⁷, —OAy, —OHet, —OR¹⁰Het, —S(O)$_n$R⁹, —S(O)$_n$Ay, —S(O)$_n$Het, —S(O)$_n$NR⁷R⁸, —NR⁷R⁸, —NHHet, —NHR¹⁰Het, —NHR¹⁰Ay, —R¹⁰NR⁷R⁸ and —R¹⁰NR⁷Ay;

each R⁷ and R⁸ are the same or different and are independently selected from the group consisting of H, alkyl, cycloalkyl, alkenyl, cycloalkenyl, —OR⁹, —C(O)R⁹, —CO₂R⁹, —C(O)NR⁹R¹¹, —C(S)NR⁹R¹¹, —C(NH)NR⁹R¹¹, —SO₂R¹⁰, —SO₂NR⁹R¹¹, —R¹⁰cycloalkyl, —R¹⁰OR⁹, —R¹⁰NR⁹R¹¹, —R¹⁰C(O)R⁹, —R¹⁰CO₂R⁹, —R¹⁰C(O)NR⁹R¹¹, —R¹⁰C(S)NR⁹R¹¹, —R¹⁰NHC(NH)NR⁹R¹¹, —R¹⁰C(NH)NR⁹R¹¹, —R¹⁰SO₂R¹⁰, —R¹⁰SO₂NR⁹R¹¹, —R¹⁰NHSO₂R⁹, —R¹⁰NHCOR⁹ and —R¹⁰SO₂NHCOR⁹;

each R⁹ and R¹¹ are the same or different and are independently selected from the group consisting of H, alkyl, cycloalkyl, —R¹⁰cycloalkyl, —R¹⁰OH, —R¹⁰(OR¹⁰)$_w$ where w is 1–10, and —R¹⁰NR¹⁰R¹⁰;

each R¹⁰ is the same or different and is independently selected from the group consisting of alkyl, cycloalkyl, alkenyl, cycloalkenyl and alkynyl;

n is 0, 1 or 2;

Ay is aryl;

Het is a 5- or 6-membered heterocyclic or heteroaryl group;

Y is N or CH;

R³ and R⁴ are the same or different and are each independently selected from the group consisting of H, halo, alkyl, cycloalkyl, alkenyl, Ay, Het, —OR⁷, —OAy, —C(O)R⁷, —C(O)Ay, —CO₂R⁷, —CO₂Ay, —SO₂NHR⁹, —NR⁷R⁸, —NR⁷Ay, —NHHet, —NHR¹⁰Het, —R¹⁰OR⁷, —R¹⁰OAy, —R¹⁰NR⁷R⁸ and —R¹⁰NR⁷Ay;

q is 0, 1, 2, 3, 4 or 5;

each R⁵ is the same or different and is independently selected from the group consisting of halo, alkyl, cycloalkyl, alkenyl, cycloalkenyl, alkynyl, Ay, Het, —OR⁷, —OAy, —OHet, —C(O)R⁹, —CO₂R⁹, —C(O)NR⁷R⁸, —C(O)Ay, —C(O)NR⁷Ay, —C(O)Het, —C(O)NHR¹⁰Het, —C(S)NR⁹R¹¹, —C(NH)NR⁷R⁸, —C(NH)NR⁷Ay, —S(O)$_n$R⁹, —S(O)₂NR⁷R⁸, —S(O)₂NR⁷Ay, —NR⁷R⁸, —NR⁷Ay, —NHHet, —NHR¹⁰Ay, —NHR¹⁰Het, —R¹⁰cycloalkyl, —R¹⁰OR⁹, —R¹⁰NR⁷R⁸, —R¹⁰NR⁷Ay, —R¹⁰C(O)R⁹, —R¹⁰CO₂R⁹, —R¹⁰C(O)NR⁹R¹¹, —R¹⁰C(S)NR⁹R¹¹, —R¹⁰NHC(NH)NR⁹R¹¹, —R¹⁰C(NH)NR⁹R¹¹, —R¹⁰SO₂R⁹, —R¹⁰SO₂NHCOR⁹, —R¹⁰SO₂NR⁹R¹¹, cyano, nitro and azido; or two adjacent R⁵ groups together with the atoms to which they are bonded form a C$_{5-6}$ cycloalkyl or aryl;

p is 1, 2 or 3; and each R⁶ is the same or different and is independently selected from the group consisting of halo, alkyl, cycloalkyl, alkenyl, cycloalkenyl, alkynyl, Ay, Het, —OR⁷, —OAy, —OHet, —OR¹⁰Ay, —OR¹⁰Het, —C(O)R⁹, —CO₂R⁹, —C(O)NR⁷R⁸, —C(O)Ay, —C(O)NR⁷Ay, —C(O)NHR¹⁰Ay, —C(O)Het, —C(O)NHR¹⁰Het, —C(S)NR⁹R¹¹, —C(NH)NR⁷R⁸, —C(NH)NR⁷Ay, —S(O)$_n$R⁹, —S(O)$_n$Ay, —S(O)$_n$Het, —S(O)₂NR⁷R⁸, —S(O)₂NR⁷Ay, —NR⁷R⁸, —NR⁷Ay, —NHR¹⁰Ay, —NHHet, —NHR¹⁰Het, —R¹⁰cycloalkyl, —R¹⁰Ay, —R¹⁰Het, —R¹⁰OR⁹, —R¹⁰—O—C(O)R⁹, —R¹⁰—O—C(O)Ay, —R¹⁰—O—C(O)Het, —R¹⁰—O—S(O)$_n$R⁹, —R¹⁰NR⁷R⁸, —R¹⁰NR⁷Ay, —R¹⁰C(O)R⁹, —R¹⁰CO₂R⁹, —R¹⁰C(O)NR⁹R¹¹, —R¹⁰C(S)NR⁹R¹¹, —R¹⁰NHC(NH)NR⁹R¹¹, —R¹⁰C(NH)NR⁹R¹¹, —R¹⁰SO₂R⁹, —R¹⁰SO₂NHCOR⁹, —R¹⁰SO₂NR⁹R¹¹, cyano, nitro and azido; or two adjacent R⁶ groups together with the atoms to which they are bonded form a C$_{5-6}$cycloalkyl or a 5- or 6-membered heterocyclic group containing 1 or 2 heteroatoms;

wherein at least one R⁶ is selected from the group consisting of —NR⁷R⁸, —NR⁷Ay, —NHHet, —NHR¹⁰Ay and —NHR¹⁰Het; and wherein when Y is CH, R³ is not —NR⁷AY;

and pharmaceutically acceptable salts, solvates and physiologically functional derivatives thereof.

According to another aspect, the present invention provides a pharmaceutical composition comprising a compound of formula (I). In one embodiment, the pharmaceutical composition further comprises a pharmaceutically acceptable carrier or diluent. In one embodiment, the pharmaceutical composition further comprises an antiviral agent selected from the group consisting of aciclovir and valaciclovir.

According to a third aspect, the present invention provides a method for the prophylaxis or treatment of a herpes viral infection in an animal. The method comprises administering to the animal a therapeutically effective amount of a compound of formula (I) or a pharmaceutically acceptable salt, solvate or physiologically functional derivative thereof. The herpes viral infection may be herpes simplex virus 1, herpes simplex virus 2, cytomegalovirus, Epstein Barr virus, varicella zoster virus, human herpes virus 6, human herpes virus 7, or human herpes virus 8.

According to a fourth aspect, the present invention provides a method for the prophylaxis or treatment of conditions or diseases associated with a herpes viral infection in an animal. The method comprises administering to the animal a therapeutically effective amount of the compound of formula (I) or a pharmaceutically acceptable salt, solvate or physiologically functional derivative thereof.

According to a fifth aspect, the present invention provides a process for preparing a compound of formula (I) wherein Y is N, R² is selected from the group consisting of alkyl, cycloalkyl, alkenyl, cycloalkenyl, Ay, Het, —OR⁷, —OAy, —OHet, —OR¹⁰Het —S(O)$_n$R⁹, —S(O)$_n$Ay, —S(O)$_n$Het, —S(O)$_n$NR⁷R⁸, —NR⁷R⁸, —NHHet, —NHR¹⁰Het, —NHR¹⁰Ay, —R¹⁰NR⁷R⁸ and —R¹⁰NR⁷Ay; and R³ and R⁴ are H, said process comprising reacting a compound of formula (IX):

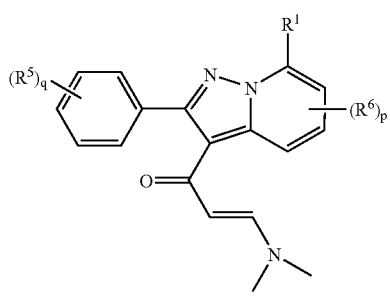

IX wherein at least one R⁶ is selected from the group consisting of —NR⁷R⁸, —NR⁷Ay, —NHHet, —NHR¹⁰Ay and —NHR¹⁰Het;

with an amine of formula (X):

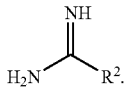

According to a sixth aspect, the present invention provides a process for preparing a compound of formula (I). The process comprises the steps of:

(a) reacting the compound of formula (XXXII)

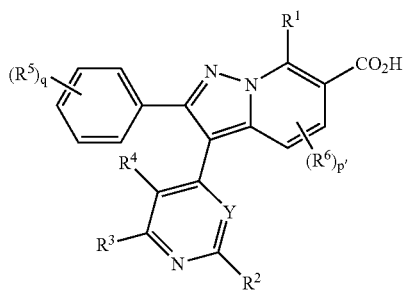

wherein p' is 0, 1 or 2;

with diphenylphosphoryl azide in tert-butanol to give the compound of formula (I-X)

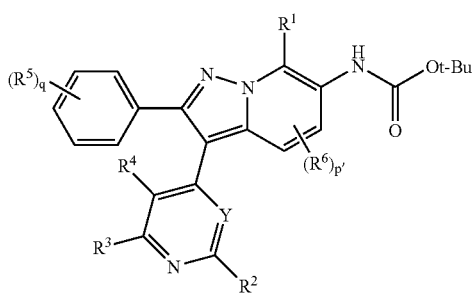

(b) optionally cleaving the compound of formula (I-X) to give the compound of formula (I-Y)

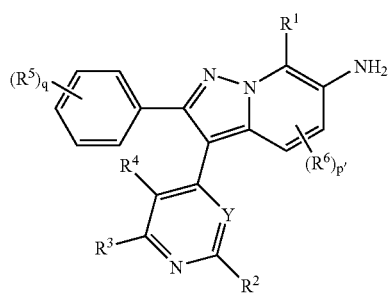

and (c) optionally converting the compound of formula (I-Y) to a compound of formula (I-Z)

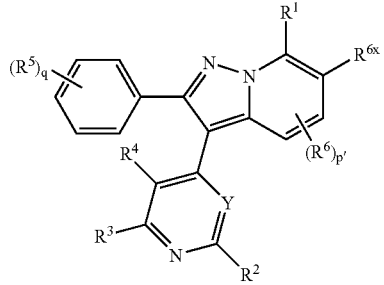

wherein $R^{6x}$ is selected from the group consisting of —$NR^7R^8$ where $R^7$ and $R^8$ are not both H, —$NR^7Ay$, —NHHet, —$NHR^{10}Ay$ and —$NHR^{10}Het$;

using conditions selected from the group consisting of cross coupling, reductive amination, alkylation, acylation and sulfonylation.

According to a seventh aspect, the present invention provides a process for preparing a compound of formula (I) wherein Y is N; $R^2$ is selected from the group consisting of alkyl, cycloalkyl, alkenyl, cycloalkenyl, Ay, Het, —$OR^7$, —OAy, —OHet, —$OR^{10}$Het —$S(O)_nR^9$, —$S(O)_nAy$, —$S(O)_n$Het, —$S(O)_nNR^7R^8$, —$NR^7R^8$, —NHHet, —$NHR^{10}$Het, —$NHR^{10}Ay$, —$R^{10}NR^7R^8$ and —$R^{10}NR^7Ay$; $R^3$ is selected from the group consisting of H, alkyl cycloalkyl, alkenyl, Ay, Het, —$C(O)R^7$, —C(O)Ay, —$CO_2R^7$, —$CO_2Ay$, —$SO_2NHR^9$, —$NR^7R^8$ (where $R^7$ and $R^8$ are not H), —$NR^7Ay$ (where $R^7$ is not H), —$R^{10}OR^7$, —$R^{10}OAy$, —$R^{10}NR^7R^8$ and —$R^{10}NR^7Ay$; $R^4$ is H; and at least one $R^6$ is selected from the group consisting of —$NR^7R^8$, —$NR^7Ay$, —NHHet, —$NHR^{10}Ay$ and —$NHR^{10}$Het. The process comprises the steps of:

a) reacting a compound of formula (XVI):

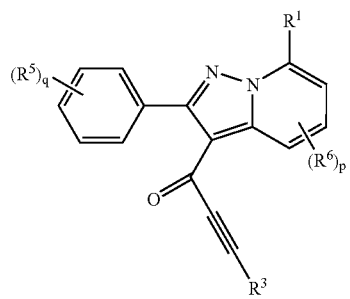

wherein each $R^6$ is the same or different and is independently selected from the group consisting of halo, alkyl, cycloalkyl, alkenyl, cycloalkenyl, alkynyl, Ay, Het, —$OR^7$, —OAy, —OHet, —$OR^{10}Ay$, —$OR^{10}$Het, —$C(O)R^9$, —$CO_2R^9$, —$C(O)NR^7R^8$, —C(O)Ay, —$C(O)NR^7Ay$, —$C(O)NHR^{10}Ay$, —C(O)Het, —$C(O)NHR^{10}$Het, —$C(S)NR^9R^{11}$, —$C(NH)NR^7R^8$, —$C(NH)NR^7Ay$, —$S(O)_nR^9$, —$S(O)_nAy$, —$S(O)_n$Het, —$S(O)_2NR^7R^8$, —$S(O)_2NR^7Ay$, —$NR^7R^8$, —$NR^7Ay$, —$NHR^{10}Ay$, —NHHet, —$NHR^{10}$Het, —$R^{10}$cycloalkyl, —$R^{10}Ay$, —$R^{10}$Het, —$R^{10}OR^9$, —$R^{10}$—O—$C(O)R^9$, —$R^{10}$—O—C(O)Ay, —$R^{10}$—

O—C(O)Het, —R$^{10}$—O—S(O)$_n$R$^9$, —R$^{10}$NR$^7$R$^8$, —R$^{10}$NR$^7$Ay, —R$^{10}$C(O)R$^9$, —R$^{10}$CO$_2$R$^9$, —R$^{10}$C(O)NR$^9$R$^{11}$, —R$^{10}$C(S)NR$^9$R$^{11}$, —R$^{10}$NHC(NH)NR$^9$R$^{11}$, —R$^{10}$C(NH)NR$^9$R$^{11}$, —R$^{10}$SO$_2$R$^9$, —R$^{10}$SO$_2$NHCOR$^9$, —R$^{10}$SO$_2$NR$^9$R$^{11}$, cyano, nitro and azido; or two adjacent R$^6$ groups together with the atoms to which they are bonded form a C$_{5-6}$cycloalkyl or a 5- or 6-membered heterocyclic group containing 1 or 2 heteroatoms;

wherein at least one R$^6$ is selected from the group consisting of halo, —NR$^7$R$^8$, —NR$^7$Ay, —NHHet, —NHR$^{10}$Ay and —NHR$^{10}$Het; and with an amine of formula (X):

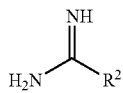

X to prepare a compound of formula (XVII)

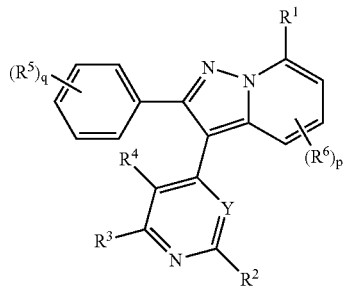

XVII wherein at least one R$^6$ is selected from the group consisting of halo, —NR$^7$R$^8$, —NR$^7$Ay, —NHHet, —NHR$^{10}$Ay and —NHR$^{10}$Het; and b) in the embodiment wherein no R$^6$ is —NR$^7$R$^8$, —NR$^7$Ay, —NHHet, —NHR$^{10}$Ay or —NHR$^{10}$Het, replacing R$^6$ halo of the compound of formula (XVII) with an amine substituent selected from the group consisting of —NR$^7$R$^8$, —NR$^7$Ay, —NHHet, —NHR$^{10}$Ay and —NHR$^{10}$Het;

to prepare a compound of formula (I).

According to another aspect, the present invention provides a process for preparing the compounds of formula (I) wherein Y is N; R$^2$ is selected from the group consisting of alkyl, cycloalkyl, alkenyl, cycloalkenyl, Ay, Het, —OR$^7$, —OAy, —OHet, —OR$^{10}$Het —S(O)$_n$R$^9$, —S(O)$_n$Ay, —S(O)$_n$Het, —S(O)$_n$NR$^7$R$^8$, —NR$^7$R$^8$, —NHHet, —NHR$^{10}$Het, —NHR$^{10}$Ay, —R$^{10}$NR$^7$R$^8$ and —R$^{10}$NR$^7$Ay; and at least one R$^6$ is selected from the group consisting of —NR$^7$R$^8$, —NR$^7$Ay, —NHHet, —NHR$^{10}$Ay and —NHR$^{10}$Het. The process comprises the steps of:

a) reacting a compound of formula (XX):

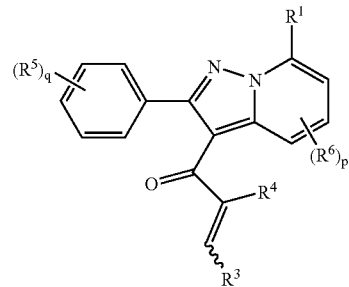

XX wherein each R$^6$ is the same or different and is independently selected from the group consisting of halo, alkyl, cycloalkyl, alkenyl, cycloalkenyl, alkynyl, Ay, Het, —OR$^7$, —OAy, —OHet, —OR$^{10}$Ay, —OR$^{10}$Het, —C(O)R$^9$, —CO$_2$R$^9$, —C(O)NR$^7$R$^8$, —C(O)Ay, —C(O)NR$^7$Ay, —C(O)NHR$^{10}$Ay, —C(O)Het, —C(O)NHR$^{10}$Het, —C(S)NR$^9$R$^{11}$, —C(NH)NR$^7$R$^8$, —C(NH)NR$^7$Ay, —S(O)$_n$R$^9$, —S(O)$_n$Ay, —S(O)$_n$Het, —S(O)$_2$NR$^7$R$^8$, —S(O)$_2$NR$^7$Ay, —NR$^7$R$^8$, —NR$^7$Ay, —NHR$^{10}$Ay, —NHHet, —NHR$^{10}$Het, —R$^{10}$cycloalkyl, —R$^{10}$Ay, —R$^{10}$Het, —R$^{10}$OR$^9$, —R$^{10}$—O—C(O)R$^9$, —R$^{10}$—O—C(O)Ay, —R$^{10}$—O—C(O)Het, —R$^{10}$—O—S(O)$_n$R$^9$, —R$^{10}$NR$^7$R$^8$, —R$^{10}$NR$^7$Ay, —R$^{10}$C(O)R$^9$, —R$^{10}$CO$_2$R$^9$, —R$^{10}$C(O)NR$^9$R$^{11}$, —R$^{10}$C(S)NR$^9$R$^{11}$, —R$^{10}$NHC(NH)NR$^9$R$^{11}$, —R$^{10}$C(NH)NR$^9$R$^{11}$, —R$^{10}$SO$_2$R$^9$, —R$^{10}$SO$_2$NHCOR$^9$, —R$^{10}$SO$_2$NR$^9$R$^{11}$, cyano, nitro and azido; or two adjacent R$^6$ groups together with the atoms to which they are bonded form a C$_{5-6}$cycloalkyl or a 5- or 6-membered heterocyclic group containing 1 or 2 heteroatoms;

wherein at least one R$^6$ is selected from the group consisting of halo, —NR$^7$R$^8$, —NR$^7$Ay, —NHHet, —NHR$^{10}$Ay and —NHR$^{10}$Het;

with an amine of formula (X):

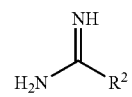

X to prepare an intermediate compound;

b) oxidizing the intermediate compound to prepare a compound of formula (XVII)

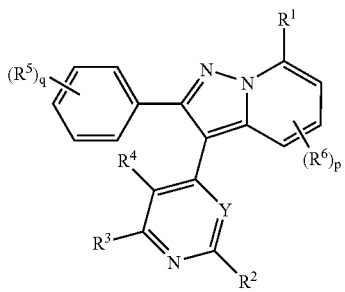

XVII wherein at least one $R^6$ is selected from the group consisting of halo, —$NR^7R^8$, —$NR^7Ay$, —NHHet, —$NHR^{10}Ay$ and —$NHR^{10}$Het; and c) in the embodiment wherein no $R^6$ is —$NR^7R^8$, —$NR^7Ay$, —NHHet, —$NHR^{10}Ay$ or —$NHR^{10}$Het, replacing $R^6$ halo of the compound of formula (XVII) with an amine substituent selected from the group consisting of —$NR^7R^8$, —$NR^7Ay$, —NHHet, —$NHR^{10}Ay$ and —$NHR^{10}$Het;

to prepare a compound of formula (I).

According to another aspect, the present invention provides a process for preparing the compounds of formula (I) wherein at least one $R^6$ is selected from the group consisting of —$NR^7R^8$, —$NR^7Ay$, —NHHet, —$NHR^{10}Ay$ and —$NHR^{10}$Het. The process comprises the steps of:

a) reacting a compound of formula (XXII):

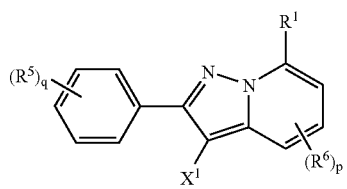

XXII wherein each $R^6$ is the same or different and is independently selected from the group consisting of halo, alkyl, cycloalkyl, alkenyl, cycloalkenyl, alkynyl, Ay, Het, —$OR^7$, —OAy, —OHet, —$OR^{10}Ay$, —$OR^{10}$Het, —$C(O)R^9$, —$CO_2R^9$, —$C(O)NR^7R^8$, —C(O)Ay, —$C(O)NR^7Ay$, —$C(O)NHR^{10}Ay$, —C(O)Het, —$C(O)NHR^{10}$Het, —$C(S)NR^9R^{11}$, —$C(NH)NR^7R^8$, —$C(NH)NR^7Ay$, —$S(O)_nR^9$, —$S(O)_nAy$, —$S(O)_n$Het, —$S(O)_2NR^7R^8$, —$S(O)_2NR^7Ay$, —$NR^7R^8$, —$NR^7Ay$, —$NHR^{10}Ay$, —NHHet, —$NHR^{10}$Het, —$R^{10}$cycloalkyl, —$R^{10}Ay$, —$R^{10}$Het, —$R^{10}OR^9$, —$R^{10}$—O—$C(O)R^9$, —$R^{10}$—O—C(O)Ay, —$R^{10}$—O—C(O)Het, —$R^{10}$—O—$S(O)_nR^9$, —$R^{10}NR^7R^8$, —$R^{10}NR^7Ay$, —$R^{10}C(O)R^9$, —$R^{10}CO_2R^9$, —$R^{10}C(O)NR^9R^{11}$, —$R^{10}C(S)NR^9R^{11}$, —$R^{10}NHC(NH)NR^9R^{11}$, —$R^{10}C(NH)NR^9R^{11}$, —$R^{10}SO_2R^9$, —$R^{10}SO_2NHCOR^9$, —$R^{10}SO_2NR^9R^{11}$, cyano, nitro and azido; or two adjacent $R^6$ groups together with the atoms to which they are bonded form a $C_{5-6}$cycloalkyl or a 5- or 6-membered heterocyclic group containing 1 or 2 heteroatoms;

wherein at least one $R^6$ is selected from the group consisting of halo, —$NR^7R^8$, —$NR^7Ay$, —NHHet, —$NHR^{10}Ay$ and —$NHR^{10}$Het; and $X^1$ is chloro, bromo or iodo with a compound of formula (XXIV):

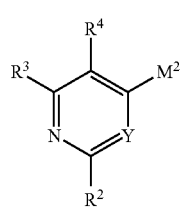

XXIV wherein $M^2$ is selected from the group consisting of —$B(OH)_2$, —$B(ORa)_2$, —$B(Ra)_2$, —$Sn(Ra)_3$, Zn-halide, ZnRa, and Mg-halide where Ra is alkyl or cycloalkyl and halide is halo;

to prepare a compound of formula (XVII)

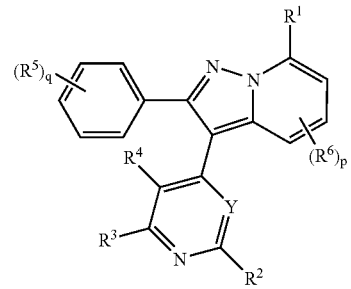

XVII wherein at least one $R^6$ is selected from the group consisting of halo, —$NR^7R^8$, —$NR^7Ay$, —NHHet, —$NHR^{10}Ay$ and —$NHR^{10}$Het; and b) in the embodiment wherein no $R^6$ is —$NR^7R^8$, —$NR^7Ay$, —NHHet, —$NHR^{10}Ay$ or —$NHR^{10}$Het, replacing $R^6$ halo of the compound of formula (XVII) with an amine substituent selected from the group consisting of —$NR^7R^8$, —$NR^7Ay$, —NHHet, —$NHR^{10}Ay$ and —$NHR^{10}$Het;

to prepare a compound of formula (I).

According to another aspect, the present invention provides a radiolabeled compound of formula (I) or a pharmaceutically acceptable salt, solvate or physiologically functional derivative thereof. In one embodiment, the radiolabeled compound is tritiated. In another aspect, the present invention provides a biotinylated compound of formula (I) or a pharmaceutically acceptable salt, solvate or physiologically functional derivative thereof.

According to another aspect, the present invention provides a compound of formula (I) for use in therapy. The present invention also provides a compound of formula (I) for the prophylaxis or treatment of a herpes viral infection in an animal. The present invention also provides a compound of formula (I) for the prophylaxis or treatment of conditions or diseases associated with a herpes viral infection in an animal.

According to another aspect, the present invention provides the use of a compound of formula (I) for the preparation of a medicament for prophylaxis or treatment of a herpes viral infection in an animal, preferably humans. The present invention also provides the use of a compound of formula (I) for the preparation of a medicament for the prophylaxis or treatment of conditions or diseases associated with a herpes viral infection in an animal, preferably humans.

According to another aspect, the present invention provides a pharmaceutical composition comprising a compound of formula (I) for use in the prophylaxis or treatment of a herpes viral infection in an animal.

DETAILED DESCRIPTION OF THE INVENTION

As used herein, "a compound of the invention" or "compound of formula (I)" means a compound of formula (I) or a pharmaceutically acceptable salt, solvate, or physiologically functional derivative thereof. Similarly, with respect to isolatable intermediates such as for example, compounds of formula (IX), (XXXII), (XVI), (XVII), (XX), (XXII), (XXX), (XXXI) and (XXXII), the phrase "a compound of formula (number)" means a compound having that formula and pharmaceutically acceptable salts, solvates and physiologically functional derivatives thereof.

As used herein, the terms "alkyl" (and alkylene) refer to straight or branched hydrocarbon chains containing from 1 to 8 carbon atoms. Examples of "alkyl" as used herein include, but are not limited to, methyl, ethyl, n-propyl, n-butyl, n-pentyl, isobutyl, isopropyl, and tert-butyl. Examples of "alkylene" as used herein include, but are not limited to, methylene, ethylene, propylene, butylene, and isobutylene. "Alkyl" also includes substituted alkyl. The alkyl groups may be optionally substituted with one or more substituents selected from the group consisting of mercapto, nitro, cyano and halo. Perhaloalkyl, such as trifluoromethyl, is one preferred alkyl group.

As used herein, the term "cycloalkyl" refers to a non-aromatic carbocyclic ring having from 3 to 8 carbon atoms and no carbon-carbon double bonds. "Cycloalkyl" includes by way of example cyclopropyl, cyclobutyl, cyclopentyl, cyclohexyl, cycloheptyl and cyclooctyl. "Cycloalkyl" also includes substituted cycloalkyl. The cycloalkyl may optionally be substituted on an available carbon with one or more substituents selected from the group consisting of mercapto, nitro, cyano, halo, and alkyl.

As used herein, the term "alkenyl" (and alkenylene) refers to straight or branched hydrocarbon chains containing from 2 to 8 carbon atoms and at least one and up to three carbon-carbon double bonds. Examples of "alkenyl" as used herein include, but are not limited to ethenyl and propenyl. "Alkenyl" also includes substituted alkenyl. The alkenyl groups may optionally be substituted on an available carbon with one or more substituents selected from the group consisting of mercapto, nitro, cyano, halo, and alkyl.

As used herein, the term "cycloalkenyl" refers to a non-aromatic carbocyclic ring having from 3 to 8 carbon atoms (unless otherwise specified) and up to 3 carbon-carbon double bonds. "Cycloalkenyl" includes by way of example cyclobutenyl, cyclopentenyl and cyclohexenyl. "Cycloalkenyl" also includes substituted cycloalkenyl. The cycloalkenyl may optionally be substituted on an available carbon with one or more substituents selected from the group consisting of mercapto, nitro, cyano, halo, and alkyl.

As used herein, the term "alkynyl" (and alkenylene) refers to straight or branched hydrocarbon chains containing from 2 to 8 carbon atoms and at least one and up to three carbon-carbon triple bonds. Examples of "alkynyl" as used herein include, but are not limited to ethynyl and propynyl. "Alkynyl" also includes substituted alkynyl. The alkynyl groups may optionally be substituted on an available carbon with one or more substituents selected from the group consisting of mercapto, nitro, cyano, halo, and alkyl.

The term "halo" or "halogen" refers to the elements fluorine, chlorine, bromine and iodine.

The term "aryl" refers to monocyclic carbocyclic groups and fused bicyclic carbocyclic groups having from 5 to 12 carbon atoms and having at least one aromatic ring. Examples of particular aryl groups include but are not limited to phenyl and naphthyl. "Aryl" also includes substituted aryl. Aryl groups may optionally be substituted on an available carbon with one or more substituents selected from the group consisting of halo, alkyl (including perhaloalkyl), alkenyl, cycloalkyl, cycloalkenyl, alkoxy, cycloalkoxy, amino, mercapto, hydroxy, alkylhydroxy, alkylamine, cycloalkylamine, carboxy, carboxamide, sulfonamide, Het, amidine, cyano, nitro and azido. Preferred aryl groups according to the invention include but are not limited to phenyl and substituted phenyl.

The term "heterocyclic" (or "heterocycle") refers to a monocyclic saturated or unsaturated non-aromatic groups and fused bicyclic non-aromatic groups, having the specified number of members and containing 1, 2, 3 or 4 heteroatoms selected from N, O and S. Examples of particular heterocyclic groups include but are not limited to tetrahydrofuran, dihydropyran, tetrahydropyran, pyran, oxetane, thietane, 1,4-dioxane, 1,3-dioxane, 1,3-dioxalane, piperidine, piperazine, tetrahydropyrimidine, pyrrolidine, morpholine, thiomorpholine, thiazolidine, oxazolidine, tetrahydrothiopyran, tetrahydrothiophene, and the like. "Heterocyclic" also includes substituted heterocyclic. The heterocyclic group may be optionally substituted on an available carbon or heteroatom, with one or more substituents selected from the group consisting of halo, alkyl (including perhaloalkyl), alkenyl, cycloalkyl, cycloalkenyl, alkoxy, cycloalkoxy, amino, mercapto, hydroxy, alkylhydroxy, alkylamine, cycloalkylamine, carboxy, carboxamide, sulfonamide, Het, amidine, cyano, nitro and azido. Preferred heterocyclic groups according to the invention include but are not limited to pyrrolidine, piperidine, morpholine, thiomorpholine and piperazine and subsituted variants thereof.

The term "heteroaryl" refers to aromatic monocyclic groups and aromatic fused bicyclic groups wherein at least one ring is aromatic, having the specified number of members (total carbon and heteroatoms) and containing 1, 2, 3, or 4 heteroatoms selected from N, O and S. Examples of particular heteroaryl groups include but are not limited to furan, thiophene, pyrrole, imidazole, pyrazole, triazole, tetrazole, thiazole, oxazole, isoxazole, oxadiazole, thiadiazole, isothiazole, pyridine, pyridazine, pyrazine, pyrimidine, quinoline, isoquinoline, benzofuran, benzothiophene, indole, and indazole. "Heteroaryl" also includes substituted heteroaryl. The heteroaryl group may optionally be substituted on an available carbon or heteroatom with one or more substituents selected from the group consisting of halo, alkyl (including perhaloalkyl), alkenyl, cycloalkyl, cycloalkenyl, alkoxy, cycloalkoxy, amino, mercapto, hydroxy, alkylhydroxy, alkylamine, cycloalkylamine, carboxy, carboxamide, sulfonamide, Het, amidine, cyano, nitro and azido. Preferred heteroaryl groups according to the invention include but are not limited to pyridine, furan, thiophene, pyrrole, imidazole, pyrazole, and pyrimidine, and substituted variants thereof.

The term "members" and variants thereof (e.g., "membered")in the context of heterocyclic and heteroaryl groups refers to the total atoms, carbon and heteroatoms N, O and/or S, which form the ring. Thus, an example of a 6-membered heterocyclic ring is piperidine and an example of a 6-membered heteroaryl ring is pyridine.

As used herein, the term "optionally" means that the subsequently described event(s) may or may not occur, and includes both event(s) which occur and events that do not occur.

The present invention provides compounds of formula (I):

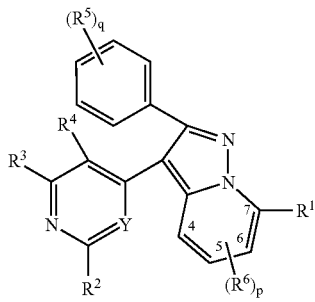

wherein:
R$^1$ is H;
R$^2$ is selected from the group consisting of halo, alkyl, cycloalkyl, alkenyl, cycloalkenyl, Ay, Het, —OR$^7$, —OAy, —OHet, —OR$^{10}$Het, —S(O)$_n$R$^9$, —S(O)$_n$Ay, —S(O)$_n$Het, —S(O)$_n$NR$^7$R$^8$, —NR$^7$R$^8$, —NHHet, —NHR$^{10}$Het, —NHR$^{10}$Ay, —R$^{10}$NR$^7$R$^8$ and —R$^{10}$NR$^7$Ay;
each R$^7$ and R$^8$ are the same or different and are independently selected from the group consisting of H, alkyl, cycloalkyl, alkenyl, cycloalkenyl, —OR$^9$, —C(O)R$^9$, —CO$_2$R$^9$, —C(O)NR$^9$R$^{11}$, —C(S)NR$^9$R$^{11}$, —C(NH)NR$^9$R$^{11}$, —SO$_2$R$^{10}$, —SO$_2$NR$^9$R$^{11}$, —R$^{10}$cycloalkyl, —R$^{10}$OR$^9$, —R$^{10}$NR$^9$R$^{11}$, —R$^{10}$C(O)R$^9$, —R$^{10}$CO$_2$R$^9$, —R$^{10}$C(O)NR$^9$R$^{11}$, —R$^{10}$C(S)NR$^9$R$^{11}$, —R$^{10}$NHC(NH)NR$^9$R$^{11}$, —R$^{10}$C(NH)NR$^9$R$^{11}$, —R$^{10}$SO$_2$R$^{10}$, —R$^{10}$SO$_2$NR$^9$R$^{11}$, —R$^{10}$NHSO$_2$R$^9$, —R$^{10}$NHCOR$^9$ and —R$^{10}$SO$_2$NHCOR$^9$;
each R$^9$ and R$^{11}$ are the same or different and are independently selected from the group consisting of H, alkyl, cycloalkyl, —R$^{10}$cycloalkyl, —R$^{10}$OH, —R$_{10}$(OR$^{10}$)$_w$ where w is 1–10, and —R$^{10}$NR$^{10}$R$^{10}$;
each R$^{10}$ is the same or different and is independently selected from the group consisting of alkyl, cycloalkyl, alkenyl, cycloalkenyl and alkynyl;
n is 0, 1 or 2;
Ay is aryl;
Het is a 5- or 6-membered heterocyclic or heteroaryl group;
Y is N or CH;
R$^3$ and R$^4$ are the same or different and are each independently selected from the group consisting of H, halo, alkyl, cycloalkyl, alkenyl, Ay, Het, —OR$^7$, —OAy, —C(O)R$^7$, —C(O)Ay, —CO$_2$R$^7$, —CO$_2$Ay, —SO$_2$NHR$^9$, —NR$^7$R$^8$, —NR$^7$Ay, —NHHet, —NHR$^{10}$Het, —R$^{10}$OR$^7$, —R$^{10}$OAy, —R$^{10}$NR$^7$R$^8$ and —R$^{10}$NR$^7$Ay;
q is 0, 1, 2, 3, 4 or 5;
each R$^5$ is the same or different and is independently selected from the group consisting of halo, alkyl, cycloalkyl, alkenyl, cycloalkenyl, alkynyl, Ay, Het, —OR$^7$, —OAy, —OHet, —C(O)R$^9$, —CO$_2$R$^9$, —C(O)NR$^7$R$^8$, —C(O)Ay, —C(O)NR$^7$Ay, —C(O)Het, —C(O)NHR$^{10}$Het, —C(S)NR$^9$R$^{11}$, —C(NH)NR$^7$R$^8$, —C(NH)NR$^7$Ay, —S(O)$_n$R$^9$, —S(O)$_2$NR$^7$R$^8$, —S(O)$_2$NR$^7$Ay, —S(O)$_n$NR$^7$R$^8$, —NR$^7$Ay, —NHHet, —NHR$^{10}$Ay, —NHR$^{10}$Het, —R$^{10}$cycloalkyl, —R$^{10}$OR$^9$, —R$^{10}$NR$^7$R$^8$, —R$^{10}$NR$^7$Ay, —R$^{10}$C(O)R$^9$, —R$^{10}$CO$_2$R$^9$, —R$^{10}$C(O)NR$^9$R$^{11}$, —R$^{10}$C(S)NR$^9$R$^{11}$, —R$^{10}$NHC(NH)NR$^9$R$^{11}$, —R$^{10}$C(NH)NR$^9$R$^{11}$, —R$^{10}$SO$_2$R$^9$, —R$^{10}$SO$_2$NHCOR$^9$, —R$^{10}$SO$_2$NR$^9$R$^{11}$, cyano, nitro and azido; or
two adjacent R$^5$ groups together with the atoms to which they are bonded form a C$_{5-6}$ cycloalkyl or aryl;
p is 1, 2 or 3; and
each R$^6$ is the same or different and is independently selected from the group consisting of halo, alkyl, cycloalkyl, alkenyl, cycloalkenyl, alkynyl, Ay, Het, —OR$^7$, —OAy, —OHet, —OR$^{10}$Ay, —OR$^{10}$Het, —C(O)R$^9$, —CO$_2$R$^9$, —C(O)NR$^7$R$^8$, —C(O)Ay, —C(O)NR$^7$Ay, —C(O)NHR$^{10}$Ay, —C(O)Het, —C(O)NHR$^{10}$Het, —C(S)NR$^9$R$^{11}$, —C(NH)NR$^7$R$^8$, —C(NH)NR$^7$Ay, —S(O)$_n$R$^9$, —S(O)$_n$Ay, —S(O)$_n$Het, —S(O)$_2$NR$^7$R$^8$, —S(O)$_2$NR$^7$Ay, —NR$^7$R$^8$, —NR$^7$Ay, —NHR$^{10}$Ay, —NHHet, —NHR$^{10}$Het, —R$^{10}$cycloalkyl, —R$^{10}$Ay, —R$^{10}$Het, —R$^{10}$OR$^9$, —R$^{10}$—O—C(O)R$^9$, —R$^{10}$—O—C(O)Ay, —R$^{10}$—O—C(O)Het, —R$^{10}$—O—S(O)$_n$R$^9$, —R$^{10}$NR$^7$R$^8$, —R$^{10}$NR$^7$Ay, —R$^{10}$C(O)R$^9$, —R$^{10}$CO$_2$R$^9$, —R$^{10}$C(O)NR$^9$R$^{11}$, —R$^{10}$C(S)NR$^9$R$^{11}$, —R$^{10}$NHC(NH)NR$^9$R$^{11}$, —R$^{10}$C(NH)NR$^9$R$^{11}$, —R$^{10}$SO$_2$R$^9$, —R$^{10}$SO$_2$NHCOR$^9$, —R$^{10}$SO$_2$NR$^9$R$^{11}$, cyano, nitro and azido; or
two adjacent R$^6$ groups together with the atoms to which they are bonded form a C$_{5-6}$ cycloalkyl or a 5- or 6-membered heterocyclic group containing 1 or 2 heteroatoms;
wherein at least one R$^6$ is selected from the group consisting of —NR$^7$R$^8$, —NR$^7$Ay, —NHHet, —NHR$^{10}$Ay and —NHR$^{10}$Het; and
wherein when Y is CH, R$^3$ is not —NR$^7$AY;

and pharmaceutically acceptable salts, solvates and physiologically functional derivatives thereof.

In one preferred class of compounds of formula (I), Y is CH. In another preferred embodiment, the compounds of formula (I) are defined wherein Y is N.

Compounds of formula (I) include those compounds defined wherein R$^2$ contains an aryl, heterocyclic or heteroaryl moiety. The groups Ay, Het, —OAy, —OHet, —OR$^{10}$Het, —S(O)$_n$Ay, —S(O)$_n$Het, —NHHet, —NHR$^{10}$Het, —NHR$^{10}$Ay and —R$^{10}$NR$^7$Ay, are examples of groups containing an aryl, heterocyclic or heteroaryl moiety. In one embodiment, compounds of the present invention include those compounds defined wherein R$^2$ contains a heterocyclic or heteroaryl moiety such as Het, —OHet, —OR$^{10}$Het —S(O)$_n$Het, —NHHet and —NHR$^{10}$Het Another class of compounds of formula (I) includes those compounds defined wherein R$^2$ does not contain an aryl, heterocyclic or heteroaryl moiety. In such embodiments R$^2$ is preferably selected from the group consisting of halo, alkyl, cycloalkyl, alkenyl, cycloalkenyl, —OR$^7$, —S(O)$_n$R$^9$, —S(O)$_n$NR$^7$R$^8$, —NR$^7$R$^8$ and —R$^{10}$NR$^7$R$^8$. Yet another class of compounds include those defined wherein R$^2$ does not contain a heterocyclic or heteroaryl moiety but may contain an aryl moiety. In such embodiments, R$^2$ is preferably selected from the group consisting of halo, alkyl, cycloalkyl, alkenyl, cycloalkenyl, Ay, —OR$^7$, —OAy, —S(O)$_n$R$^9$, —S(O)$_n$Ay, —S(O)$_n$NR$^7$R$^8$, —NR$^7$R$^8$, —NHR$^{10}$Ay, —R$^{10}$NR$^7$R$^8$ and —R$^{10}$NR$^7$Ay;

Preferably, R$^2$ is selected from the group consisting of Ay, Het, —OR$^7$, —OAy, —OHet, —OR$^{10}$Het —S(O)$_n$R$^9$, —S(O)$_n$Ay, —NR$^7$R$^8$, —NHHet, —NHR$^{10}$Het, —R$^{10}$NR$^7$R$^8$ and —R$^{10}$NR$^7$Ay, or any subset thereof. More preferably, R$^2$ is selected from the group consisting of Het, —NR$^7$R$^8$, —NHHet and NHR$^{10}$Het, or any subset thereof. Particularly preferred compounds of formula (I) are defined where $R^2$ is selected from the group consisting of —NR$^7$R$^8$ and Het, or any subset thereof. In one embodiment, $R^2$ is selected from the group consisting of —NR$^7$R$^8$.

In one preferred embodiment, $R^2$ is selected from the group consisting of —NH$_2$, —NH-alkyl, —NH-cycloalkyl, —N(alkyl)(alkyl), Het (e.g., pyrrolidine), —NHHet and —NH-alkyl-Het, or any subset thereof. More preferably, $R^2$ is selected from the group consisting of —NH-alkyl, —NH-cycloalkyl, or any subset thereof.

Specific examples of some preferred $R^2$ groups are selected from the group consisting of —NH$_2$, —NH-methyl, —NH-ethyl, —NH-propyl, —NH-isopropyl, —NH-cyclopropyl, —NH-butyl, —NH-isobutyl, —NH-cyclopentyl, —NH-cyclohexyl, —NH(CH2)$_2$OCH$_3$, and pyrrolidine (e.g., pyrrolidine bonded through N).

Preferably, $R^7$ and $R^8$ are each the same or different and are independently selected from the group consisting of H, alkyl, cycloalkyl, $R^{10}$-cycloalkyl, —R$^{10}$OR$^9$, —R$^{10}$NR$^9$R$^{11}$, —C(O)R$^9$ and R$^{10}$CO$_2$R$^9$, or any subset thereof. More preferably, $R^7$ and $R^8$ are each the same or different and are independently selected from the group consisting of H, alkyl, cycloalkyl and R$^{10}$-cycloalkyl, or any subset thereof. In one embodiment, $R^7$ and $R^8$ are each the same or different and are independently selected from the group consisting of H, alkyl and cycloalkyl, or any subset thereof.

Preferably $R^9$ and $R^{11}$ are each the same or different and are independently selected from the group consisting of H, alkyl, cycloalkyl, and —R$^{10}$-cycloalkyl, or any subset thereof. More preferably, $R^9$ and $R^{11}$ are each the same or different and are independently selected from the group consisting of H and alkyl, or any subset thereof.

Preferably $R^{10}$ is alkyl or cycloalkyl; more preferably alkyl.

In another embodiment, the compounds of formula (I) include those compounds defined where at least one of $R_3$ and $R_4$ contain a heterocyclic or heteroaryl moiety. Another embodiment includes those compounds of formula (I) where neither $R_3$ nor $R_4$ contain a heterocyclic or heteroaryl moiety.

$R^3$ is preferably selected from the group consisting of H, halo, alkyl, —OR$^7$, —CO$_2$R$^7$ and —NR$^7$R$^8$, or any subset thereof. More preferably, $R^3$ is selected from the group consisting of H, halo, alkyl, OR$^7$, and —NR$^7$R$^8$, or any subset thereof. Most preferably $R^3$ is H or alkyl. In one embodiment $R^3$ is H.

$R^4$ is preferably selected from the group consisting of H, halo, alkyl, —OR$^7$, —CO$_2$R$^7$ and —NR$^7$R$^8$, or any subset thereof. More preferably $R^4$ is selected from the group consisting of H, halo, alkyl, OR$^7$, and —NR$^7$R$^8$, or any subset thereof. Most preferably, $R^4$ is H or alkyl. In one embodiment, $R^4$ is H.

Preferably q is 0, 1 or 2. In one embodiment, q is 0. In one preferred embodiment q is 1. In one embodiment, q is 2 and the two $R^5$ groups are bonded to adjacent carbon atoms, and optionally, together with the atoms to which they are bonded, they form a C$_{5-6}$ cycloalkyl or aryl. The phrase "two adjacent $R^5$ groups" refers to two $R^5$ groups, each bonded to adjacent carbon atoms on the phenyl ring. In the embodiment where two adjacent $R^5$ groups together with the atoms to which they are bonded form a cycloalkyl or aryl, q is preferably 2, 3, 4 or 5; more preferably 2.

$R^5$ may be in the ortho, meta or para position.

Another class of compounds of formula (I) includes those compounds defined wherein at least one $R^5$ group contains an aryl, heterocyclic or heteroaryl moiety (preferably a heterocyclic or heteroaryl moiety) and two adjacent $R^5$ groups together with the atoms to which they are bonded do not form a C$_{5-6}$ cycloalkyl or aryl. Another class of compounds of formula (I) includes those compounds defined wherein q is 3, 4 or 5, at least one $R^5$ group contains an aryl, heterocyclic or heteroaryl moiety (preferably a heterocyclic or heteroaryl moiety) and two adjacent $R^5$ groups together with the atoms to which they are bonded do form a C$_{5-6}$ cycloalkyl or aryl. A preferred class of compounds of formula (I) includes those compounds defined where no $R^5$ group contains an aryl, heterocyclic or heteroaryl moiety (or in one embodiment no $R^5$ group contains a heterocyclic or heteroaryl moiety) and two adjacent $R^5$ groups together with the atoms to which they are bonded do not form a C$_{5-6}$ cycloalkyl or aryl. Another class of compounds of formula (I) includes those compounds defined wherein q is 2, 3, 4 or 5, no $R^5$ group contains an aryl, heterocyclic or heteroaryl moiety (or in one embodiment no $R^5$ group contains a heterocyclic or heteroaryl moiety) and two adjacent $R^5$ groups together with the atoms to which they are bonded do form a C$_{5-6}$ cycloalkyl or aryl.

In the embodiments where two adjacent $R^5$ groups together with the atoms to which they are bonded form a cycloalkyl or aryl, each $R^5$ group may be the same or different and is preferrably selected from the group consisting of alkyl, and alkenyl. For example, in one embodiment two adjacent $R^5$ groups are alkyl and together with the atoms to which they are bonded, they form a cycloalkyl group such as:

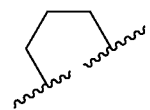

From this example, additional embodiments, including those where two adjacent $R^5$ groups together with the atoms to which they are bonded form an aryl group can be readily ascertained by those skilled in the art Preferably, the compounds of formula (I) are defined wherein two adjacent $R^5$ groups together with the atoms to which they are bonded do not form a C$_{5-6}$ cycloalkyl or aryl.

Preferably, each $R^5$ group is the same or different and is independently selected from the group consisting of halo, alkyl, alkenyl, Ay, Het, —OR$^7$, —CO$_2$R$^9$, —C(O)NR$^7$R$^8$, —S(O)$_2$NR$^7$R, —NR$^7$R$^8$, —NHR$^{10}$Ay, cyano, nitro and azido, or any subset thereof. More preferably, each $R^5$ group is the same or different and is independently selected from the group consisting of halo, alkyl, —OR$^7$, —NR$^7$R$^8$, Ay, Het, cyano and azido, or any subset thereof. Most preferably, each $R^5$ group is the same or different and is independently selected from the group consisting of halo, alkyl, —OR$^7$ and cyano, or any subset thereof.

In particular, preferred embodiments of the compounds of formula (I) are defined where $R^5$ is H, halo (e.g., fluoro, chloro or bromo), alkyl (e.g., methyl), O-alkyl (e.g., O-methyl, O-isobutyl, and

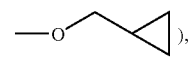), cyano, —NH—CH$_3$, and —N(CH$_3$)$_2$.

p is preferably 1 or 2, more preferably 1.

R[6] may be in the 4, 5 or 6 position. In one embodiment, p is 1 and R[6] is in the C-5 position. In one embodiment, p is 1 and R[6] is in the C-6 position. In one embodiment p is 2 and one R[6] is in the C-5 position and one R[6] is in the C-6 position.

Another class of compounds of formula (I) includes those compounds defined wherein at least one R[6] group contains an aryl, heterocyclic or heteroaryl moiety (preferably a heterocyclic or heteroaryl moiety) and two adjacent R[6] groups together with the atoms to which they are bonded do not form a $C_{5-6}$ cycloalkyl or a 5- or 6-membered heterocyclic group containing 1 or 2 heteroatoms. Another class of compounds of formula (I) includes those compounds defined wherein p is 3, at least one R[6] group contains an aryl, heterocyclic or heteroaryl moiety (preferably a heterocyclic or heteroaryl moiety) and two adjacent R[6] groups together with the atoms to which they are bonded do form a $C_{5-6}$ cycloalkyl or a 5- or 6-membered heterocyclic group containing 1 or 2 heteroatoms. A preferred class of compounds of formula (I) includes those compounds defined where no R[6] group contains an aryl, heterocyclic or heteroaryl moiety (or in one embodiment no R[6] group contains a heterocyclic or heteroaryl moiety) and two adjacent R[6] groups together with the atoms to which they are bonded do not form a $C_{5-6}$ cycloalkyl or a 5- or 6-membered heterocyclic group containing 1 or 2 heteroatoms. Another class of compounds of formula (I) includes those compounds defined wherein p is 2 or 3, no R[6] group contains an aryl, heterocyclic or heteroaryl moiety (or in one embodiment no R[6] group contains a heterocyclic or heteroaryl moiety) and two adjacent R[6] groups together with the atoms to which they are bonded do form a $C_{5-6}$ cycloalkyl or a 5- or 6-membered heterocyclic group containing 1 or 2 heteroatoms.

In the embodiments where two adjacent R[6] groups together with the atoms to which they are bonded form a $C_{5-6}$ cycloalkyl or a 5- or 6-membered heterocyclic group containing 1 or 2 heteroatoms, each R[6] group may be the same or different and is preferrably selected from the group consisting of alkyl, alkenyl, —OR[7], —NR[7]R[8] and —S(O)$_n$R[9]. In one preferred embodiment, when two R[6] groups together with the atoms to which they are bonded form a ring, it is a 5-6 membered heterocyclic group containing at least one N. For example, in one embodiment two adjacent R[6] groups are —NR[7]R[8] and together with the atoms to which they are bonded they form a heterocyclic group such as:

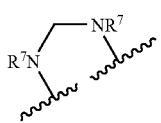

In another embodiment, one R[6] group is —NR[7]R[8] and another is alkyl and together with the atoms to which they are bonded they form a heterocyclic group such as:

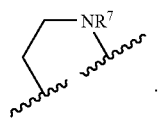

In another embodiment two adjacent R[6] groups are defined as —OR[7], —NR[7]R[8] respectively and together with the atoms to which they are bonded, they form a heterocyclic group such as:

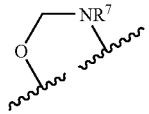

In another embodiment two adjacent R[6] groups are defined as —S(O)$_n$R[9], —NR[7]R[8] respectively and together with the atoms to which they are bonded, they form a heterocyclic group such as:

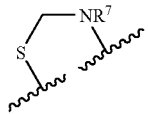

From these examples, additional embodiments can be readily ascertained by those skilled in the art.

In one preferrred embodiment, each R[6] is the same or different and is independently selected from the group consisting of each R[6] is the same or different and is independently selected from the group consisting of halo, alkyl, cycloalkyl, alkenyl, cycloalkenyl, alkynyl, Ay, Het, —OR[7], —OAy, —OHet, —OR[10]Ay, —OR[10]Het, —C(O)R[9], —CO$_2$R[9], —C(O)NR[7]R[8], —C(O)Ay, —C(O)NR[7]Ay, —C(O)NHR[10]Ay, —C(O)Het, —C(O)NHR[10]Het, —C(S)NR[9]R[11], —C(NH)NR[7]R[8], —C(NH)NR[7]Ay, —S(O)$_n$R[9], —S(O)$_n$Ay, —S(O)$_n$Het, —S(O)$_2$NR[7]R[8], —S(O)$_2$NR[7]Ay, —NR[7]R[8], —NR[7]Ay, —NHR[10]Ay, —NHHet, —NHR[10]Het, —R[10]cycloalkyl, —R[10]Ay, —R[10]Het, —R[10]OR[9], —R[10]—O—C(O)R[9], —R[10]—O—C(O)Ay, —R[10]—O—C(O)Het, —R[10]—O—S(O)$_n$R[9], —R[10]NR[7]R[8], —R[10]NR[7]Ay, —R[10]C(O)R[9], —R[10]CO$_2$R[9], —R[10]C(O)NR[9]R[11], —R[10]C(S)NR[9]R[11], —R[10]NHC(NH)NR[9]R[11], —R[10]C(NH)NR[9]R[11], —R[10]SO$_2$R[9], —R[10]SO$_2$NHCOR[9], —R[10]SO$_2$NR[9]R[11], cyano, nitro and azido. That is, preferably the compounds of formula (I) are defined wherein two adjacent R[6] groups together with the atoms to which they are bonded do not form a $C_{5-6}$ cycloalkyl or a 5- or 6-member heterocyclic group containing 1 or 2 heteroatoms.

Preferably, each R[6] is the same or different and is independently selected from the group consisting of halo, alkyl, Ay, Het, —OR[7], —OAy, —OHet, —CO$_2$R[9], —C(O)NR[7]R[8], —C(O)NR[7]Ay, —NR[7]R[8], —NR[7]Ay, —NHR[10]Ay, —NHHet, —NHR[10]Het and cyano, or any subset thereof; wherein at least one R[6] is selected from the group consisting of —NR[7]R[8], —NR[7]Ay, —NHHet, —NHR[10]Ay and —NHR[10]Het. More preferably, each R[6] is the same or different and is independently selected from the group consisting of halo, alkyl, —C(O)NR[7]R[8], —NR[7]R[8], —NHHet, —NHR[10]Ay, —NHR[10]Het and cyano, or any subset thereof; wherein at least one R[6] is selected from the group consisting of —NR[7]R[8], —NR[7]Ay, —NHHet, —NHR[10]Ay and —NHR[10]Het. Most preferably each R[6] is the same or different and is independently selected from the group consisting of halo, —NR[7]R[8], —NR[7]Ay, —NHHet, —NHR[10]Ay and —NHR[10]Het, or any subset thereof;

wherein at least one $R^6$ is selected from the group consisting of —$NR^7R^8$, —$NR^7Ay$, —NHHet, —$NHR^{10}Ay$ and —$NHR^{10}$Het.

In one preferred embodiment, at least one $R^6$ is selected from the group consisting of —$NR^7R^8$ and —NHHet; more preferably at least one $R^6$ is —$NR^7R^8$.

More specific examples of preferred $R^6$ groups include but are not limited to —$NH_2$, —NHalkyl, —$NHR^{10}OR^9$, —NH-cycloalkyl, and —NH—$SO_2$-alkyl. In one preferred embodiment, $R^6$ is selected from the group consisting of —$NH_2$, —$NHCH(CH_3)_2$, —NH-cyclopropyl, —NH-cyclopentyl, —$NH(CH_2)_2$—O—$CH_3$, and —NH—$SO_2$—$CH_3$.

It is to be understood that the present invention includes all combinations and subsets of the particular and preferred groups defined hereinabove.

Preferred compounds of formula (I) include but are not limited to:

N-Cyclopentyl-3-[2-(cyclopentylamino)-4-pyrimidinyl]-2-(4-fluorophenyl)pyrazolo[1,5-α]pyridin-5-amine;

3-[2-(Cyclopentylamino)-4-pyrimidinyl]-2-(4-fluorophenyl)pyrazolo[1,5-α]pyridin-5-amine;

N-[3-[2-(Cyclopentylamino)-4-pyrimidinyl]-2-(4-fluorophenyl)pyrazolo[1,5-α]pyridin-5-yl]methanesulfonamide;

3-[2-(cyclopentylamino)-4-pyrimidinyl]-2-(4-fluorophenyl) pyrazolo[1,5-α]pyridin-6-amine;

N-Cyclopentyl-3-[2-(cyclopentylamino)-4-pyrimidinyl]-2-(4-fluorophenyl)pyrazolo[1,5-α]pyridin-6-amine;

3-[2-(Cyclopentylamino)-4-pyrimidinyl]-2-(4-fluorophenyl)-N-isopropylpyrazolo[1,5-α]pyridin-6-amine;

3-[2-(Cyclopentylamino)-4-pyrimidinyl]-2-(4-fluorophenyl)-N-(2-methoxyethyl)pyrazolo[1,5-α]pyridin-5-amine;

3-[2-(Cyclopentylamino)-4-pyrimidinyl]-2-(4-fluorophenyl)-N-isopropylpyrazolo[1,5-α]pyridin-5-amine;

N-Cyclopentyl-3-[2-(cyclopentylamino)-4-pyrimidinyl]2-(4-methoxyphenyl)-pyrazolo[1,5-α]pyridin-5-amine; and 3-[2-(Cyclopentylamino)-4-pyrimidinyl]-N-isopropyl-2-(4-methoxyphenyl)pyrazolo[1,5-α]pyridin-5-amine;

4-Bromo-N-cyclopentyl-3-[2-(cyclopentylamino)pyrimidin-4-yl]-2-(4-fluorophenyl)pyrazolo[1,5-α]pyridin-5-amine;

4-Chloro-N-cyclopentyl-3-[2-(cyclopentylamino)pyrimidin-4-yl]-2-(4-fluorophenyl)pyrazolo[1,5-α]pyridin-5-amine;

4-Bromo-N-cyclopentyl-3-[2-(cyclopentylamino)pyrimidin-4-yl]-2-(4-methoxyphenyl)pyrazolo[1,5-α]pyridin-5-amine;

4-Chloro-N-cyclopentyl-3-[2-(cyclopentylamino)pyrimidin-4-yl]-2-(4-methoxyphenyl)pyrazolo[1,5-α]pyridin-5-amine;

N-Butyl-3-[2-(butylamino)pyridin-4-yl]-2-(4-fluorophenyl) pyrazolo-[1,5-α]pyridin-4-amine;

4-{5-(Cyclopentylamino)-3-[2-(cyclopentylamino)-4-pyrimidinyl]pyrazolo[1,5-α]pyridin-2-yl}phenol;

N-Cyclopentyl-3-[2-(cyclopentylamino)-4-pyrimidinyl]-2-(4-isobutoxyphenyl)pyrazolo[1,5-α]pyridin-5-amine; and N-Cyclopentyl-3-[2-(cyclopentylamino)-4-pyrimidinyl]-2-[4-(cyclopropylmethoxy)phenyl]pyrazolo[1,5-α]pyridin-5-amine;

pharmaceutically acceptable salts, solvates and physiologically functional derivatives thereof.

Particularly preferred compounds of formula (I) include but are not limited to:

N-Cyclopentyl-3-[2-(cyclopentylamino)-4-pyrimidinyl]-2-(4-fluorophenyl)-pyrazolo[1,5-α]pyridin-5-amine;

3-[2-(cyclopentylamino)-4-pyrimidinyl]-2-(4-fluorophenyl) pyrazolo[1,5-α]pyridin-6-amine;

N-Cyclopentyl-3-[2-(cyclopentylamino)-4-pyrimidinyl]-2-(4-methoxyphenyl)pyrazolo-[1,5-α]pyridin-5-amine;

3-[2-(Cyclopentylamino)-4-pyrimidinyl]-N-isopropyl-2-(4-methoxyphenyl)pyrazolo-[1,5-α]pyridin-5-amine;

N-Cyclopentyl-3-[2-(cyclopentylamino)-4-pyrimidinyl]-2-(4-isobutoxyphenyl)pyrazolo[1,5-α]pyridin-5-amine; and N-Cyclopentyl-3-[2-(cyclopentylamino)-4-pyrimidinyl]-2-[4-(cyclopropylmethoxy)phenyl]pyrazolo[1,5-α]pyridin-5-amine; and pharmaceutically acceptable salts, solvates and physiologically functional derivatives thereof.

It will be appreciated by those skilled in the art that the compounds of the present invention may also be utilized in the form of a pharmaceutically acceptable salt or solvate thereof. The pharmaceutically acceptable salts of the compounds of formula (I) include conventional salts formed from pharmaceutically acceptable inorganic or organic acids or bases as well as quaternary ammonium salts. More specific examples of suitable acid salts include hydrochloric, hydrobromic, sulfuric, phosphoric, nitric, perchloric, fumaric, acetic, propionic, succinic, glycolic, formic, lactic, maleic, tartaric, citric, palmoic, malonic, hydroxymaleic, phenylacetic, glutamic, benzoic, salicylic, fumaric, toluenesulfonic, methanesulfonic, naphthalene-2-sulfonic, benzenesulfonic hydroxynaphthoic, hydroiodic, malic, steroic, tannic and the like. Other acids such as oxalic, while not in themselves pharmaceutically acceptable, may be useful in the preparation of salts useful as intermediates in obtaining the compounds of the invention and their pharmaceutically acceptable salts. More specific examples of suitable basic salts include sodium, lithium, potassium, magnesium, aluminium, calcium, zinc, N,N'-dibenzylethylenediamine, chloroprocaine, choline, diethanolamine, ethylenediamine, N-methylglucamine and procaine salts.

The term "solvate" as used herein refers to a complex of variable stoichiometry formed by a solute (a compound of formula (I)) and a solvent. Solvents, by way of example, include water, methanol, ethanol, or acetic acid.

The term "physiologically functional derivative" as used herein refers to any pharmaceutically acceptable derivative of a compound of the present invention, for example, an ester or an amide of a compound of formula (I), which upon administration to an animal, particularly a mammal, such as a human, is capable of providing (directly or indirectly) a compound of the present invention or an active metabolite thereof. See, for example, Burger's Medicinal Chemistry And Drug Discovery, 5th Edition, Vol 1: Principles And Practice.

Processes for preparing pharmaceutically acceptable salts, solvates and physiologically functional derivatives of the compounds of formula (I) are conventional in the art. See, e.g., Burger's Medicinal Chemistry And Drug Discovery 5th Edition, Vol 1: Principles And Practice.

As will be apparent to those skilled in the art, in the processes descibed below for the preparation of compounds of formula (I), certain intermediates, may be in the form of pharmaceutically acceptable salts, solvates or physiologically functional derivatives of the compound. Those terms as applied to any intermediate employed in the process of preparing compounds of formula (I) have the same meanings as noted above with respect to compounds of formula (I). Processes for preparing pharmaceutically acceptable salts, solvates and physiologically functional derivatives of such intermediates are known in the art and are analogous to the process for preparing pharmaceutically acceptable salts, solvates and physiologically functional derivatives of the compounds of formula (I).

Certain compounds of formula (I) may exist in stereoisomeric forms (e.g. they may contain one or more asymmetric carbon atoms or may exhibit cis-trans isomerism). The individual stereoisomers (enantiomers and diastereomers) and mixtures of these are included within the scope of the present invention. The present invention also covers the individual isomers of the compounds represented by formula (I) as mixtures with isomers thereof in which one or more chiral centres are inverted. Likewise, it is understood that compounds of formula (I) may exist in tautomeric forms other than that shown in the formula and these are also included within the scope of the present invention.

The present invention further provides compounds of formula (I) for use in medical therapy, e.g. in the treatment or prophylaxis, including suppression of recurrence of symptoms, of a viral disease in an animal, e.g. a mammal such as a human. The compounds of formula (I) are especially useful for the treatment or prophylaxis of viral diseases such as herpes viral infections. Herpes viral infections include, for example, herpes simplex virus 1 (HSV-1), herpes simplex virus 2 (HSV-2), cytomegalovirus (CMV), Epstein Barr virus (EBV), Varicella zoster virus (VZV), human herpes virus 6 (HHV-6), human herpes virus 7 (HHV-7), and human herpes virus 8 (HHV-8). Thus, the compounds of the invention are also useful in the treatment or prophylaxis of the symptoms or effects of herpes virus infections.

The compounds of the invention are useful in the treatment or prophylaxis of conditions or diseases associated with herpes virus infections, particularly conditions or diseases associated with latent herpes virus infections in an animal, e.g., a mammal such as a human. By conditions or diseases associated with herpes viral infections is meant a condition or disease, excluding the viral infection per se, which results from the presence of the viral infection, such as chronic fatigue syndrome which is associated with EBV infection; multiple sclerosis which has been associated with herpes viral infections such as EBV and HHV-6, which have been associated with HSV-1 infection. Further examples of such conditions or diseases are described in the background section above.

In addition to those conditions and diseases, the compounds of the present invention may also be used for the treatment or prophylaxis of cardiovascular diseases and conditions associated with herpes virus infections, in particular atherosclerosis, coronary artery disease and restenosis and specifically restenosis following angioplasty (RFA). Restenosis is the narrowing of the blood vessels which can occur after injury to the vessel wall, for example injury caused by balloon angioplasty or other surgical and/or diagnostic techniques, and is characterized by excessive proliferation of smooth muscle cells in the walls of the blood vessel treated. It is thought that in many patients suffering from RFA, viral infection, particularly by CMV and/or HHV-6 of the patient plays a pivotal role in the proliferation of the smooth muscle cells in the coronary vessel treated. Restenosis can occur following a number of surgical and/or diagnostic techniques, for example, transplant surgery, vein grafting, coronary by-pass grafting and, most commonly following angioplasty.

There is evidence from work done both in vitro and in vivo, indicating that restenosis is a multifactorial process. Several cytokines and growth factors, acting in concert, stimulate the migration and proliferation of vascular smooth muscle cells (SMC) and production of extracellular matrix material, which accumulate to occlude the blood vessel. In addition growth suppressors act to inhibit the proliferation of SMC's and production of extracellular matrix material.

In addition, compounds of formula (I) may be useful in the treatment or prophylaxis of hepatitis B or hepatitis C viruses, human papilloma virus (HPV) and HIV.

Thus, the present invention provides a method for the treatment or prophylaxis of a viral infection in an animal such as a mammal (e.g., a human), particularly a herpes viral infection, which method comprises administering to the animal a therapeutically effective amount of the compound of formula (I).

As used herein, the term "prophylaxis" refers to the complete prevention of infection, the prevention of occurrence of symptoms in an infected subject, the prevention of recurrence of symptoms in an infected subject, or a decrease in severity or frequency of symptoms of viral infection, condition or disease in the subject.

As used herein, the term "treatment" refers to the partial or total elimination of symptoms or decrease in severity of symptoms of viral infection, condition or disease in the subject, or the elimination or decrease of viral presence in the subject As used herein, the term "therapeutically effective amount" means an amount of a compound of formula (I) which is sufficient, in the subject to which it is administered, to treat or prevent the stated disease, condition or infection. For example, a therapeutically effective amount of a compound of formula (I) for the treatment of a herpes virus infection is an amount sufficient to treat the herpes virus infection in the subject.

The present invention also provides a method for the treatment or prophylaxis of conditions or diseases associated with a herpes viral infection in an animal such as a mammal (e.g., a human), which comprises administering to the animal a therapeutically effective amount of the compound of formula (I). In one embodiment, the present invention provides a method for the treatment or prophylaxis of chronic fatigue syndrome and multiple sclerosis in an animal such as a mammal (e.g., a human), which comprises administering to the animal a therapeutically effective amount of a compound of formula (I). The foregoing method is particularly useful for the treatment or prophylaxis of chronic fatigue syndrome and multiple sclerosis associated with latent infection with a herpes virus.

In another embodiment, the present invention provides a method for the treatment or prophylaxis of a cardiovascular condition such as atherosclerosis, coronary artery disease or restenosis (particularly restenosis following surgery such as angioplasty), which comprises administering to the animal a therapeutically effective antiviral amount of the compound of formula (I).

The present invention further provides a method for the treatment or prophylaxis of hepatitis B or hepatitis C viruses in an animal such as a mammal (e.g., a human), which comprises administering to the animal a therapeutically effective amount of the compound of formula (I).

The present invention further provides a method for the treatment or prophylaxis of human papilloma virus in an animal such as a mammal (e.g., a human), which comprises administering to the animal a therapeutically effective amount of the compound of formula (I).

The present invention further provides a method for the treatment or prophylaxis of HIV in an animal such as a mammal (e.g., a human), which comprises administering to the animal a therapeutically effective amount of the compound of formula (I).

The present invention also provides the use of the compound of formula (I) in the preparation of a medicament for the treatment or prophylaxis of a viral infection in an animal such as a mammal (e.g., a human), particularly a herpes viral infection; the use of the comound of formula (I) in the preparation of a medicament for the treatment of conditions or diseases associated with a herpes viral infection; and the use of the compound of formula (I) in the preparation of a medicament for the treatment or prophylaxis of hepatitis B or hepatitis C viruses, human papilloma virus or HIV. In particular, the present invention also provides the use of a compound of formula (I) in the preparation of a medicament for the treatment or prophylaxis of chronic fatigue syndrome or multiple sclerosis. In one embodiment, the present invention provides the use of a compound of formula (I) in the preparation of a medicament for the treatment or prophylaxis of cardiovascular disease, such as restenosis and atherosclerosis.

The compounds of formula (I) are conveniently administered in the form of pharmaceutical compositions. Such compositions may conveniently be presented for use in conventional manner in admixture with one or more physiologically acceptable carriers or diluents.

While it is possible that compounds of the present invention may be therapeutically administered as the raw chemical, it is preferable to present the active ingredient as a pharmaceutical formulation or composition. The pharmaceutical composition may comprise a carrier or diluent. The carrier(s) or diluent(s) must be "acceptable" in the sense of being compatible with the other ingredients of the formulation and not deleterious to the recipient thereof.

Accordingly, the present invention further provides for a pharmaceutical formulation or composition comprising a compound of formula (I). In one embodiment, the pharmaceutical composition further comprises one or more pharmaceutically acceptable carriers or diluents and optionally, other therapeutic and/or prophylactic ingredients.

The formulations include those suitable for oral, parenteral (including subcutaneous e.g. by injection or by depot tablet, intradermal, intrathecal, intramuscular e.g. by depot and intravenous), rectal and topical (including dermal, buccal and sublingual) administration although the most suitable route may depend upon for example the condition, age, and disorder of the recipient as well as the viral infection or disease being treated. The formulations may conveniently be presented in unit dosage form and may be prepared by any of the methods well known in the art of pharmacy. All methods include the step of bringing into association a compound(s) of formula (I) ("active ingredient") with the carrier which constitutes one or more accessory ingredients. In general the formulations are prepared by uniformly and intimately bringing into association the active ingredient with liquid carriers or finely divided solid carriers or both and then, if necessary, shaping the product into the desired formulation.

Formulations suitable for oral administration may be presented as discrete units such as capsules, cachets or tablets (e.g. chewable tablets in particular for paediatric administration) each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or moulding, optionally with one or more accessory ingredients. Compressed tablets may be prepared by compressing in a suitable machine the active ingredient in a free-flowing form such as a powder or granules, optionally mixed with other conventional excipients such as binding agents, (for example, syrup, acacia, gelatin, sorbitol, tragacanth, mucilage of starch or polyvinylpyrrolidone), fillers (for example, lactose, sugar, microcrystalline cellulose, maize-starch, calcium phosphate or sorbitol), lubricants (for example, magnesium stearate, stearic acid, talc, polyethylene glycol or silica), disintegrants (for example, potato starch or sodium starch glycollate) or wetting agents, such as sodium lauryl sulfate. Moulded tablets may be made by moulding in a suitable machine a mixture of the powdered compound moistened with an inert liquid diluent. The tablets may optionally be coated or scored and may be formulated so as to provide slow or controlled release of the active ingredient therein. The tablets may be coated according to methods well-known in the art.

Alternatively, the compounds of the present invention may be incorporated into oral liquid preparations such as aqueous or oily suspensions, solutions, emulsions, syrups or elixirs, for example. Moreover, formulations containing these compounds may be presented as a dry product for constitution with water or other suitable vehicle before use. Such liquid preparations may contain conventional additives such as suspending agents such as sorbitol syrup, methyl cellulose, glucose/sugar syrup, gelatin, hydroxyethylcellulose, carboxymethyl cellulose, aluminum stearate gel or hydrogenated edible fats; emulsifying agents such as lecithin, sorbitan mono-oleate or acacia; non-aqueous vehicles (which may include edible oils) such as almond oil, fractionated coconut oil, oily esters, propylene glycol or ethyl alcohol; and preservatives such as methyl or propyl p-hydroxybenzoates or sorbic acid. Such preparations may also be formulated as suppositories, e.g., containing conventional suppository bases such as cocoa butter or other glycerides.

Formulations for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

The formulations may be presented in unit-dose or multi-dose containers, for example sealed ampoules and vials, and may be stored in a freeze-dried (lyophilised) condition requiring only the addition of a sterile liquid carrier, for example, water-for-injection, immediately prior to use. Extemporaneous injection solutions and suspensions may be prepared from sterile powders, granules and tablets of the kind previously described.

Formulations for rectal administration may be presented as a suppository with the usual carriers such as cocoa butter, hard fat or polyethylene glycol. Formulations suitable for topical or intranasal application include ointments, creams, lotions, pastes, gels, sprays, aerosols and oils. Suitable carriers for such formulations include petroleum jelly, lanolin, polyethyleneglycols, alcohols, and combinations thereof.

Formulations for topical administration in the mouth, for example buccally or sublingually, include lozenges comprising the active ingredient in a flavoured base such as sucrose and acacia or tragacanth, and pastilles comprising the active ingredient in a base such as gelatin and glycerin or sucrose and acacia.

The compounds may also be formulated as depot preparations. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

In addition to the ingredients particularly mentioned above, the formulations may include other agents conventional in the art having regard to the type of formulation in question, for example those suitable for oral administration may include flavouring agents.

It will be appreciated that the amount of a compound of the invention required for use in treatment will vary with the nature of the condition being treated and the age and the condition of the patient and will be ultimately at the discretion of the attendant physician or veterinarian. In general, however, doses employed for adult human treatment will typically be in the range of 0.02–5000 mg per day, preferably 100–1500 mg per day. The desired dose may conveniently be presented in a single dose or as divided doses administered at appropriate intervals, for example as two, three, four or more sub-doses per day. The formulations according to the invention may contain between 0.1–99% of the active ingredient, conveniently from 30–95% for tablets and capsules and 3–50% for liquid preparations.

The compound of formula (I) for use in the instant invention may be used in combination with other therapeutic agents for example, non-nucleotide reverse transcriptase inhibitors, nucleoside reverse transcriptase inhibitors, protease inhibitors and/or other antiviral agents. The invention thus provides in a further aspect the use of a combination comprising a compound of formula (I) with a further therapeutic agent in the treatment of viral infections. Particular antiviral agents which may be combined with the compounds of the present invention include aciclovir, valaciclovir, famcyclovir, gancyclovir, docosanol, miribavir, amprenavir, lamivudine, zidovudine, and abacavir. Preferred antiviral agents for combining with the compounds of the present invention include aciclovir and valaciclovir. Thus the present invention provides in a further aspect, a combination comprising a compound of formula (I) and an antiviral agent selected from the group consisting of aciclovir and valaciclovir; the use of such combination in the treatment of viral infections and the preparation of a medicament for the treatment fo viral infections, and a method of treating viral infections comprising administering a compound of formula (I) and an antiviral agent selected from the group consisting of aciclovir and valaciclovir.

When a compound of formula (I) is used in combination with other therapeutic agents, the compounds may be administered either sequentially or simultaneously by any convenient route.

The combinations referred to above may conveniently be presented for use in the form of a pharmaceutical formulation and thus pharmaceutical formulations comprising a combination as defined above optionally together with a pharmaceutically acceptable carrier or diluent comprise a further aspect of the invention. The Individual components of such combinations may be administered either sequentially or simultaneously in separate or combined pharmaceutical formulations. When combined in the same formulation it will be appreciated that the two compounds must be stable and compatible with each other and the other components of the formulation and may be formulated for administration. When formulated separately they may be provided in any convenient formulation, in such a manner as are known for such compounds in the art.

When a compound of formula (I) is used in combination with a second therapeutic agent active against the viral infection, the dose of each compound may differ from that when the compound is used alone. Appropriate doses will be readily appreciated by those skilled in the art.

Compounds of formula (I) wherein Y is N, $R^2$ is selected from the group consisting of alkyl, cycloalkyl, alkenyl, cycloalkenyl, Ay, Het, —$OR^7$, —OAy, —OHet, —$OR^{10}$Het —$S(O)_nR^9$, —$S(O)_n$Ay, —$S(O)_n$Het, —$S(O)_nNR^7R^8$, —$NR^7R^8$, —NHHet, —$NHR^{10}$Het, —$NHR^{10}$Ay, —$R^{10}NR^7R^8$ and —$R^{10}NR^7$Ay; $R^3$ and $R^4$ are H; and at least one $R^6$ is selected from the group consisting of —$NR^7R^8$, —$NR^7$Ay, —NHHet, —$NHR^{10}$Ay, and —$NHR^{10}$Het, may be conveniently prepared by the process outlined in Scheme 1 below.

Scheme 1

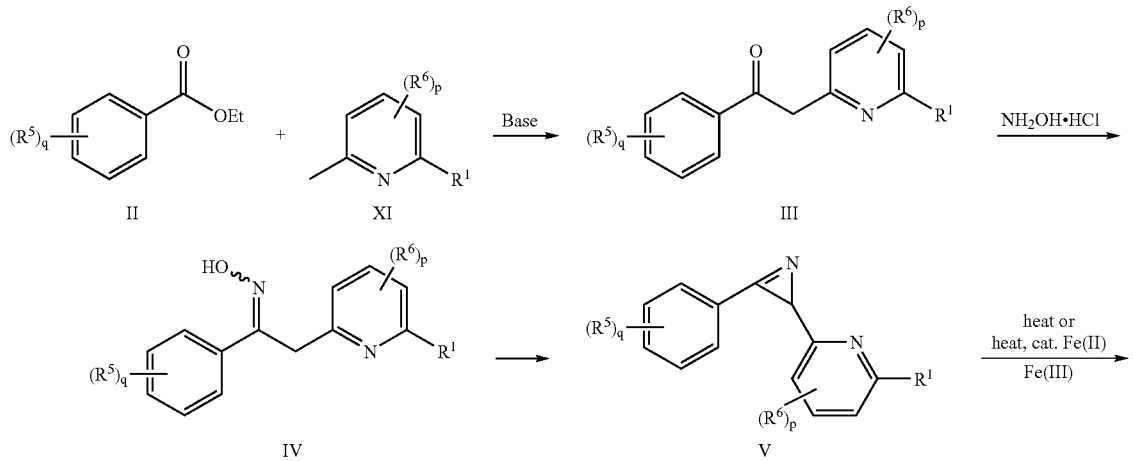

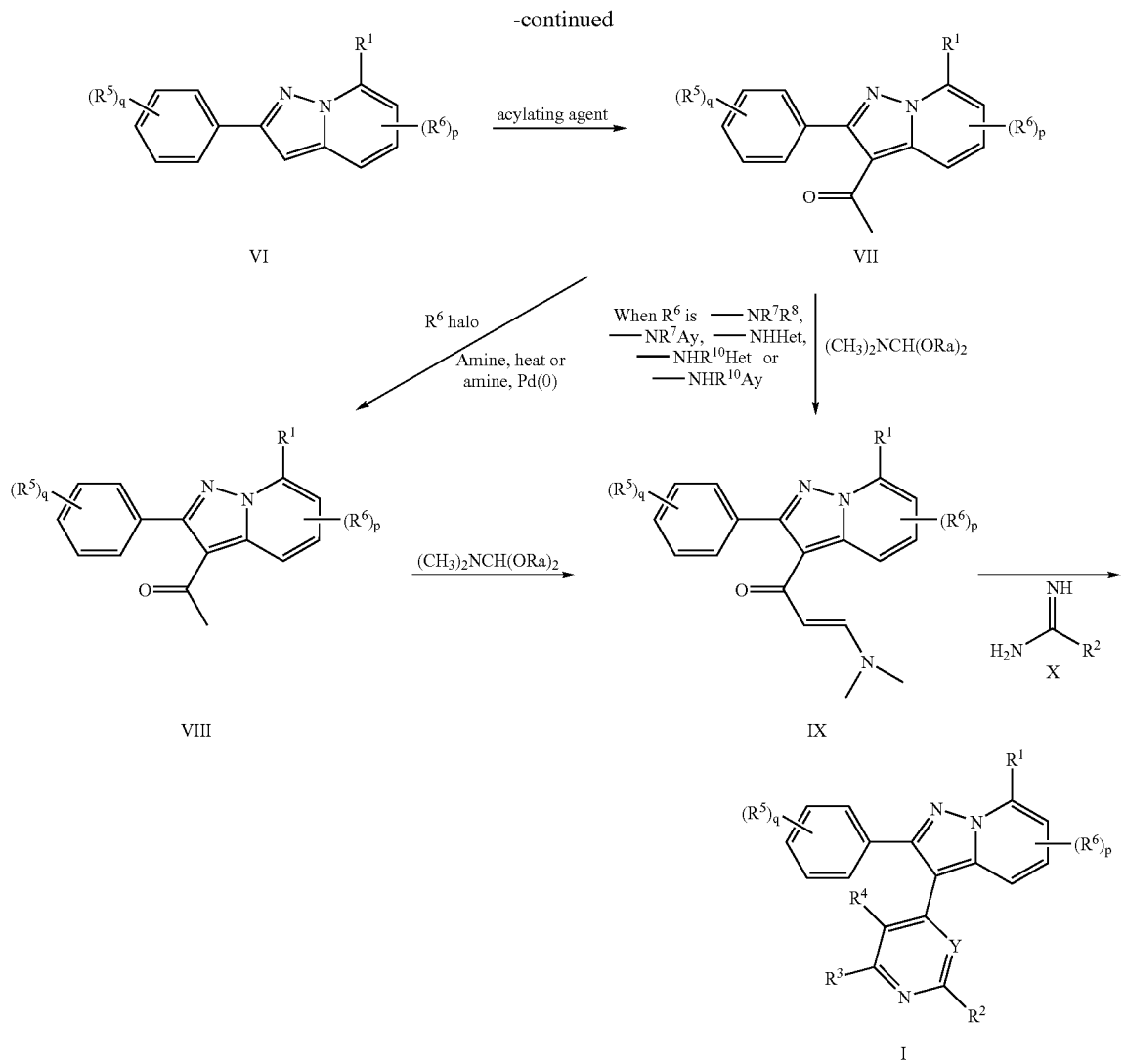

wherein:

R¹ is H;

R² is selected from the group consisting of alkyl, cycloalkyl, alkenyl, cycloalkenyl, Ay, Het, —OR⁷, —OAy, —OHet, —OR¹⁰Het, —S(O)$_n$R⁹, —S(O)$_n$Ay, —S(O)$_n$Het, —S(O)$_n$NR⁷R⁸, —NHR⁷R⁸, —NHHet, —NHR¹⁰Het, —NHR¹⁰Ay, —R¹⁰NR⁷R⁸ and —R¹⁰NR⁷Ay;

each R⁷ and R⁸ are the same or different and are independently selected from the group consisting of H, alkyl, cycloalkyl, alkenyl, cycloalkenyl, —OR⁹, —C(O)R⁹, —CO₂R⁹, —C(O)NR⁹R¹¹, —C(S)NR⁹R¹¹, —C(NH)NR⁹R¹¹, —SO₂R¹⁰, —SO₂NR⁹R¹¹, —R¹⁰cycloalkyl, —R¹⁰OR⁹, —R¹⁰NR⁹R¹¹, —R¹⁰C(O)R⁹, —R¹⁰CO₂R⁹, —R¹⁰C(O)NR⁹R¹¹, —R¹⁰C(S)NR⁹R¹¹, —R¹⁰NHC(NH)NR⁹R¹¹, —R¹⁰C(NH)NR⁹R¹¹, —R¹⁰SO₂R¹⁰, —R¹⁰SO₂NR⁹R¹¹, —R¹⁰NHSO₂R⁹, —R¹⁰NHCOR⁹ and —R¹⁰SO₂NHCOR⁹;

each R⁹ and R¹¹ are the same or different and are independently selected from the group consisting of H, alkyl, cycloalkyl, —R¹⁰cycloalkyl, —R¹⁰OH, —R¹⁰(OR¹⁰)$_w$ where w is 1–10, and —R¹⁰NR¹⁰R¹⁰;

each R¹⁰ is the same or different and is independently selected from the group consisting of alkyl, cycloalkyl, alkenyl, cycloalkenyl and alkynyl;

n is 0, 1 or 2;

Ay is aryl;

Het is a 5- or 6-membered heterocyclic or heteroaryl group;

Y is N;

R³ and R⁴ are both H;

q is 0, 1, 2, 3, 4 or 5;

each R⁵ is the same or different and is independently selected from the group consisting of halo, alkyl, cycloalkyl, alkenyl, cycloalkenyl, alkynyl, Ay, Het, —OR⁷, —OAy, —OHet, —C(O)R⁹, —CO₂R⁹, —C(O)NR⁷R⁸, —C(O)Ay, —C(O)NR⁷Ay, —C(O)Het, —C(O)NHR¹⁰Het, —C(S)NR⁹R¹¹, —C(NH)NR⁷R⁸, —C(NH)NR⁷Ay, —S(O)$_n$R⁹, —S(O)₂NR⁷R⁸, —S(O)₂NR⁷Ay, —NR⁷R⁸, —NR⁷Ay, —NHHet, —NHR¹⁰Ay, —NHR¹⁰Het, —R¹⁰cycloalkyl, —R¹⁰OR⁹, —R¹⁰NR⁷R⁸, —R¹⁰NR⁷Ay, —R¹⁰C(O)R⁹, —R¹⁰CO₂R⁹, —R¹⁰C(O)NR⁹R¹¹, —R¹⁰C(S)NR⁹R¹¹, —R¹⁰NHC(NH)NR⁹R¹¹, —R¹⁰C(NH)

$NR^9R^{11}$, —$R^{10}SO_2R^9$, —$R^{10}SO_2NHCOR^9$, —$R^{10}SO_2NR^9R^{11}$, cyano, nitro and azido; or two adjacent $R^5$ groups together with the atoms to which they are bonded form a $C_{5-6}$ cycloalkyl or aryl;

p is 1, 2 or 3; and each $R^6$ is the same or different and is independently selected from the group consisting of halo, alkyl, cycloalkyl, alkenyl, cycloalkenyl, alkynyl, Ay, Het, —$OR^7$, —OAy, —OHet, —$OR^{10}$Ay, —$OR^{10}$Het, —$C(O)R^9$, —$CO_2R^9$, —$C(O)NR^7R^8$, —C(O)Ay, —$C(O)NR^7$Ay, —C(O)NHR$^{10}$Ay, —C(O)Het, —$C(O)NHR^{10}$Het, —$C(S)NR^9R^{11}$, —$C(NH)NR^7R^8$, —$C(NH)NR^7$Ay, —$S(O)_nR^9$, —$S(O)_n$Ay, —$S(O)_n$Het, —$S(O)_2NR^7R^8$, —$S(O)_2NR^7$Ay, —$NR^7R^8$, —$NR^7$Ay, —NHR$^{10}$Ay, —NHHet, —NHR$^{10}$Het, —$R^{10}$cycloalkyl, —$R^{10}$Ay, —$R^{10}$Het, —$R^{10}OR^9$, —$R^{10}$—O—$C(O)R^9$, —$R^{10}$—O—C(O)Ay, —$R^{10}$—O—C(O)Het, —$R^{10}$—O—$S(O)_nR^9$, —$R^{10}NR^7R^8$, —$R^{10}NR^7$Ay, —$R^{10}C(O)R^9$, —$R^{10}CO_2R^9$, —$R^{10}C(O)NR^9R^{11}$, —$R^{10}C(S)NR^9R^{11}$, —$R^{10}NHC(NH)NR^9R^{11}$, —$R^{10}C(NH)NR^9R^{11}$, —$R^{10}SO_2R^9$, —$R^{10}SO_2NHCOR^9$, —$R^{10}SO_2NR^9R^{11}$, cyano, nitro and azido; or two adjacent $R^6$ groups together with the atoms to which they are bonded form a $C_{5-6}$cycloalkyl or a 5- or 6-membered heterocyclic group containing 1 or 2 heteroatoms;

wherein at least one $R^6$ is selected from the group consisting of —$NR^7R^8$, —$NR^7$Ay, —NHHet, —NHR$^{10}$Ay and —NHR$^{10}$Het; and wherein in the compounds of formulas (VIII), (IX) and (I), at least one $R^6$ is selected from the group consisting of —$NR^7R^8$, —$NR^7$Ay, —NHHet, —NHR$^{10}$Ay and —NHR$^{10}$Het; and Ra is alkyl or cycloalkyl.

Generally, the process for preparing the compounds of formula (I) wherein Y is N, $R^2$ is selected from the group consisting of alkyl, cycloalkyl, alkenyl, cycloalkenyl, Ay, Het, —$OR^7$, —OAy, —OHet, —$OR^{10}$Het —$S(O)_nR^9$, —S(O)Ay, —$S(O)_n$Het, —$S(O)_nNR^7R^8$, —$NR^7R^8$. —NHHet, —NHR$^{10}$Het, —NHR$^{10}$Ay, —$R^{10}NR^7R^8$ and —$R^{10}NR^7$Ay; and $R^3$ and $R^4$ are H; and at least one $R^6$ is selected from the group consisting of —$NR^7R^8$, —$NR^7$Ay, —NHHet, —NHR$^{10}$Ay and —NHR$^{10}$Het, (all formulas and all other variables having been defined above in connection with Scheme 1) comprises the steps of:

(a) reacting a picoline of formula (XI) with a benzoylating agent of formula (II) to prepare a compound of formula (III);

(b) reacting the compound of formula (III) with a hydroxylamine source to prepare a compound of formula (IV);

(c) reacting the compound of formula (IV) with an acylating or sulfonylating agent to prepare a compound of formula (V);

(d) rearranging the compound of formula (V) to prepare a compound of formula (VI);

(e) acylating the compound of formula (VI) to prepare a compound of formula (VII);

(f) in the embodiment wherein no $R^6$ in the compound of formula (VII) is selected from the group consisting of —$NR^7R^8$, —$NR^7$Ay, —NHHet, —NHR$^{10}$Ay and —NHR$^{10}$Het (i.e., said at least on $R^6$ is halo; herein "$R^6$ halo") replacing the $R^6$ halo of the compound of formula (VII) with an amine substituent selected from the group consisting of —$NR^7R^8$, —$NR^7$Ay, —NHHet, —NHR$^{10}$Ay and —NHR$^{10}$Het to prepare a compound of formula (VIII);

(g) reacting the compound of formula (VIII) with a dimethylformamide dialkyl acetal of formula $(CH_3)_2NCH(ORa)_2$ to prepare a compound of formula (IX); and (h) reacting the compound of formula (IX) with a compound of formula (X) to prepare a compound of formula (I).

More specifically, compounds of formula (I) wherein Y is N, $R^2$ is selected from the group consisting of alkyl, cycloalkyl, alkenyl, cycloalkenyl, Ay, Het, —$OR^7$, —OAy, —OHet, —$OR^{10}$Het —$S(O)_nR^9$, —$S(O)_n$Ay, —$S(O)_n$Het, —$S(O)_nNR^7R^8$, —$NR^7R^8$, —NHHet, —NHR$^{10}$Het, —NHR$^{10}$Ay, —$R^{10}NR^7R^8$ and —$R^{10}NR^7$Ay; $R^3$ and $R^4$ are H, and at least one $R^6$ is selected from the group consisting of halo, —$NR^7R^8$, —$NR^7$Ay, —NHHet, —NHR$^{10}$Ay and —NHR$^{10}$Het can be prepared by reacting a compound of formula (IX) with a compound of formula (X).

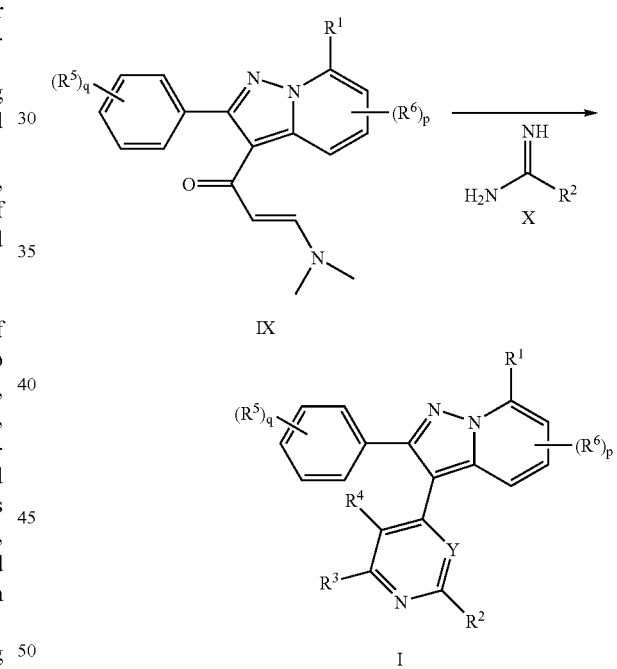

wherein all variables are as defined above in connection with Scheme 1.

This method can be readily carried out by mixing a compound of formula (IX) with a compound of formula (X) in a suitable solvent, optionally in the presence of a base (preferably when the amidine is in a salt form), and heating the reaction to 50–150° C. Typical solvents include lower alcohols such as methanol, ethanol, isopropanol, dimethylformamide, or the like. The base is typically a sodium alkoxide, potassium carbonate, or an amine base such as triethylamine. In one embodiment, the solvent is dimethylformamide and the base is potassium carbonate, or an amine base such as triethylamine.

Compounds of the formula (IX) may be conveniently prepared by reacting a compound of formula (VII) with a dimethylformamide dialkyl acetal of formula $(CH_3)_2NCH(ORa)_2$.

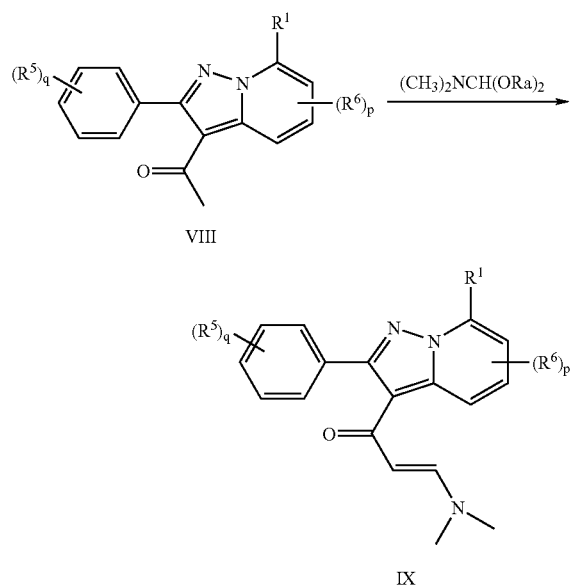

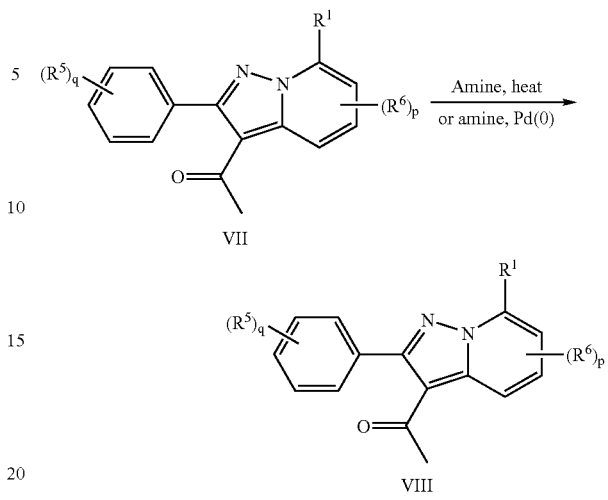

wherein all variables are as defined above in connection with Scheme 1.

Typical dimethylformamide dialkylacetal compounds for use in this method include but are not limited to dimethylformamide dimethylacetal and dimethylformamide di-tert-butylacetal. The reaction is carried out by mixing a compound of formula (VIII) with the dimethylformamide dialkyl acetal, optionally with heating. As one skilled in the art will appreciate, this also encompasses the reaction of a compound of formula (VII) when at least one $R^6$ in the compound of formula (VII) is selected from the group consisting of —$NR^7R^8$, —$NR^7Ay$, —NHHet, —$NHR^{10}Ay$ and —$NHR^{10}$Het. Thus, when the compound of formula (VII) is defined wherein at least one $R^6$ is selected from the group consisting of —$NR^7R^8$, —$NR^7Ay$, —NHHet, —$NHR^{10}Ay$ and —$NHR^{10}$Het, then the following reaction of the compound of formula (VII) with the amine is unnecessary, and the compound of formula (VII) is in fact a compound of formula (VIII) for purposes of preparing a compound of formula (I) pursuant to this method.

In the embodiment, wherein compounds of formula (VII) are defined such that no $R^6$ is —$NR^7R^8$, —$NR^7Ay$, —NHHet, —$NHR^{10}Ay$ or —$NHR^{10}$Het (i.e., the compounds of formula (VII) are defined wherein said at least one $R^6$ is halo; herein "$R^6$ halo") compounds of formula (VIII) may be prepared by replacement of the halogen on the compounds of formula (VII) (i.e., replacement of the $R^6$ halo) with an amine substituent selected from the group consisting of —$NR^7R^8$, —$NR^7Ay$, —NHHet, —$NHR^{10}Ay$ and —$NHR^{10}$Het.

wherein all variables are as defined above in connection with Scheme 1.

Typically the replacement is carried out by mixing the compound of formula (VII) with an amine nucleophile selected from the group consisting of —$NR^7R^8$, —$NR^7Ay$, —NHHet, —$NHR^{10}Ay$ and —$NHR^{10}$Het; and optionally heating the reaction.

Alternatively, the process of converting a compound of formula (VII) to a compound of formula (VIII) is carried out by reacting a compound of formula (VII) with an imine in the presence of a palladium (0) source, a base and a suitable ligand, followed by hydrolysis to give a compound of formula (VIII). See J. Wolfe, et al., *Tetrahedron Letters* 38:6367–6370 (1997). Typically the imine is benzophenoneimine, the palladium (0) source is tris(dibenzylideneacetone)-dipalladium(0), the base is sodium tert-butoxide and the ligand is racemic-2,2'-bis(diphenylphosphino)-1,1'-binaphthyl. Suitable solvents include N,N-dimethylformamide and the like.

The reaction can also be carried out via an adaptation of procedures found in the literature (Wolfe, J. P.; Buchwald, S. L. *J. Org. Chem.* 2000, 65, 1144) wherein a compound of formula (VII) is treated with an amine, a palladium (0) or nickel (0) source and a base in a suitable solvent Suitable sources of palladium (0) include but are not limited to palladium(II) acetate and tris(dibenzylideneacetone) dipalladium (0).

Typical bases for use in the reaction include, for example sodium tert-butoxide and cesium carbonate. Toluene is an example of a suitable solvent.

The instant process for converting the $R^6$ halo substituent in the compounds of formula (VII) to the amine substituent selected from the group consisting of —$NR^7R^8$, —$NR^7Ay$, —NHHet, —$NHR^{10}Ay$ and —$NHR^{10}$Het, is described as occurring toward the end of the synthesis, however, one skilled in the art will readily appreciate that the conversion of the halogen to the amine can occur at earlier stages in the process as well, using the same techniques as are described herein. For example, any of the halogenated intermediates may be converted to the amine analogues prior to proceeding with the next step of the synthesis. This would of course eliminate the need for performing this conversion later. The various permutations of the foregoing synthesis wherein the conversion of the halogen to the amine occurs earlier in the synthesis are contemplated by the instant invention and encompassed within its scope. Thus, the order of the foregoing steps of the synthesis is not critical to obtaining the compounds of formula (I).

Compounds of formula (III) may be conveniently prepared from compounds of the formula (VI) using an acylation procedure.

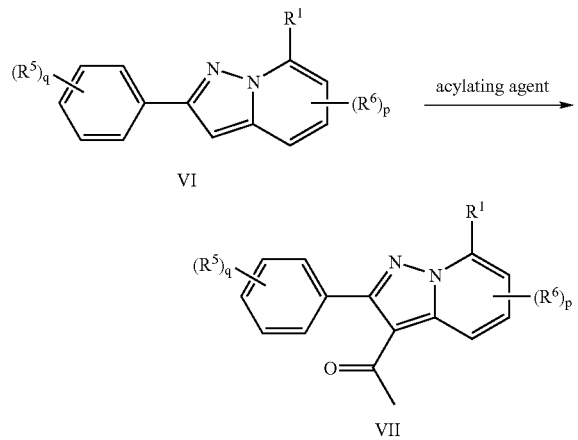

wherein all variables are as defined above in connection with Scheme 1.

Typically the acylation is carried out by treating the compounds of formula (VI) with an acylating agent, optionally in the presence of an acid or Lewis acid catalyst in an inert solvent with optional heating. Typical acylating agents will be readily determined by those skilled in the art. One preferred acylating agent is acetic anhydride. Lewis acid catalysts are also known to those skilled in the art. One preferred Lewis acid catalyst for use in this reaction is boron trifluoride diethyl etherate. A suitable solvent is toluene.

Compounds of formula (VI) are conveniently prepared by rearranging an azirine compound of formula (V).

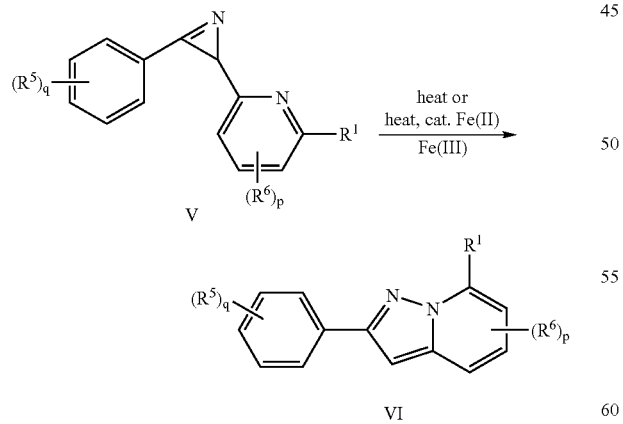

wherein all variables are as defined above in connection with Scheme 1.

The rearrangement of the azirines of formula (V) can be accomplished by heating a solution of the azirine of formula (V) in a suitable solvent at a temperature of about 160–200° C. Suitable inert solvents include, but are not limited to, 1-methyl-2-pyrrolidinone, and 1,2,4-trichlorobenzene. A more preferred method for rearrangement of the azirine of formula (V) to compounds of formula (VI) involves reacting the compound of formula (V) with ferrous chloride ($FeCl_2$) or ferric chloride ($FeCl_3$). See PCT Publication No. WO 01/83479, published 8 Nov. 2001 to GlaxoSmithKline Inc. This reaction is typically done in an inert solvent with heating. A preferred solvent for this reaction is 1,2-dimethoxyethane and the like.

Typically the azirines of formula (V) are prepared from oxime compounds of formula (IV) by treatment with acylating or sulfonylating agents in the presence of a base.

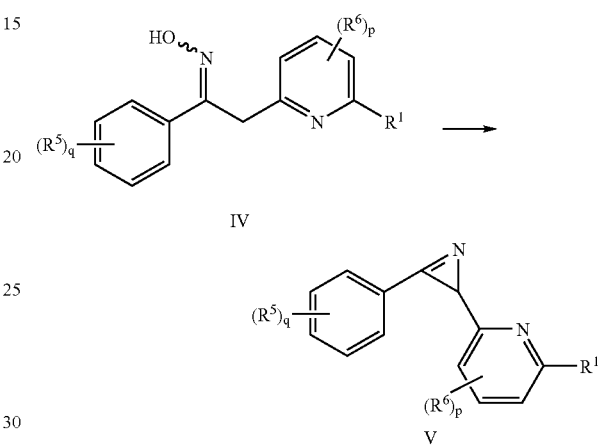

wherein all variables are as defined above in connection with Scheme 1.

Typical acylating or sulfonylating agents include but are not limited to, acetic anhydride, trifluoroacetic anhydride, methanesulfonyl chloride, toluenesulfonyl chloride and the like. Typical bases include, but are not limited to, triethylamine, diisopropylethylamine, pyridine, and the like. The reaction may be carried out in an inert solvent such as for example, chloroform, dichloromethane, toluene or the like.

The oxime compounds of formula (IV) are readily prepared by treating ketone compounds of formula (III) with a hydroxylamine source, in a suitable solvent, and optionally with a base.

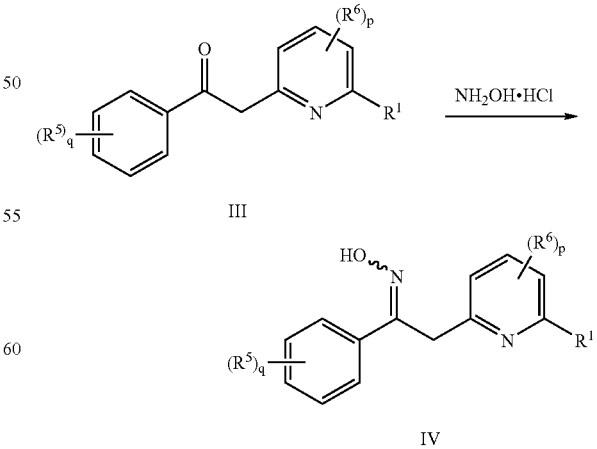

wherein all variables are as defined above in connection with Scheme 1.

Preferably the hydroxylamine is hydroxylamine hydrochloride and the base is an aqueous solution of sodium hydroxide. Suitable solvents include lower alcohols such as methanol, ethanol, or isopropanol.

The ketone compounds of formula (III) can be prepared by treatment of a picoline of formula (XI) with a benzoylating agent of formula (II) in the presence of a base.

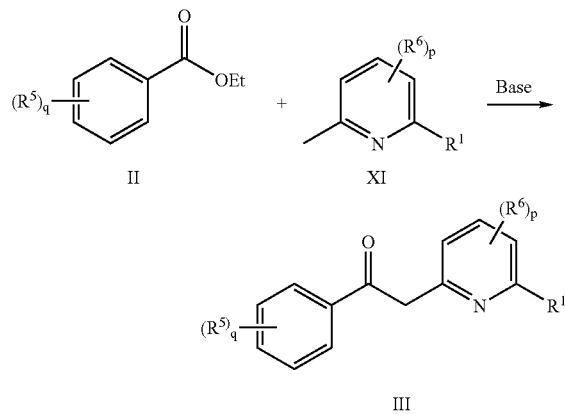

wherein all variables are as defined above in connection with Scheme 1.

Preferred benzoylating agents of formula (II) include, but are not limited to, benzoyl esters. An example of a preferred picoline is a chloropicoline. An example of a suitable base is lithium bis(trimethylsilyl)amide in an inert solvent such as tetrahydrofuran. Ketones such as those of formula (III) can be readily prepared using procedures known to one skilled in the art and/or described in the literature (Cassity, R. P.; Taylor, L. T.; Wolfe, J. F. *J. Org. Chem.* 1978, 2286).

In addition to the foregoing process for preparing certain compounds of formula (I), the present invention also provides certain intermediate compounds for use in the preparation of such compounds of formula (I) according to the foregoing process. Such intermediates are represented in Scheme 1 above.

In a further embodiment of the present invention, compounds of formula (I) wherein Y is N; $R^2$ is selected from the group consisting of alkyl, cycloalkyl, alkenyl, cycloalkenyl, Ay, Het, —$OR^7$, —OAy, —OHet, —$OR^{10}$Het—$S(O)_nR^9$, —$S(O)_n$Ay, —$S(O)_n$Het, —$S(O)_nNR^7R^8$, —$NR^7R^8$, —NH-Het, —$NHR^{10}$Het, —$NHR^{10}$Ay, —$R^{10}NR^7R^8$ and —$R^{10}NR^7$Ay; and $R^3$ and $R^4$ are H, may be conveniently prepared by the process outlined in Scheme 1-A below.

Scheme 1-A

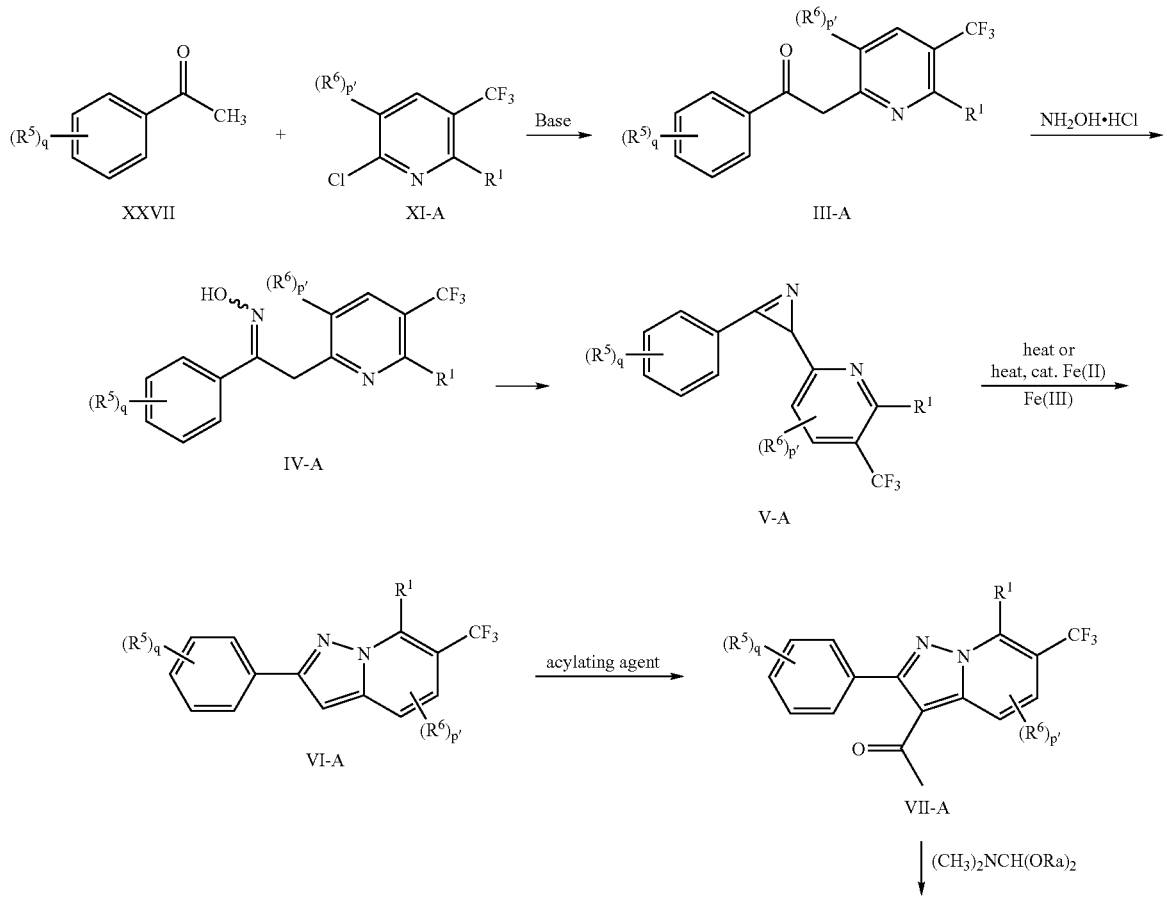

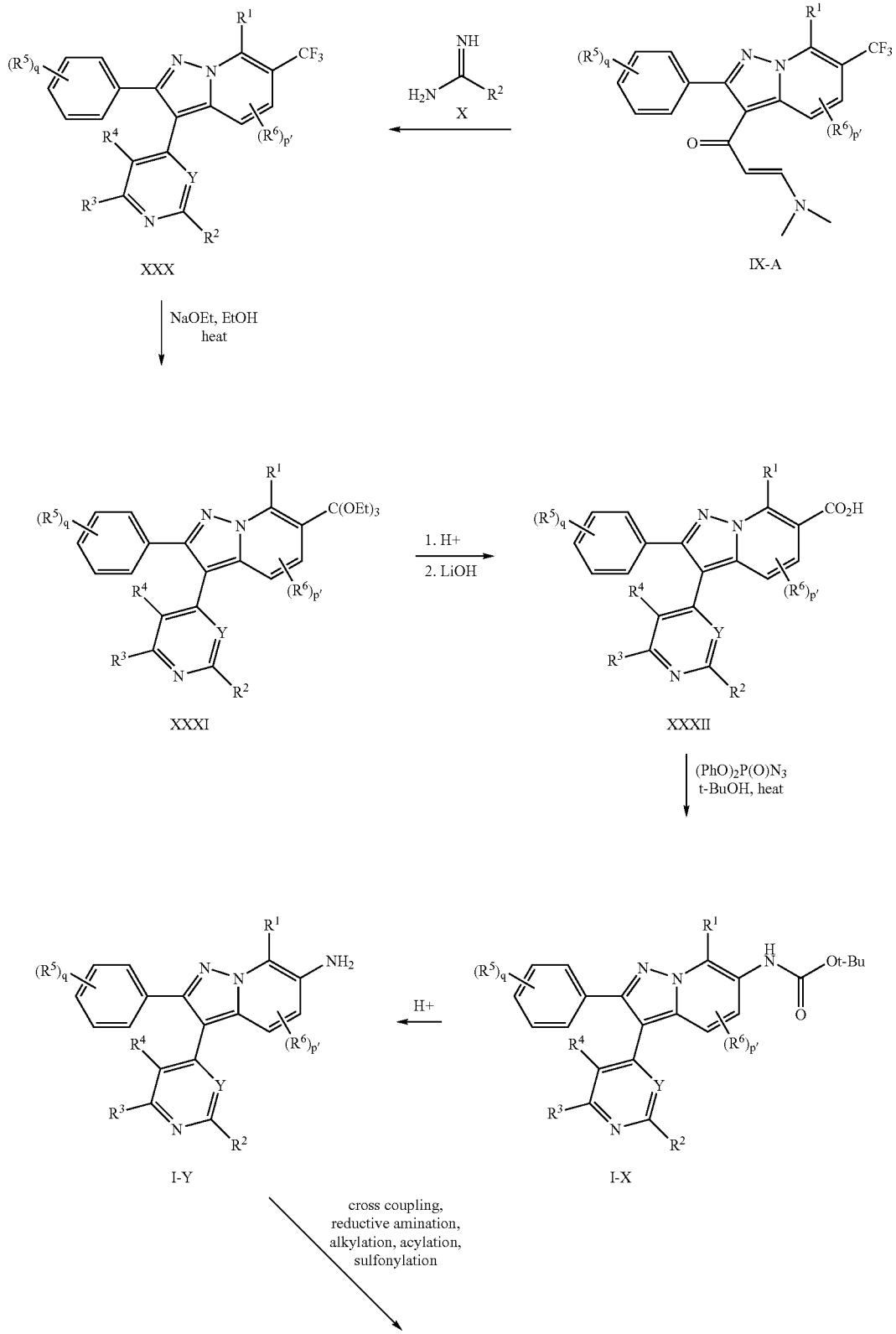

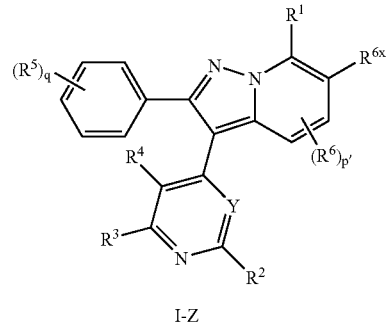

I-Z wherein:
R¹ is H;
R² is selected from the group consisting of alkyl, cycloalkyl, alkenyl, cycloalkenyl, Ay, Het, —OR⁷, —OAy, —OHet, —OR¹⁰Het, —S(O)$_n$R⁹, —S(O)$_n$Ay, —S(O)$_n$Het, —S(O)$_n$NR⁷R⁸, —NR⁷R⁸, —NHHet, —NHR¹⁰Het, —NHR¹⁰Ay, —R¹⁰NR⁷R⁸ and —R¹⁰NR⁷Ay;

each R⁷ and R⁸ are the same or different and are independently selected from the group consisting of H, alkyl, cycloalkyl, alkenyl, cycloalkenyl, —OR⁹, —C(O)R⁹, —CO₂R⁹, —C(O)NR⁹R¹¹, —C(S)NR⁹R¹¹, —C(NH)NR⁹R¹¹, —SO₂R¹⁰, —SO₂NR⁹R¹¹, —R¹⁰cycloalkyl, —R¹⁰OR⁹, —R¹⁰NR⁹R¹¹, —R¹⁰C(O)R⁹, —R¹⁰CO₂R⁹, —R¹⁰C(O)NR⁹R¹¹, —R¹⁰C(S)NR⁹R¹¹, —R¹⁰NHC(NH)NR⁹R¹¹, —R¹⁰C(NH)NR⁹R¹¹, —R¹⁰SO₂R¹⁰, —R¹⁰SO₂NR⁹R¹¹, —R¹⁰NHSO₂R⁹, —R¹⁰NHCOR⁹ and —R¹⁰SO₂NHCOR⁹;

each R⁹ and R¹¹ are the same or different and are independently selected from the group consisting of H, alkyl, cycloalkyl, —R¹⁰cycloalkyl, —R¹⁰OH, —R¹⁰(OR¹⁰)$_w$ where w is 1–10, and —R¹⁰NR¹⁰R¹⁰;

each R¹⁰ is the same or different and is independently selected from the group consisting of alkyl, cycloalkyl, alkenyl, cycloalkenyl and alkynyl;

n is 0, 1 or 2;
  Ay is aryl;
  Het is a 5- or 6-membered heterocyclic or heteroaryl group;

Y is N;
R³ and R⁴ are both H;
q is 0, 1, 2, 3, 4 or 5;
each R⁵ is the same or different and is independently selected from the group consisting of halo, alkyl, cycloalkyl, alkenyl, cycloalkenyl, alkynyl, Ay, Het, —OR⁷, —OAy, —OHet, —C(O)R⁹, —CO₂R⁹, —C(O)NR⁷R⁸, —C(O)Ay, —C(O)NR⁷Ay, —C(O)Het, —C(O)NHR¹⁰Het, —C(S)NR⁹R¹¹, —C(NH)NR⁷R⁸, —C(NH)NR⁷Ay, —S(O)$_n$R⁹, —S(O)₂NR⁷R⁸, —S(O)₂NR⁷Ay, —NR⁷R⁸, —NR⁷Ay, —NHHet, —NHR¹⁰Ay, —NHR¹⁰Het, —R¹⁰cycloalkyl, —R¹⁰OR⁹, —R¹⁰NR⁷R⁸, —R¹⁰NR⁷Ay, —R¹⁰C(O)R⁹, —R¹⁰CO₂R⁹, —R¹⁰C(O)NR⁹R¹¹, —R¹⁰C(S)NR⁹R¹¹, —R¹⁰NHC(NH)NR⁹R¹¹, —R¹⁰C(NH)NR⁹R¹¹, —R¹⁰SO₂R⁹, —R¹⁰SO₂NHCOR⁹, —R¹⁰SO₂NR⁹R¹¹, cyano, nitro and azido; or two adjacent R⁵ groups together with the atoms to which they are bonded form a C$_{5-6}$ cycloalkyl or aryl;

p' is 1, 2 or 3; and each R⁶ is the same or different and is independently selected from the group consisting of halo, alkyl, cycloalkyl, alkenyl, cycloalkenyl, alkynyl, Ay, Het, —OR⁷, —OAy, —OHet, —OR¹⁰Ay, —OR¹⁰Het, —C(O)R⁹, —CO₂R⁹, —C(O)NR⁷R⁸, —C(O)Ay, —C(O)NR⁷Ay, —C(O)NHR¹⁰Ay, —C(O)Het, —C(O)NHR¹⁰Het, —C(S)NR⁹R¹¹, —C(NH)NR⁷R⁸, —C(NH)NR⁷Ay, —S(O)$_n$R⁹, —S(O)$_n$Ay, —S(O)$_n$Het, —S(O)₂NR⁷R⁸, —S(O)₂NR⁷Ay, —NR⁷R⁸, —NR⁷Ay, —NHR¹⁰Ay, —NHHet, —NHR¹⁰Het, —R¹⁰cycloalkyl, —R¹⁰Ay, —R¹⁰Het, —R¹⁰OR⁹, —R¹⁰—O—C(O)R⁹, —R¹⁰—O—C(O)Ay, —R¹⁰—O—C(O)Het, —R¹⁰—O—S(O)$_n$R⁹, —R¹⁰NR⁷R⁸, —R¹⁰NR⁷Ay, —R¹⁰C(O)R⁹, —R¹⁰CO₂R⁹, —R¹⁰C(O)NR⁹R¹¹, —R¹⁰C(S)NR⁹R¹¹, —R¹⁰NHC(NH)NR⁹R¹¹, —R¹⁰C(NH)NR⁹R¹¹, —R¹⁰SO₂R⁹, —R¹⁰SO₂NHCOR⁹, —R¹⁰SO₂NR⁹R¹¹, cyano, nitro and azido; or two adjacent R⁶ groups together with the atoms to which they are bonded form a C$_{5-6}$ cycloalkyl or a 5- or 6-membered heterocyclic group containing 1 or 2 heteroatoms;

R$^{6x}$ is selected form the group consisting of —NR⁷R⁸ where R⁷ and R⁸ are not both H, —NR⁷Ay, —NHHet, —NHR¹⁰Ay and —NHR¹⁰Het; and Ra is alkyl or cycloalkyl.

Generally, the process for preparing the compounds of formula (I) wherein Y is N; R² is selected from the group consisting of alkyl, cycloalkyl, alkenyl, cycloalkenyl, Ay, Het, —OR⁷, —OAy, —OHet, —OR¹⁰Het —S(O)$_n$R⁹, —S(O)Ay, —S(O)$_n$Het, —S(O)$_n$NR⁷R⁸, —NR⁷R⁸, —NHHet, —NHR¹⁰Het, —NHR¹⁰Ay, —R¹⁰NR⁷R⁸ and —R¹⁰NR⁷Ay; and R³ and R⁴ are H; (all formulas and all other variables having been defined above in connection with Scheme 1-A) comprises the steps of:

(a) reacting a 2-chloro-5-trifluoromethylpyridine of formula (XI-A) with an acetophenone of formula (XXVII) to prepare a compound of formula (III-A);

(b) reacting the compound of formula (III-A) with a hydroxylamine source to prepare a compound of formula (IV-A);

(c) reacting the compound of formula (IV-A) with an acylating or sulfonylating agent to prepare a compound of formula (V-A);

(d) rearranging the compound of formula (V-A) to prepare a compound of formula (VI-A);

(e) acylating the compound of formula (VI-A) to prepare a compound of formula (VII-A);

(f) reacting the compound of formula (VII-A) with a dimethylformamide dialkyl acetal of formula $(CH_3)_2NCH(ORa)_2$ to prepare a compound of formula (IX-A);

(g) reacting the compound of formula (IX-A) with a compound of formula (X) to prepare a compound of formula (XXX);

(h) reacting the compound of formula (XXX) with sodium ethoxide to prepare a compound of formula (XXXI);

(i) reacting the compound of formula (XXXI) with an acid, followed by hydrolysis of the resulting ester to give a compound of formula (XXXII);

(j) reacting the compound of formula (XXXII) with diphenylphosphoryl azide in tert-butanol to give a compound of formula (I-X);

(k) optionally cleaving the compound of formula (I-X) to give a compound of formula (I-Y); and (l) optionally converting the compound of formula (I-Y) to a compound of formula (I-Z) using conditions selected from the group consisting of cross coupling, reductive amination, alkylation, acylation and sulfonylation.

It will be appreciated by those skilled in the art that the compounds of formula (XXX), (XXXI) and (XXXII) in this and the following Schemes are in fact compounds of formula (I) when p' is 1 or 2 and at least one $R^6$ is selected from the group consisting of $—NR^7R^8$, $—NR^7Ay$, $—NHHet$, $—NHR^{10}Het$ and $—NHR^{10}Ay$. When the compounds of formula (XXX), (XXXI) and (XXXII) are defined wherein p is 0 or no $R^6$ is selected from the group consisting of $—NR^7R^8$, $—NR^7Ay$, $—NHHet$, $—NHR^{10}Het$ and $—NHR^{10}Ay$, the compounds of formula (XXX), (XXXI) and (XXXII) may be converted into compounds of formula (I) using the following methods.

More specifically, compounds of formula (I) wherein Y is N; $R^2$ is selected from the group consisting of alkyl, cycloalkyl, alkenyl, cycloalkenyl, Ay, Het, $—OR^7$, $—OAy$, $—OHet$, $—OR^{10}Het$—$S(O)_nR^9$, $—S(O)_nAy$, $—S(O)_nHet$, $—S(O)_nNR^7R^8$, $—NR^7R^8$, $—NHHet$, $—NHR^{10}Het$, $—NHR^{10}Ay$, $—R^{10}NR^7R^8$ and $—R^{10}NR^7Ay$; and $R^3$ and $R^4$ are H, can be prepared by a Curtius rearrangement well known to those skilled in the art.

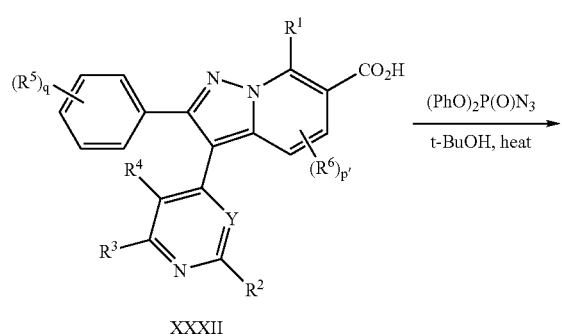

XXXII

The rearrangement can be performed by treating a compound of formula (XXXII) with diphosphoryl azide in tert-butanol in the presence of base with heating. Other carboxylic acid derived migratory rearrangements commonly known to one skilled in the art (such as the Lossen, Hofmann, and Schmidt reactions) may also be useful in this regard.

The foregoing reaction produces particular compounds of formula (I) (i.e., compounds of formula (I-X)) where at least one $R^6$ is $—NR^7R^8$ wherein $R^7$ is H and $R^8$ is $CO_2R^9$ and $R^9$ is tert-butyl. The compounds of formula (I-X) may optionally be further converted to other compounds of formula (I) (i.e., compounds of formula (I-Y)) where at least one $R^6$ is $—NR^7R^8$ and $R^7$ and $R^8$ are both H, by acid catalyzed hydrolysis of the tert-butyl carbamate in a suitable solvent.

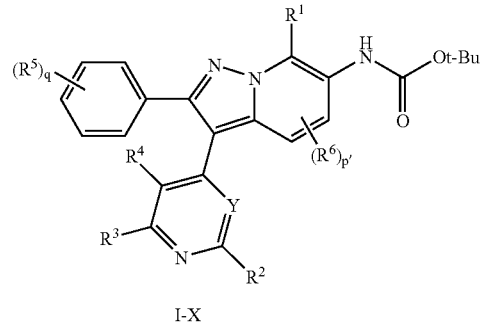

I-X

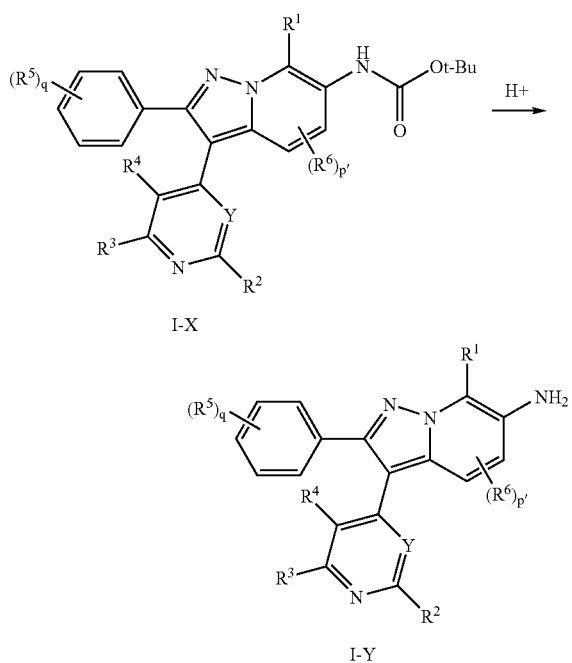

Suitable acids include hydrochloric acid and trifluoroacetic acid and the like. Suitable solvents include dioxane, diethyl ether, tetrahydrofuran, dichloromethane and the like.

The compounds of formula (I-Y) may optionally be further converted to other compounds of formula (I) (i.e., compounds of formula (I-Z) where at least one $R^{6x}$ is selected from the group consisting of —NR$^7$R$^8$ (wherein R$^7$ and R$^8$ are not both H), —NR$^7$Ay, —NHHet, —NHR$^{10}$Het and —NHR$^{10}$Ay, by a cross coupling reaction (e.g., a Buchwald coupling), reductive amination, alkylation, acylation or sulfonylation, depending upon the particular compound of formula (I-Z) that is desired.

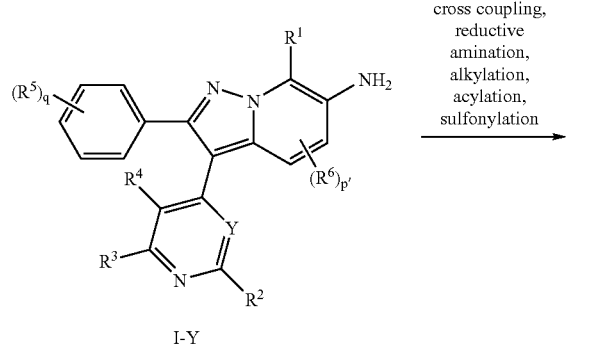

I-Y

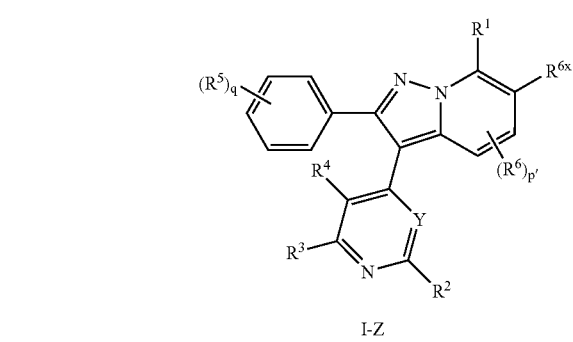

I-Z

One skilled in the art will readily be able to convert compounds of formula (I-Y) to compounds of formula (I-Z) using these general techniques.

Compounds of formula (XXXII), from which compounds of formula (I-X) are synthesized, can be readily prepared by reacting a compound of formula (XXXI) with an acid, followed by hydrolysis of the resulting ester.

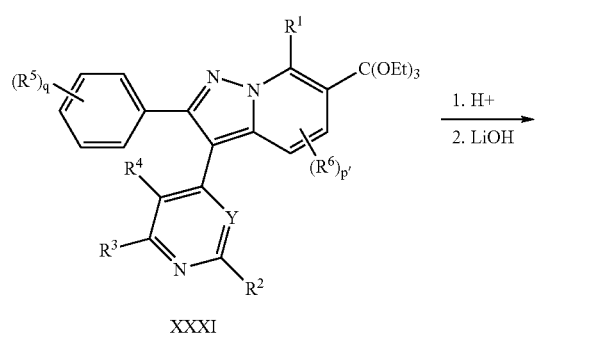

XXXI

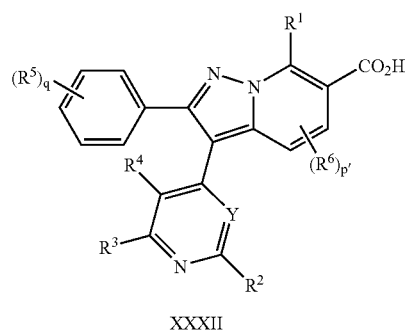

XXXII

Suitable acids include but are not limited to p-toluenesulfonic acid, camphorsulfonic acid, pyridinium p-toluenesulfonic acid and the like. An appropriate solvent such as acetone may be used. The hydrolysis can be performed using lithium hydroxide and the like in a pure or mixed solvent system including but not limited to solvents such as tetrahydrofuran, methanol, and water.

Compounds of formula (XXXI) are prepared by treating a compound of formula (XXX) with an alkoxide salt in an alcohol solvent.

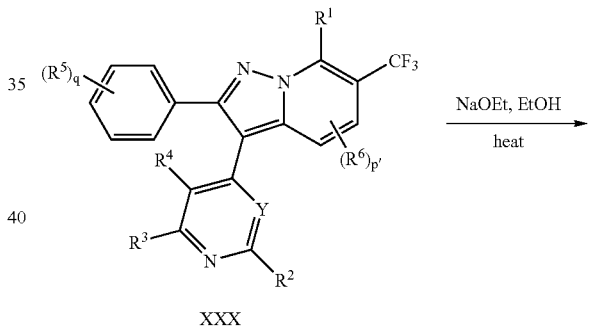

XXX

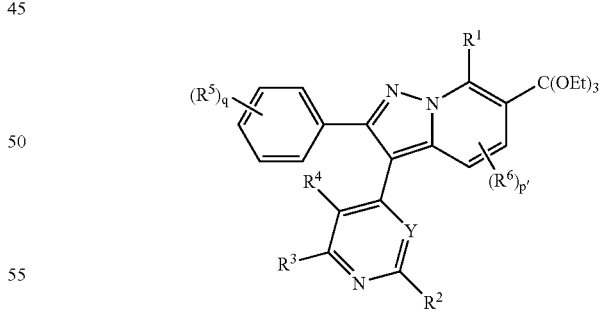

XXXI

Suitable conditions for the foregoing reaction include the use of sodium ethoxide as the alkoxide, and ethanol as a choice solvent. The reaction may optionally be heated to 60° C.

Compounds of formula (XXX) can be prepared using methods analogous to those described above for the preparation of compounds of formula (I) according to Scheme 1, with the exception that the first step (i.e., the preparation of compounds of formula (III-A)) involves the condensation of 2-chloro-5-trifluoromethylpyridine with the acetophenone of formula (XXVII) under basic conditions, in place of the reaction of the picoline of formula (XI) with the benzoylating agent of formula (II) as is employed in the synthesis of the compound of formula (III) in Scheme 1.

In a further embodiment of the present invention, compounds of formula (I) wherein Y is N; $R^2$ is selected from the group consisting of alkyl, cycloalkyl, alkenyl, cycloalkenyl, Ay, Het, —$OR^7$, —OAy, —OHet, —$OR^{10}$Het—$S(O)_nR^9$, —$S(O)_n$Ay, —$S(O)_n$Het, —$S(O)_nNR^7R^8$, —$NR^7R^8$, —NH-Het, —$NHR^{10}$Het, —$NHR^{10}$Ay, —$R^{10}NR^7R^8$ and —$R^{10}NR^7$Ay; $R^3$ is selected from the group consisting of H, alkyl, cycloalkyl, alkenyl, —$R^{10}OR^7$, —$NR^7R^8$ (where $R^7$ and $R^8$ are not H), Ay, —$R^{10}$OAy, —$NR^7$Ay (where $R^7$ is not H), —$R^{10}NR^7R^8$, —$R^{10}NR^7$Ay, —$C(O)R^7$, —C(O)Ay, —$CO_2R^7$, —$CO_2$Ay, —$SO_2NHR^9$ and Het; $R^4$ is H; and at least one $R^6$ is selected from the group consisting of —$NR^7R^8$, —$NR^7$Ay, —NHHet, —$NHR^{10}$Ay and —$NHR^{10}$Het, may be conveniently prepared by the process outlined in Scheme 2 below.

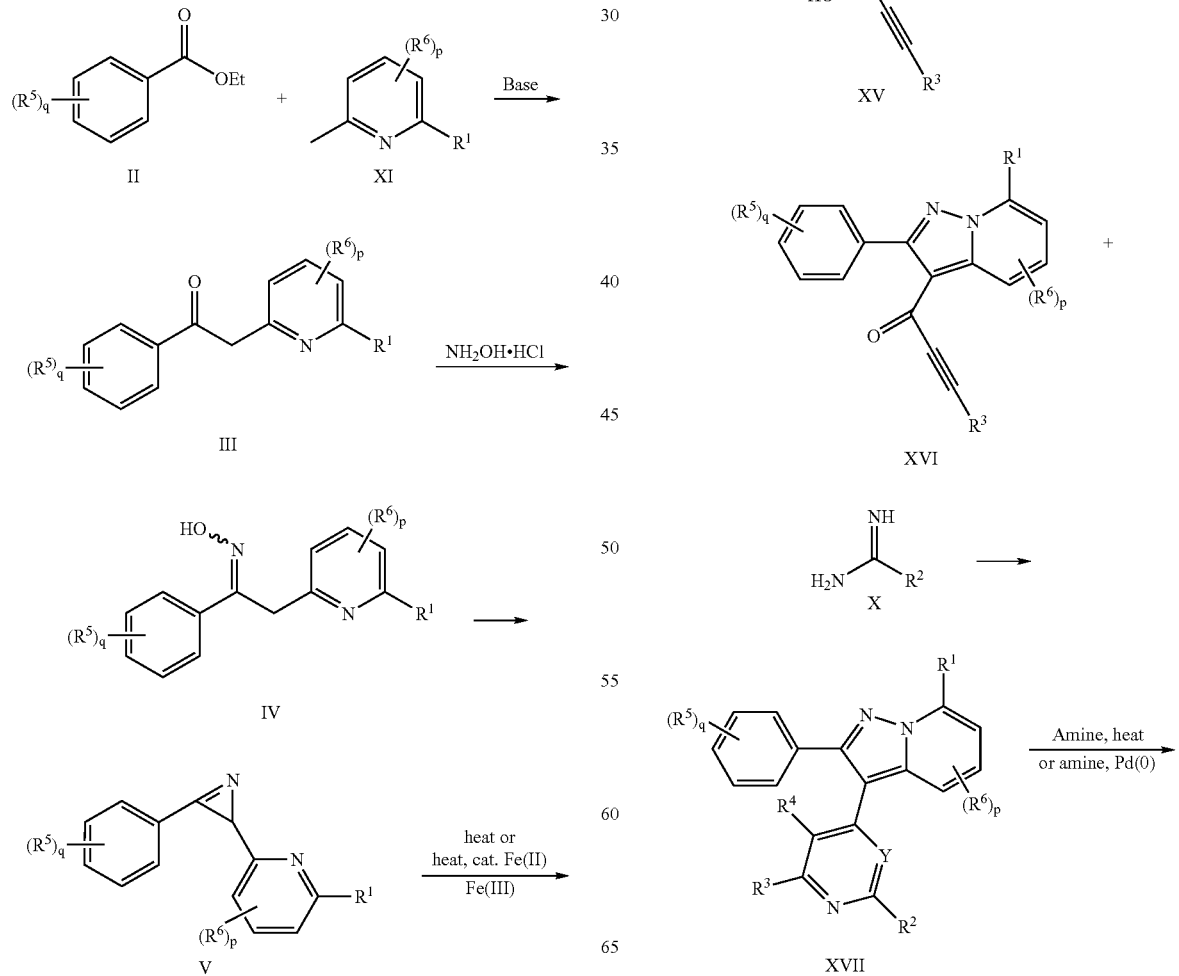

-continued

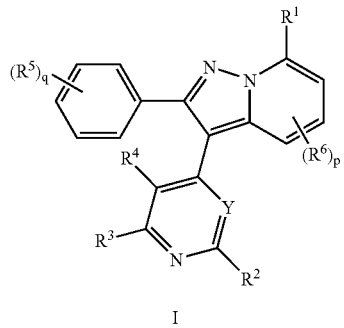

I when no R⁶ is ──NR⁷R⁸, ──NR⁷Ay, ──NHHet, ──NHR¹⁰Ay
or ──NHR¹⁰Het wherein:
R¹ is H;
R² is selected from the group consisting of alkyl, cycloalkyl, alkenyl, cycloalkenyl, Ay, Het, —OR⁷, —OAy, —OHet, —OR¹⁰Het—S(O)$_n$R⁹, —S(O)Ay, —S(O)$_n$Het, —S(O)$_n$NR⁷R⁸, —NR⁷R⁸, —NHHet, —NHR¹⁰Het, —NHR¹⁰Ay, —R¹⁰NR⁷R⁸ and —R¹⁰NR⁷Ay;
  each R⁷ and R⁸ are the same or different and are independently selected from the group consisting of H, alkyl, cycloalkyl, alkenyl, cycloalkenyl, —OR⁹, —C(O)R⁹, —CO₂R⁹, —C(O)NR⁹R¹¹, —C(S)NR⁹R¹¹, —C(NH)NR⁹R¹¹, —SO₂R¹⁰, —SO₂NR⁹R¹¹, —R¹⁰cycloalkyl, —R¹⁰OR⁹, —R¹⁰NR⁹R¹¹, —R¹⁰C(O)R⁹, —R¹⁰CO₂R⁹, —R¹⁰C(O)NR⁹R¹¹, —R¹⁰C(S)NR⁹R¹¹, —R¹⁰NHC(NH)NR⁹R¹¹, —R¹⁰C(NH)NR⁹R¹¹, —R¹⁰SO₂R¹⁰, —R¹⁰SO₂NR⁹R¹¹, —R¹⁰NHSO₂R⁹, —R¹⁰NHCOR⁹ and —R¹⁰SO₂NHCOR⁹;
  each R⁹ and R¹¹ are the same or different and are independently selected from the group consisting of H, alkyl, cycloalkyl, —R¹⁰cycloalkyl, —R¹⁰OH, —R¹⁰(OR¹⁰)$_w$ where w is 1–10, and —R¹⁰NR¹⁰R¹⁰;
  each R¹⁰ is the same or different and is independently selected from the group consisting of alkyl, cycloalkyl, alkenyl, cycloalkenyl and alkynyl;
  n is 0, 1 or 2;
  Ay is aryl;
  Het is a 5- or 6-membered heterocyclic or heteroaryl group;
Y is N;
R³ is selected from the group consisting of H, halo, alkyl, cycloalkyl, alkenyl, —R¹⁰OR⁷, —NR⁷R⁸ (where R⁷ and R⁸ are not H), Ay, —R¹⁰OAy, —NR⁷Ay, (where R⁷ is not H), —R¹⁰NR⁷R⁸, —R¹⁰NR⁷Ay, —C(O)R⁷, —CO₂R⁷, —CO₂Ay, —SO₂NHR⁹ and Het;
R⁴ is H;
q is 0, 1, 2, 3, 4 or 5;
each R⁵ is the same or different and is independently selected from the group consisting of halo, alkyl, cycloalkyl, alkenyl, cycloalkenyl, alkynyl, Ay, Het, —OR⁷, —OAy, —OHet, —C(O)R⁹, —CO₂R⁹, —C(O)NR⁷R⁸, —C(O)Ay, —C(O)NR⁷Ay, —C(O)Het, —C(O)NHR¹⁰Het, —C(S)NR⁹R¹¹, —C(NH)NR⁷R⁸, —C(NH)NR⁷Ay, —S(O)$_n$R⁹, —S(O)₂NR⁷R⁸, —S(O)₂NR⁷Ay, —NR⁷R⁸, —NR⁷Ay, —NHHet, —NHR¹⁰Ay, —NHR¹⁰Het, —R¹⁰cycloalkyl, —R¹⁰OR⁹, —R¹⁰NR⁷R⁸, —R¹⁰NR⁷Ay, —R¹⁰C(O)R⁹, —R¹⁰CO₂R⁹, —R¹⁰C(O)NR⁹R¹¹, —R¹⁰C(S)NR⁹R¹¹, —R¹⁰NHC(NH)NR⁹R¹¹, —R¹⁰C(NH)NR⁹R¹¹, —R¹⁰SO₂R⁹, —R¹⁰SO₂NHCOR⁹, —R¹⁰SO₂NR⁹R¹¹, cyano, nitro and azido; or
  two adjacent R⁵ groups together with the atoms to which they are bonded form a C₅₋₆ cycloalkyl or aryl;
p is 1, 2 or 3; and
each R⁶ is the same or different and is independently selected from the group consisting of halo, alkyl, cycloalkyl, alkenyl, cycloalkenyl, alkynyl, Ay, Het, —OR⁷, —OAy, —OHet, —OR¹⁰Ay, —OR¹⁰Het, —C(O)R⁹, —CO₂R⁹, —C(O)NR⁷R⁸, —C(O)Ay, —C(O)NR⁷Ay, —C(O)NHR¹⁰Ay, —C(O)Het, —C(O)NHR¹⁰Het, —C(S)NR⁹R¹¹, —C(NH)NR⁷R⁸, —C(NH)NR⁷Ay, —S(O)$_n$R⁹, —S(O)$_n$Ay, —S(O)$_n$Het, —S(O)₂NR⁷R⁸, —S(O)₂NR⁷Ay, —NR⁷R⁸, —NR⁷Ay, —NHR¹⁰Ay, —NHHet, —NHR¹⁰Het, —R¹⁰cycloalkyl, —R¹⁰Ay, —R¹⁰Het, —R¹⁰OR⁹, —R¹⁰—O—C(O)R⁹, —R¹⁰—O—C(O)Ay, —R¹⁰—O—C(O)Het, —R¹⁰—O—S(O)$_n$R⁹, —R¹⁰NR⁷R⁸, —R¹⁰NR⁷Ay, —R¹⁰C(O)R⁹, —R¹⁰CO₂R⁹, —R¹⁰C(O)NR⁹R¹¹, —R¹⁰C(S)NR⁹R¹¹, —R¹⁰NHC(NH)NR⁹R¹¹, —R¹⁰C(NH)NR⁹R¹¹, —R¹⁰SO₂R⁹, —R¹⁰SO₂NHCOR⁹, —R¹⁰SO₂NR⁹R¹¹, cyano, nitro and azido; or
  two adjacent R⁶ groups together with the atoms to which they are bonded form a C₅₋₆ cycloalkyl or a 5- or 6-membered heterocyclic group containing 1 or 2 heteroatoms;
wherein in the compounds of formulas (XI), (III), (IV), (V), (VI), (XIII), (XV), (XVI) and (XVII) at least one R⁶ is selected from the group consisting of halo, —NR⁷R⁸, —NR⁷Ay, —NHHet, —NHR¹⁰Ay and —NHR¹⁰Het;
wherein in the compounds of formula (I) at least one R⁶ is selected from the group consisting of —NR⁷R⁸, —NR⁷Ay, —NHHet, —NHR¹⁰Ay and —NHR¹⁰Het; and
M¹ is Li, Mg-halide or cerium-halide, wherein halide is halo.
  Generally, the process for preparing compounds of formula (I) wherein Y is N; R² is selected from the group consisting of alkyl, cycloalkyl, alkenyl, cycloalkenyl, Ay, Het, —OR⁷, —OAy, —OHet, —OR¹⁰Het—S(O)$_n$R⁹, —S(O)$_n$Ay, —S(O)$_n$Het, —S(O)$_n$NR⁷R⁸, —NR⁷R⁸, —NHHet, —NHR¹⁰Het, —NHR¹⁰Ay, —R¹⁰NR⁷R⁸ and —R¹⁰NR⁷Ay; R³ is selected from the group consisting of H, alkyl, cycloalkyl, alkenyl, —R¹⁰OR⁷, —NR⁷R⁸ (where R⁷ and R⁸ are not H), Ay, —R¹⁰OAy, —NR⁷Ay (where R⁷ is not H), —R¹⁰NR⁷R⁸, —R¹⁰NR⁷Ay, —C(O)R⁷, —C(O)Ay, —CO₂R⁷, —CO₂Ay, —SO₂NHR⁹ and Het; R⁴ is H; and at least one R⁶ is selected from the group consisting of —NR⁷R⁸, —NR⁷Ay, —NHHet, —NHR¹⁰Ay and —NHR¹⁰Het, (all other variables having been defined above in connection with Scheme 2), comprises the following steps:
(a) reacting a picoline of formula (XI) with a benzoylating agent of formula (II) to prepare a compound of formula (III);
(b) reacting the compound of formula (III) with a hydroxylamine source to prepare a compound of formula (IV);
(c) reacting the compound of formula (IV) with an acylating or sulfonylating agent to prepare a compound of formula (V);
(d) rearranging the compound of formula (V) to prepare a compound of formula
(e) formylating the compound of formula (VI) to prepare a compound of formula (XIII);
(f) reacting the compound of formula (XIII) with a compound of formula (XIV) to prepare a compound of formula (XV);
(g) oxidizing the compound of formula (XI) to prepare a compound of formula (XVI);

(h) reacting a compound of formula (XVI) with a compound of formula (X) to prepare a compound of formula (XVII); and (i) in the embodiment wherein no $R^6$ in the compound of formula (XVII) is —$NR^7R^8$, —$NR^7Ay$, —NHHet, —$NHR^{10}Ay$ or —$NHR^{10}Het$, replacing the $R^6$ halo of the compound of formula (XVII) with an amine substituent selected from the group consisting of —$NR^7R^8$, —$NR^7Ay$, —NHHet, —$NHR^{10}Het$ and —$NHR^{10}Ay$ to prepare a compound of formula (I), wherein at lest one $R^6$ is selected from the group consisting of —$NR^7R^8$, —$NR^7Ay$, —NHHet, —$NHR^{10}Ay$ and —$NHR^{10}Het$.

It will be appreciated by those skilled in the art that the compounds of formula (XVII) in this and the following Schemes, are in fact compounds of formula (I) when p is 1 or 2 and at least one $R^6$ is selected from the group consisting of —$NR^7R^8$, —$NR^7Ay$, —NHHet, —$NHR^{10}Ay$ and —$NHR^{10}Het$. When the compounds of formula (XVII) are defined wherein p is 0 or no $R^6$ is selected from the group consisting of —$NR^7R^8$, —$NR^7Ay$, —NHHet, —$NHR^{10}Het$ and —$NHR^{10}Ay$, the compounds of formula (XVII) or pharmaceutically acceptable salts, solvates and physiologically functional derivatives thereof may be converted into compounds of formula (I) using the following methods. While the chemical formulas of the compounds of formula (XVII) and the compounds of formula (I) are represented as the same, the definition of the variable $R^6$ differs; with respect to the compounds of formula (XVII) at least one $R^6$ must be selected from the group consisting of halo, —$NR^7R^8$, —$NR^7Ay$, —NHHet, —$NHR^{10}Ay$ and —$NHR^{10}Het$, whereas in the compounds of formula (I) at least one $R^6$ must be selected from the group consisting of —$NR^7R^8$, —$NR^7Ay$, —NHHet, —$NHR^{10}Ay$ and —$NHR^{10}Het$.

The foregoing process and following Schemes involving the conversion of the $R^6$ halo substituent on the compounds of formula (XVII) to the amine substituent (—$NR^7R^8$, —$NR^7Ay$, —NHHet, —$NHR^{10}Het$ or —$NHR^{10}Ay$) in the compounds of formula (I) is described as occurring at the end of the synthesis. However, one skilled in the art will readily appreciate that the conversion of the halogen to the amine substituent can occur at earlier stages in the process as well, using the same techniques as are described herein. For example, any of the halogenated intermediates may be converted to the amine analogues prior to proceeding with the next step of the synthesis. This would of course eliminate the need for performing this conversion as the final step. The various permutations of the foregoing synthesis wherein the conversion of the halogen to the amine occurs earlier in the synthesis are contemplated by the instant invention and encompassed within its scope. Thus, the order of the foregoing steps of the synthesis is not critical to obtaining the compounds of formula (I). In the embodiments wherein the conversion of the halogen substituent to the amine occurs earlier in the synthesis, or where at least one $R^6$ in the compound of formula (XVI) is selected from the group consisting of —$NR^7R^8$, —$NR^7Ay$, —NHHet, —$NHR^{10}Ay$ and —$NHR^{10}Het$, the compounds of formula (I) are a direct result of the reaction of the compound of formula (XVI) and a compound of formula (X) and the amination step depicted last is not required.

More specifically, wherein no $R^6$ in the compound of formula (XVII) is selected from the group consisting of —$NR^7R^8$, —$NR^7Ay$, —NHHet, —$NHR^{10}Ay$ and —$NHR^{10}Het$ (i.e., said at least one $R^6$ is halo; herein "$R^6$ halo"), compounds of formula (I) wherein Y is N; $R^2$ is selected from the group consisting of alkyl, cycloalkyl, alkenyl, cycloalkenyl, Ay, Het, —$OR^7$, —OAy, —OHet, —$OR^{10}Het$—$S(O)_nR^9$, —$S(O)_nAy$, —$S(O)_nHet$, —$S(O)_nNR^7R^8$, —$NR^7R^8$, —NHHet, —$NHR^{10}Het$, —$NHR^{10}Ay$, —$R^{10}NR^7R^8$ and —$R^{10}NR^7Ay$; $R^3$ is selected from the group consisting of H, alkyl, cycloalkyl, alkenyl, —$R^{10}OR^7$, —$NR^7R^8$ (where $R^7$ and $R^8$ are not H), Ay, —$R^{10}Ay$, —$NR^7Ay$ (where $R^7$ is not H), —$R^{10}NR^7R^8$, —$R^{10}NR^7Ay$, —$C(O)R^7$, —C(O)Ay, —$CO_2R^7$, —$CO_2Ay$, —$SO_2NHR^9$ and Het; $R^4$ is H; and at least one $R^6$ is selected from the group consisting of —$NR^7R^8$, —$NR^7Ay$, —NHHet, —$NHR^{10}Ay$ and —$NHR^{10}Het$, may be prepared by replacing the $R^6$ halo on the compounds of formula (XVII) with an amine substituent selected from the group consisting of —$NR^7R^8$, —$NR^7Ay$, —NHHet, —$NHR^{10}Het$ and —$NHR^{10}Ay$.

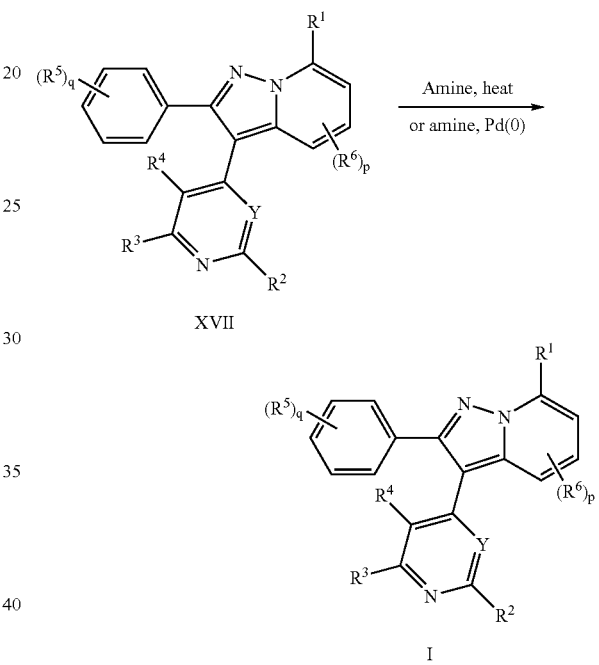

Typically the replacement is carried out by mixing the compound of formula (XVII) with an amine nucleophile selected from the group consisting of —$NR^7R^8$, —$NR^7Ay$, —NHHet, —$NHR^{10}Ay$ and —$NHR^{10}Het$; and optionally heating the reaction.

Alternatively, the process of converting compounds of formula (XVII) to compounds of formula (I) is carried out by reacting a compound of formula (XVII) with an imine in the presence of a palladium (0) source, a base and a suitable ligand, followed by hydrolysis to give a compound of formula (I). See J. Wolfe, et al., *Tetrahedron Letters* 38:6367–6370 (1997). Typically the imine is benzophenoneimine, the palladium (0) source is tris(dibenzylideneacetone)dipalladium(0), the base is sodium tert-butoxide and the ligand is racemic-2,2'-bis(diphenylphosphino)-1,1'-binaphthyl. Suitable solvents include N,N-dimethylformamide and the like.

The reaction can also be carried out via an adaptation of procedures found in the literature (Wolfe, J. P.; Buchwald, S. L *J. Org. Chem.* 2000, 65, 1144) wherein a compound of the formula (XVII) is treated with an amine, a palladium (0) or nickel (0) source and a base in a suitable solvent. Suitable sources of palladium (0) include but are not limited to palladium(II) acetate and tris(dibenzylideneacetone) dipalladium (0). Typical bases for use in the reaction include, for example sodium tert-butoxide and cesium carbonate. Toluene is an example of a suitable solvent.

Compounds of formula (XVII) can be prepared by reacting a compound of formula (XVI) with a compound of formula (X).

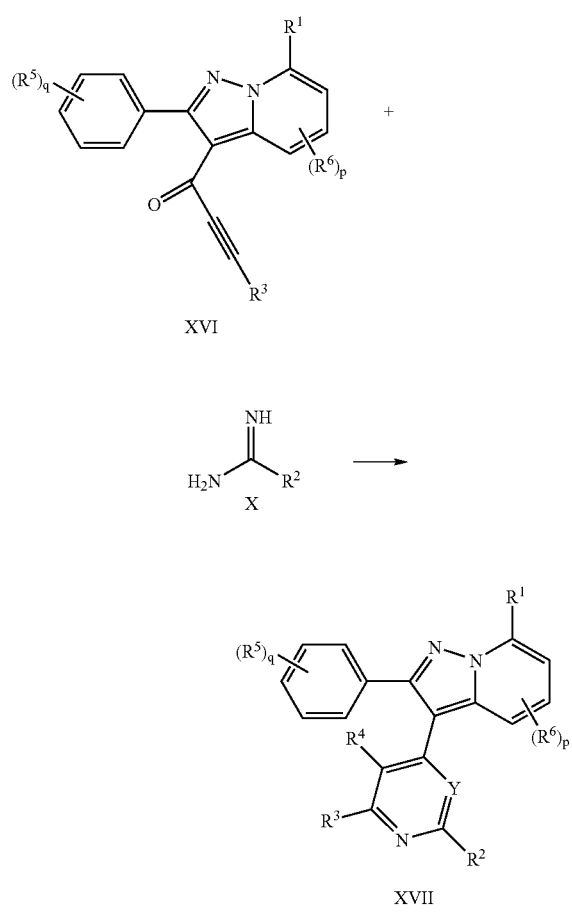

wherein all variables are as defined above in connection with Scheme 2. As will be apparent to those skilled in the art, when compounds of formula (XVI) are defined where at least one $R^6$ is selected from the group consisting of $NR^7R^8$, $-NR^7Ay$, $-NHHet$, $-NHR^{10}Ay$ and $-NHR^{10}Het$, the compounds of formula (I) result directly from the foregoing reaction.

This method can be readily carried out by mixing a compound of formula (XVI) with a compound of formula (X) in a suitable solvent, optionally in the presence of a base. The reaction may be heated to 50–150° C. or performed at ambient temperature. Typical solvents include but are not limited to lower alcohols such as methanol, ethanol, isopropanol and the like. Typical bases include for example, sodium alkoxide, potassium carbonate, or an amine base such as triethylamine. In another embodiment, the solvent is N,N-dimethylformamide and the base is potassium carbonate, or an amine base such as triethylamine.

Compounds of formula (XVI) may be conveniently prepared by oxidation of a compound of formula (XV).

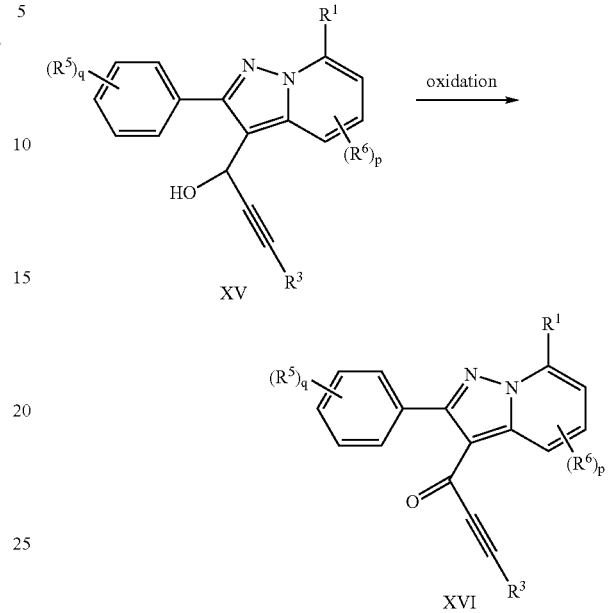

wherein all variables are as defined above in connection with Scheme 2.

Preferred oxidizing agents include but are not limited to, manganese dioxide, and the like, in an inert solvent. Suitable inert solvents include but are not limited to, dichloromethane, chloroform, N,N-dimethylformamide, ether, and the like.

Compounds of formula (XV) may be conveniently prepared by reacting a compound of formula (XIII) with a compound of formula (XIV).

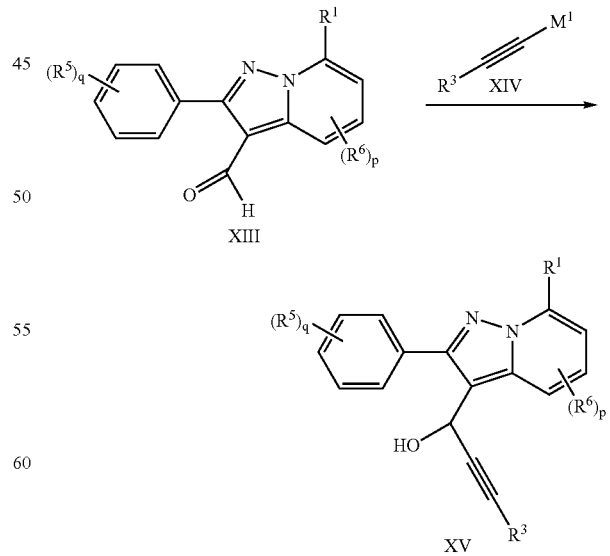

wherein all variables are as defined above in connection with Scheme 2.

Preferred metals ($M^1$) in the compounds of formula (XIV) include but are not limited to, lithium, magnesium(II) halides, cerium(III) halides, and the like. Compounds of formula (XIV) may be purchased from commercial sources or prepared by methods known to one skilled in the art.

Compounds of formula (XIII) may be conveniently prepared from compounds of formula (VI) by a formylation procedure.

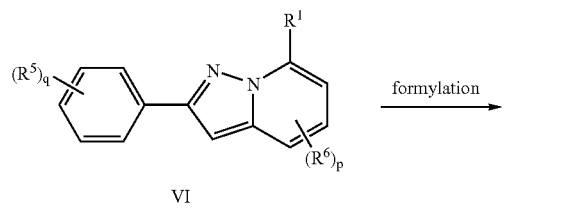

wherein all variables are as defined above in connection with Scheme 2.

Typically the formylation is carried out via the Vilsmeier-Haack reaction. The Vilsmeier-Haack reagents can be purchased from commercial sources or prepared in situ. Preferable conditions include, but are not limited to treating compounds of formula (VI) with a premixed solution of phosphorous oxychloride in N,N-dimethylformamide optionally with heating the reaction to 50–150° C. The compounds of formula (VI) are prepared by the process described above in connection with Scheme 1.

In addition to the foregoing process for preparing certain compounds of formula (I), the present invention also provides certain intermediate compounds for use in the preparation of such compounds of formula (I) according to the foregoing process. Such intermediates are depicted in Scheme 2 above.

In a further embodiment of the present invention, compounds of formula (I) wherein Y is N; $R^2$ is selected from the group consisting of alkyl, cycloalkyl, alkenyl, cycloalkenyl, Ay, Het, —$OR^7$, —OAy, —OHet, —$OR^{10}$Het—$S(O)_n R^9$, —$S(O)_n$Ay, —$S(O)_n$Het, —$S(O)_n NR^7 R^8$, —$NR^7 R^8$, —NH-Het, —$NHR^{10}$Het, —$NHR^{10}$Ay, —$R^{10}NR^7 R^8$ and —$R^{10}NR^7$Ay; $R^3$ is selected from the group consisting of H, alkyl, cycloalkyl, alkenyl, Ay, Het, —$C(O)R^7$, —C(O)Ay, —$CO_2 R^7$, —$CO_2$Ay, —$SO_2 NHR^9$, —$NR^7 R^8$ (where $R^7$ and $R^8$ are not H), —$NR^7$Ay (where $R^7$ is not H), —$R^{10}OR^7$, —$R^{10}$OAy, —$R^{10}NR^7 R^8$ and —$R^{10}NR^7$Ay; and $R^4$ is H, may be conveniently prepared by the process outlined in Scheme 2-A below.

Scheme 2-A

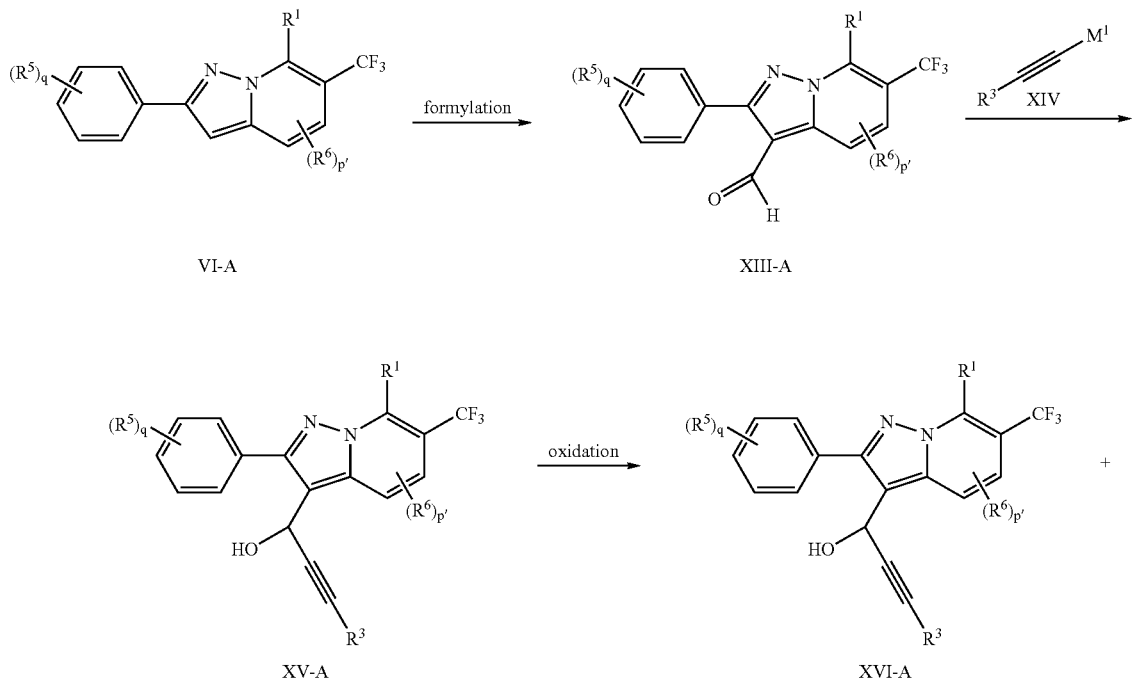

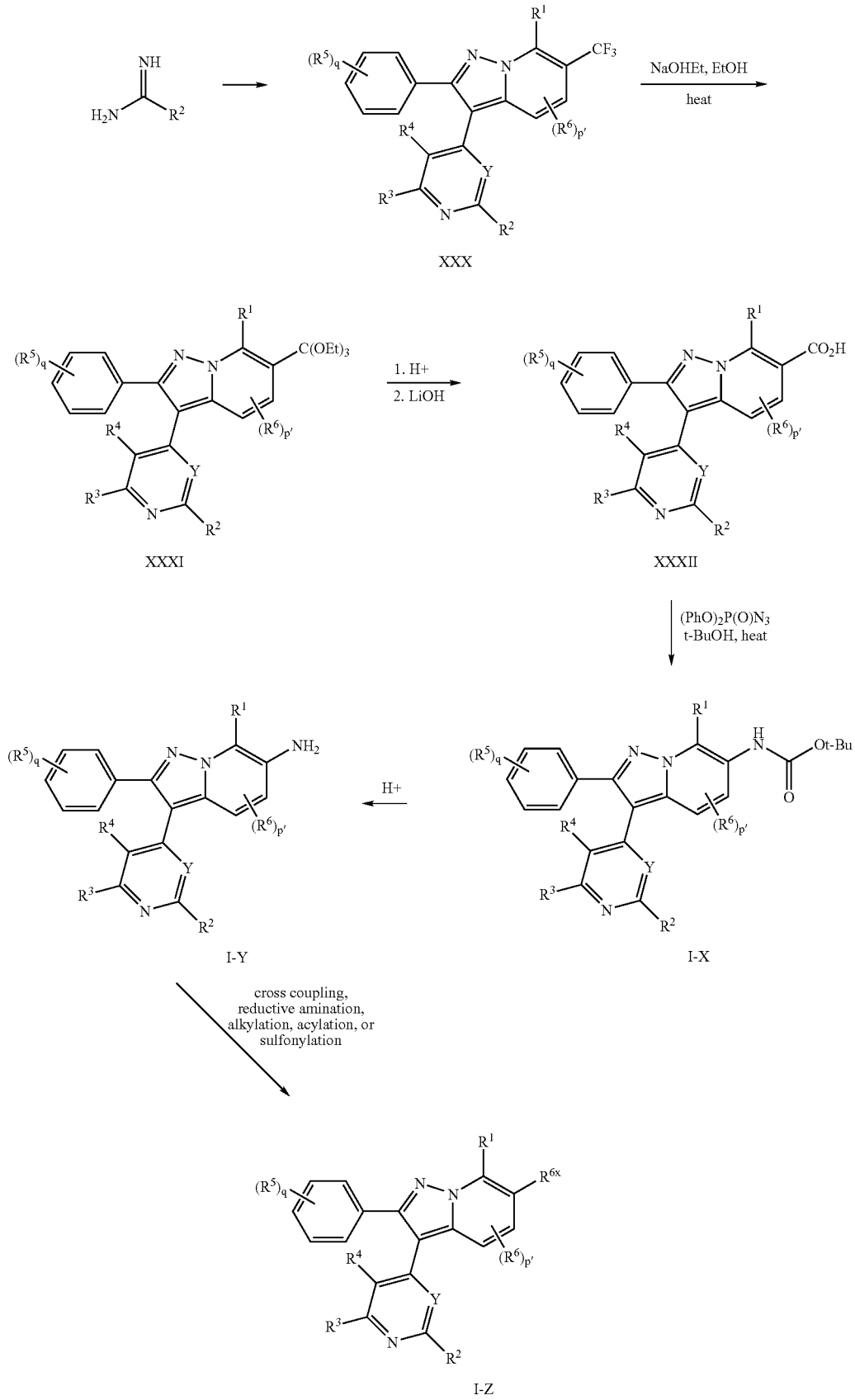

wherein:

$R^1$ is H;

$R^2$ is selected from the group consisting of halo, alkyl, cycloalkyl, alkenyl, cycloalkenyl, Ay, Het, —$OR^7$, —OAy, —OHet, —$OR^{10}$Het, —$S(O)_nR^9$, —$S(O)_n$Ay, —$S(O)_n$Het, —$S(O)_nNR^7R^8$, —$NR^7R^8$, NHHet, —$NHR^{10}$Het, —$NHR^{10}$Ay, —$R^{10}NR^7R^8$ and —$R^{10}NR^7$Ay;

each $R^7$ and $R^8$ are the same or different and are independently selected from the group consisting of H, alkyl, cycloalkyl, alkenyl, cycloalkenyl, —$OR^9$, —$C(O)R^9$, —$CO_2R^9$, —$C(O)NR^9R^{11}$, —$C(S)NR^9R^{11}$, —$C(NH)NR^9R^{11}$, —$SO_2R^{10}$, —$SO_2NR^9R^{11}$, —$R^{10}$cycloalkyl, —$R^{10}OR^9$, —$R^{10}NR^9R^{11}$, —$R^{10}C(O)R^9$, —$R^{10}CO_2R^9$, —$R^{10}C(O)NR^9R^{11}$, —$R^{10}C(S)NR^9R^{11}$, —$R^{10}NHC(NH)NR^9R^{11}$, —$R^{10}C(NH)NR^9R^{11}$, —$R^{10}SO_2R^{10}$, —$R^{10}SO_2NR^9R^{11}$, —$R^{10}NHSO_2R^9$, —$R^{10}NHCOR^9$ and —$R^{10}SO_2NHCOR^9$;

each $R^9$ and $R^{11}$ are the same or different and are independently selected from the group consisting of H, alkyl, cycloalkyl, —$R^{10}$cycloalkyl, —$R^{10}OH$, —$R^{10}(OR^{10})_w$ where w is 1–10, and —$R^{10}NR^{10}R^{10}$;

each $R^{10}$ is the same or different and is independently selected from the group consisting of alkyl, cycloalkyl, alkenyl, cycloalkenyl and alkynyl;

n is 0, 1 or 2;

Ay is aryl;

Het is a 5- or 6-membered heterocyclic or heteroaryl group;

Y is N;

$R^3$ is selected from the group consisting of H, halo, alkyl, cycloalkyl, alkenyl, —$R^{10}OR^7$, —$NR^7R^8$ (where $R^7$ and $R^8$ are not H), Ay, —$R^{10}$OAy, —$NR^7$Ay, (where $R^7$ is not H), —$R^{10}NR^7R^8$, —$R^{10}NR^7$Ay, —$C(O)R^7$, —$CO_2R^7$, —$CO_2$Ay, —$SO_2NHR^9$ and Het;

$R^4$ is H;

q is 0, 1, 2, 3, 4 or 5;

each $R^5$ is the same or different and is independently selected from the group consisting of halo, alkyl, cycloalkyl, alkenyl, cycloalkenyl, alkynyl, Ay, Het, —$OR^7$, —OAy, —OHet, —$C(O)R^9$, —$CO_2R^9$, —$C(O)NR^7R^8$, —$C(O)$Ay, —$C(O)NR^7$Ay, —$C(O)$Het, —$C(O)NHR^{10}$Het, —$C(S)NR^9R^{11}$, —$C(NH)NR^7R^8$, —$C(NH)NR^7$Ay, —$S(O)_nR^9$, —$S(O)_2NR^7R^8$, —$S(O)_2NR^7$Ay, —$NR^7$Ay, —$NR^7R^8$, —NHHet, —$NHR^{10}$Ay, —$NHR^{10}$Het, —$R^{10}$cycloalkyl, —$R^{10}OR^9$, —$R^{10}NR^7R^8$, —$R^{10}NR^7$Ay, —$R^{10}C(O)R^9$, —$R^{10}CO_2R^9$, —$R^{10}C(O)NR^9R^{11}$, —$R^{10}C(S)NR^9R^{11}$, —$R^{10}NHC(NH)NR^9R^{11}$, —$R^{10}C(NH)NR^9R^{11}$, —$R^{10}SO_2R^9$, —$R^{10}SO_2NHCOR^9$, —$R^{10}SO_2NR^9R^{11}$, cyano, nitro and azido; or two adjacent $R^5$ groups together with the atoms to which they are bonded form a $C_{5-6}$ cycloalkyl or aryl;

p' is 1, 2 or 3; and each $R^6$ is the same or different and is independently selected from the group consisting of halo, alkyl, cycloalkyl, alkenyl, cycloalkenyl, alkynyl, Ay, Het, —$OR^7$, —OAy, —OHet, —$OR^{10}$Ay, —$OR^{10}$Het, —$C(O)R^9$, —$CO_2R^9$, —$C(O)NR^7R^9$, —$C(O)$Ay, —$C(O)NR^7$Ay, —$C(O)NHR^{10}$Ay, —$C(O)$Het, —$C(O)NHR^{10}$Het, —$C(S)NR^9R^{11}$, —$C(NH)NR^7R^8$, —$C(NH)NR^7$Ay, —$S(O)_nR^9$, —$S(O)_n$Ay, —$S(O)_n$Het, —$S(O)_2NR^7R^8$, —$S(O)_2NR^7$Ay, —$NR^7R^8$, —$NR^7$Ay, —$NHR^{10}$Ay, —NHHet, —$NHR^{10}$Het, —$R^{10}$cycloalkyl, —$R^{10}$Ay, —$R^{10}$Het, —$R^{10}OR^9$, —$R^{10}$—O—$C(O)R^9$, —$R^{10}$—O—$C(O)$Ay, —$R^{10}$—O—$C(O)$Het, —$R^{10}$—O—$S(O)_nR^9$, —$R^{10}NR^7R^8$, —$R^{10}NR^7$Ay, —$R^{10}C(O)R^9$, —$R^{10}CO_2R^9$, —$R^{10}C(O)NR^9R^{11}$, —$R^{10}C(S)NR^9R^{11}$, —$R^{10}NHC(NH)NR^9R^{11}$, —$R^{10}C(NH)NR^9R^{11}$, —$R^{10}SO_2R^9$, —$R^{10}SO_2NHCOR^9$, —$R^{10}SO_2NR^9R^{11}$, cyano, nitro and azido; or two adjacent $R^6$ groups together with the atoms to which they are bonded form a $C_{5-6}$ cycloalkyl or a 5- or 6-membered heterocyclic group containing 1 or 2 heteroatoms;

$R^{6x}$ is selected from the group consisting of —$NR^7R^8$ where $R^7$ and $R^8$ are not both H, —$NR^7$Ay, —NHHet, —$NHR^{10}$Het and —$NHR^{10}$Ay; and $M^1$ is Li, Mg-halide or cerium-halide, wherein halide is halo.

Generally, the process for preparing compounds of formula (I) wherein Y is N; $R^2$ is selected from the group consisting of alkyl, cycloalkyl, alkenyl, cycloalkenyl, Ay, Het, —$OR^7$, —OAy, —OHet, —$OR^{10}$Het—$S(O)_nR^9$, —$S(O)_n$Ay, —$S(O)_n$Het, —$S(O)_nNR^7R^8$, —$NR^7R^8$, —NHHet, —$NHR^{10}$Het, —$NHR^{10}$Ay, —$R^{10}NR^7R^8$ and —$R^{10}NR^7$Ay; $R^3$ is selected from the group consisting of H, alkyl, cycloalkyl, alkenyl, Ay, Het, —$C(O)R^7$, —$C(O)$Ay, —$CO_2R^7$, —$CO_2$Ay, —$SO_2NHR^9$, —$NR^7R^8$ (where $R^7$ and $R^8$ are not H), —$NR^7$Ay (where $R^7$ is not H), —$R^{10}OR^7$, —$R^{10}$OAy, —$R^{10}NR^7R^8$ and —$R^{10}NR^7$Ay; and $R^4$ is H, (all other variables having been defined above in connection with Scheme 2-A), comprises the following steps:

(a) reacting a 2-chloro-5-trifluoromethylpyridine of formula (XI-A) with an acetophenone of formula (XXVII) to prepare a compound of formula (III-A);

(b) reacting the compound of formula (III-A) with a hydroxylamine source to prepare a compound of formula (IV-A);

(c) reacting the compound of formula (IV-A) with an acylating or sulfonylating agent to prepare a compound of formula (V-A);

(d) rearranging the compound of formula (V-A) to prepare a compound of formula (VI-A);

(e) formulating the compound of formula (VI-A) to prepare a compound of formula (XIII-A);

(f) reacting the compound of formula (XIII-A) with a compound of formula (XIV) to prepare a compound of formula (XV-A);

(g) oxidizing the compound of formula (XV-A) to prepare a compound of formula (XVI-A);

(h) reacting a compound of formula (XVI-A) with a compound of formula (X) to prepare a compound of formula (XXX);

(i) reacting the compound of formula (XXX) with sodium ethoxide to prepare a compound of formula (XXXI);

(j) reacting the compound of formula (XXXI) with an acid, followed by hydrolysis of the resulting ester to give a compound of formula (XXXII);

(k) reacting the compound of formula (XXXII) with diphenylphosphoryl azide in tert-butanol to give a compound of formula (I-X);

(l) optionally cleaving the compound of formula (I-X) to give a compound of formula (I-Y); and (m) optionally converting the compound of formula (I-Y) to a compound of formula (I-Z) using conditions selected from the group consisting of cross coupling, reductive amination, alkylation, acylation and sulfonylation.

In particular, compounds of formula (I) wherein Y is N; $R^2$ is selected from the group consisting of alkyl, cycloalkyl, alkenyl, cycloalkenyl, Ay, Het, —$OR^7$, —OAy, —OHet, —$OR^{10}$Het—$S(O)_nR^9$, —$S(O)_n$Ay, —$S(O)_n$Het, —$S(O)_n$ $NR^7R^8$, —$NR^7R^8$, —NHHet, —$NHR^{10}$Het, —$NHR^{10}$Ay, —$R^{10}NR^7R^8$ and —$R^{10}NR^7$Ay; $R^3$ is selected from the group consisting of H, alkyl, cycloalkyl, alkenyl, Ay, Het, —C(O)R$^7$, —C(O)Ay, —CO$_2$R$^7$, —CO$_2$Ay, —SO$_2$NHR$^9$, —NR$^7$R$^8$ (where R$^7$ and R$^8$ are not H), —NR$^7$Ay (where R$^7$ is not H), —R$^{10}$OR$^7$, —R$^{10}$OAy, —R$^{10}$NR$^7$R$^8$ and —R$^{10}$NR$^7$Ay; and R$^4$ is H, can be prepared by converting the compounds of formula (XXX) to compounds of formula (I) using the methods described above in connection with the process of Scheme 1-A.

Compounds of formula (XXX) can be prepared using methods analogous to those described above for the preparation of compounds of formula (XVII) according to Scheme 2, with the exception that the first step (i.e., the preparation of compounds of formula (III-A)) involves the condensation of 2-chloro-5-trifluoromethylpyridine with an acetophenone of formula (XXVII) under basic conditions, in place of the reaction of the picoline of formula (XI) with the benzoylating agent of formula (II) as is employed in the synthesis of compounds of formula (VI) in Scheme 1.

The compounds of formula (XXX) can be converted to compounds of formula (I) using the methods described above in connection with Scheme (1-A).

Compounds of formula (I) wherein Y is N; R$^2$ is selected from the group consisting of alkyl, cycloalkyl, alkenyl, cycloalkenyl, Ay, Het, —OR$^7$, —OAy, —OHet, —OR$^{10}$Het—S(O)$_n$R$^9$, —S(O)$_n$Ay, —S(O)$_n$Het, —S(O)$_n$NR$^7$R$^8$, —NR$^7$R$^8$, —NHHet, —NHR$^{10}$Het, —NHR$^{10}$Ay, —R$^{10}$NR$^7$R$^8$ and —R$^{10}$NR$^7$Ay; and at least one R$^6$ is selected from the group consisting of —NR$^7$R$^8$, —NR$^7$Ay, —NHHet, —NHR$^{10}$Ay and —NHR$^{10}$Het, may be conveniently prepared by the process outlined in Scheme 3 below.

Scheme 3

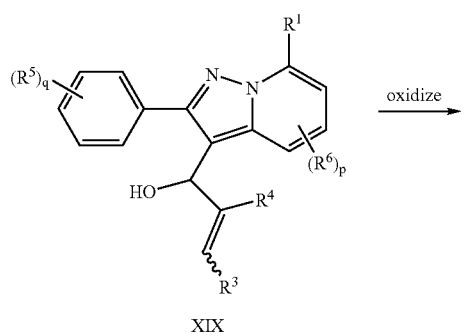

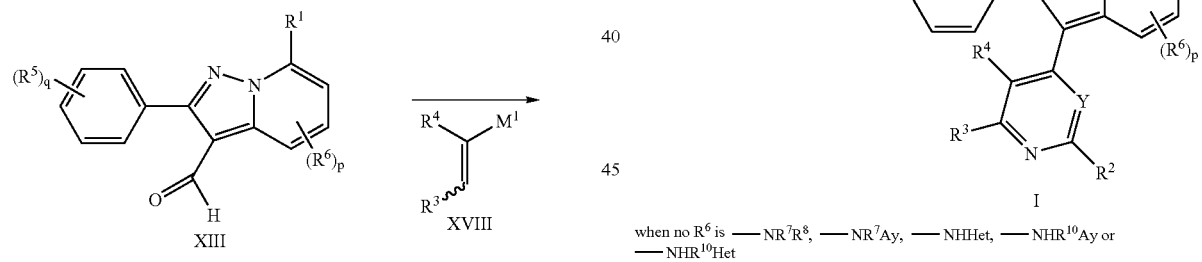

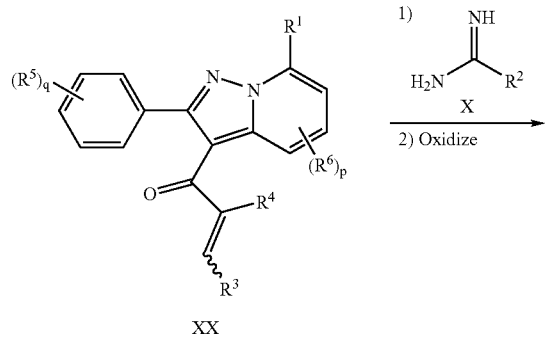

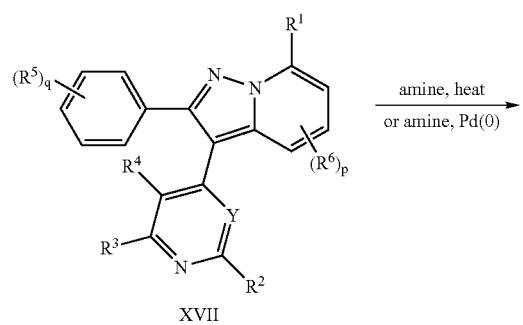

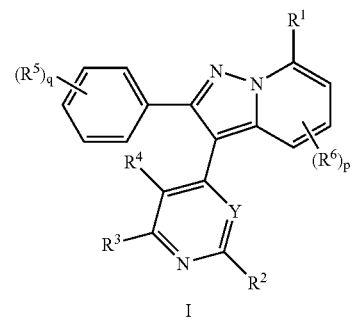

when no R$^6$ is —NR$^7$R$^8$, —NR$^7$Ay, —NHHet, —NHR$^{10}$Ay or —NHR$^{10}$Het wherein:
R$^1$ is H;
R$^2$ is selected from the group consisting of halo, alkyl, cycloalkyl, alkenyl, cycloalkenyl, Ay, Het, —OR$^7$, —OAy, —OHet, —OR$^{10}$Het, —S(O)$_n$R$^9$, —S(O)$_n$Ay, —S(O)$_n$Het, —S(O)$_n$NR$^7$R$^8$, —NR$^7$R$^8$, NHHet, —NHR$^{10}$Het, —NHR$^{10}$Ay, —R$^{10}$NR$^7$R$^8$ and —R$^{10}$NR$^7$Ay;

each R$^7$ and R$^8$ are the same or different and are independently selected from the group consisting of H, alkyl, cycloalkyl, alkenyl, cycloalkenyl, —OR$^9$, —C(O)R$^9$, —CO$_2$R$^9$, —C(O)NR$^9$R$^{11}$, —C(S)NR$^9$R$^{11}$, —C(NH)NR$^9$R$^{11}$, —SO$_2$R$^{10}$, —SO$_2$NR$^9$R$^{11}$, —R$^{10}$cycloalkyl, —R$^{10}$OR$^9$, —R$^{10}$NR$^9$R$^{11}$, —R$^{10}$C(O)R$^9$, —R$^{10}$CO$_2$R$^9$, —R$^{10}$C(O)NR$^9$R$^{11}$, —R$^{10}$C(S) NR$^9$R$^{11}$, —R$^{10}$NHC(NH)NR$^9$R$^{11}$, —R$^{10}$C(NH)

NR$^9$R$^{11}$, —R$^{10}$SO$_2$R$^{10}$, —R$^{10}$SO$_2$NR$^9$R$^{11}$, —R$^{10}$NHSO$_2$R$^9$, —R$^{10}$NHCOR$^9$ and —R$^{10}$SO$_2$NHCOR$^9$;

each R$^9$ and R$^{11}$ are the same or different and are independently selected from the group consisting of H, alkyl, cycloalkyl, —R$^{10}$cycloalkyl, —R$^{10}$OH, —R$_{10}$(OR$^{10}$)$_w$ where w is 1–10, and —R$^{10}$NR$^{10}$R$^{10}$;

each R$^{10}$ is the same or different and is independently selected from the group consisting of alkyl, cycloalkyl, alkenyl, cycloalkenyl and alkynyl;

n is 0, 1 or 2;

Ay is aryl;

Het is a 5- or 6-membered heterocyclic or heteroaryl group;

Y is N;

R$^3$ and R$^4$ are the same or different and are each independently selected from the group consisting of H, halo, alkyl, cycloalkyl, alkenyl, Ay, Het, —OR$^7$, —OAy, —C(O)R$^7$, —C(O)Ay, —CO$_2$R$^7$, —CO$_2$AY, —SO$_2$NHR$^9$, —NR$^7$R$^8$, —NR$^7$Ay, —NHHet, —NHR$^{10}$Het, —R$^{10}$OR$^7$, —R$^{10}$OAy, —R$^{10}$NR$^7$R$^8$ and —R$^{10}$NR$^7$Ay;

q is 0, 1, 2, 3, 4 or 5;

each R$^5$ is the same or different and is independently selected from the group consisting of halo, alkyl, cycloalkyl, alkenyl, cycloalkenyl, alkynyl, Ay, Het, —OR$^7$, —OAy, —OHet, —C(O)R$^9$, —CO$_2$R$^9$, —C(O)NR$^7$R$^8$, —C(O)Ay, —C(O)NR$^7$Ay, —C(O)Het, —C(O)NHR$^{10}$Het, —C(S)NR$^9$R$^{11}$, —C(NH)NR$^7$R$^8$, —C(NH)NR$^7$Ay, —S(O)$_n$R$^9$, —S(O)$_2$NR$^7$R$^8$, —S(O)$_2$NR$^7$Ay, —NR$^7$R$^8$, —NR$^7$Ay, —NHHet, —NHR$^{10}$Ay, —NHR$^{10}$Het, —R$^{10}$cycloalkyl, —R$^{10}$OR$^9$, —R$^{10}$NR$^7$R$^8$, —R$^{10}$NR$^7$Ay, —R$^{10}$C(O)R$^9$, —R$^{10}$CO$_2$R$^9$, —R$^{10}$C(O)NR$^9$R$^{11}$, —R$^{10}$C(S)NR$^9$R$^{11}$, —R$^{10}$NHC(NH)NR$^9$R$^{11}$, —R$^{10}$C(NH)NR$^9$R$^{11}$, —R$^{10}$SO$_2$R$^9$, —R$^{10}$SO$_2$NHCOR$^9$, —R$^{10}$SO$_2$NR$^9$R$^{11}$, cyano, nitro and azido; or two adjacent R$^5$ groups together with the atoms to which they are bonded form a C$_{5-6}$ cycloalkyl or aryl;

p is 1, 2 or 3; and each R$^6$ is the same or different and is independently selected from the group consisting of halo, alkyl, cycloalkyl, alkenyl, cycloalkenyl, alkynyl, Ay, Het, —OR$^7$, —OAy, —OHet, —OR$^{10}$Ay, —OR$^{10}$Het, —C(O)R$^9$, —CO$_2$R$^9$, —C(O)NR$^7$R$^9$, —C(O)Ay, —C(O)NR$^7$Ay, —C(O)NHR$^{10}$Ay, —C(O)Het, —C(O)NHR$^{10}$Het, —C(S)NR$^9$R$^{11}$, —C(NH)NR$^7$R$^8$, —C(NH)NR$^7$Ay, —S(O)$_n$R$^9$, —S(O)$_n$Ay, —S(O)$_n$Het, —S(O)$_2$NR$^7$R$^8$, —S(O)$_2$NR$^7$Ay, —NR$^7$R$^8$, —NR$^7$Ay, —NHR$^{10}$Ay, —NHHet, —NHR$^{10}$Het, —R$^{10}$cycloalkyl, —R$^{10}$Ay, —R$^{10}$Het, —R$^{10}$OR$^9$, —R$^{10}$—O—C(O)R$^9$, —R$^{10}$—O—C(O)Ay, —R$^{10}$—O—C(O)Het, —R$^{10}$—O—S(O)$_n$R$^9$, —R$^{10}$NR$^7$R$^8$, —R$^{10}$NR$^7$Ay, —R$^{10}$C(O)R$^9$, —R$^{10}$CO$_2$R$^9$, —R$^{10}$C(O)NR$^9$R$^{11}$, —R$^{10}$C(S)NR$^9$R$^{11}$, —R$^{10}$NHC(NH)NR$^9$R$^{11}$, —R$^{10}$C(NH)NR$^9$R$^{11}$, —R$^{10}$SO$_2$R$^9$, —R$^{10}$SO$_2$NHCOR$^9$, —R$^{10}$SO$_2$NR$^9$R$^{11}$, cyano, nitro and azido; or two adjacent R$^6$ groups together with the atoms to which they are bonded form a C$_{5-6}$ cycloalkyl or a 5- or 6-membered heterocyclic group containing 1 or 2 heteroatoms;

wherein in the compounds of formulas (XIII), (XIX), (XX) and (VII) at least one R$^6$ is selected from the group consisting of halo, —NR$^7$R$^8$, —NR$^7$Ay, —NHHet, —NHR$^{10}$Ay and —NHR$^{10}$Het;

wherein in the compounds of formula (I) at least one R$^6$ is selected from the group consisting of —NR$^7$R$^8$, —NR$^7$Ay, —NHHet, —NHR$^{10}$Ay and —NHR$^{10}$Het; and M$^1$ is Li, Mg-halide or cerium-halide, wherein halide is halo.

Generally, the process for preparing compounds of formula (I) wherein Y is N; R$^2$ is selected from the group consisting of alkyl, cycloalkyl, alkenyl, cycloalkenyl, Ay, Het, —OR$^7$, —OAy, —OHet, —OR$^{10}$Het—S(O)$_n$R$^9$, —S(O)$_n$Ay, —S(O)$_n$Het, —S(O)$_n$NR$^7$R$^8$, —NR$^7$R$^8$, —NHHet, —NHR$^{10}$Het, —NHR$^{10}$Ay, —R$^{10}$NR$^7$R$^8$ and —R$^{10}$NR$^7$Ay; and at least one R$^6$ is selected from the group consisting of —NR$^7$R$^8$, —NR$^7$Ay, —NHHet, —NHR$^{10}$Ay and —NHR$^{10}$Het, (all formulas and all other variables having been defined above in connection with Scheme 3), comprises the following steps:

(a) reacting a picoline of formula (XI) with a benzoylating agent of formula (II) to prepare a compound of formula (III);

(b) reacting the compound of formula (III) with a hydroxylamine source to prepare a compound of formula (IV);

(c) reacting the compound of formula (IV) with an acylating or sulfonylating agent to prepare a compound of formula (V);

(d) rearranging the compound of formula (V) to prepare a compound of formula (VI);

(e) formylating the compound of formula (VI) to prepare a compound of formula (XIII);

(f) reacting a compound of formula (XIII) with a compound of formula (XVIII) to prepare a compound of formula (XIX);

(g) oxidizing the compound of formula (XIX) to prepare a compound of formula (XX);

(h) reacting a compound of formula (XX) with a compound of formula (X) followed by oxidative aromatization to prepare the compound of formula (XVII); and (i) in the embodiment wherein no R$^6$ is selected from the group consisting of —NR$^7$R$^8$, —NR$^7$Ay, —NHHet, —NHR$^{10}$Ay and —NHR$^{10}$Het (i.e., R$^6$ halo) replacing the R$^6$ halo of the compound of formula (XVII) with an amine substituent selected from the group consisting of —NR$^7$R$^8$, —NR$^7$Ay, —NHHet, —NHR$^{10}$Ay and —NHR$^{10}$Het to prepare a compound of formula (I).

More specifically, wherein no R$^6$ in the compound of formula (XVII) is selected from the group consisting of —NR$^7$R$^8$, —NR$^7$Ay, —NHHet, —NHR$^{10}$Ay and —NHR$^{10}$Het (i.e., said at least one R$^6$ is halo; "R$^6$ halo"), the compounds of formula (I) wherein Y is N; R$^2$ is selected from the group consisting of alkyl, cycloalkyl, alkenyl, cycloalkenyl, Ay, Het, —OR$^7$, —OAy, —OHet, —OR$^{10}$Het—S(O)$_n$R$^9$, —S(O)$_n$Ay, —S(O)$_n$Het, —S(O)$_n$NR$^7$R$^8$, —NR$^7$R$^8$, —NHHet, —NHR$^{10}$Het, —NHR$^{10}$Ay, —R$^{10}$NR$^7$R$^8$ and —R$^{10}$NR$^7$Ay; and at least one R$^6$ is selected from the group consisting of —NR$^7$R$^8$, —NR$^7$Ay, —NHHet, —NHR$^{10}$Ay and —NHR$^{10}$Het, can be prepared by replacing the R$^6$ halo on the compound of formula (XVII) with an amine substituent selected from the group consisting of —NR$^7$R$^8$, —NR$^7$Ay, —NHHet, —NHR$^{10}$Ay and —NHR$^{10}$Het. Methods for the conversion of compounds of formula (XVII) to compounds of formula (I) are described above in connection with the synthesis according to Scheme 2.

Compounds of formula (XVII) can be prepared by reacting a compound of formula (XX) with a compound of formula (X) followed by oxidative aromatization.

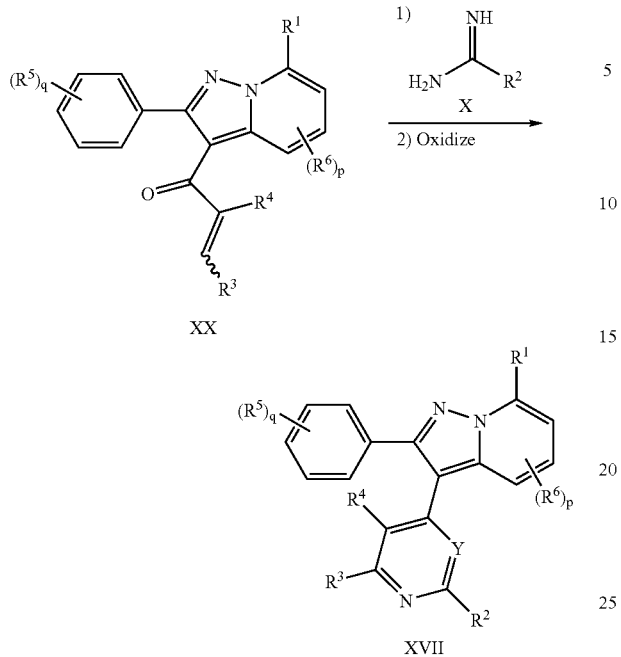

XX

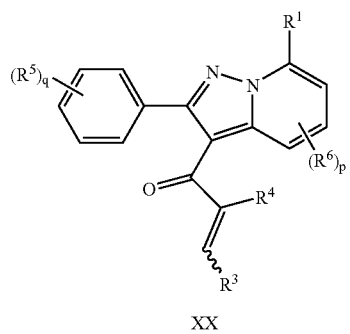

XVII wherein all variables are as defined above in connection with Scheme 3.

The condensation is conveniently carried out by treating the compound of formula (XX) with a compound of formula (X) in an inert solvent, optionally in the presence of a base. The reaction may be heated to 50–150° C. or performed at ambient temperature. Suitable inert solvents include lower alcohols such as, for example, methanol, ethanol, isopropanol and the like. The base is typically sodium alkoxide, potassium carbonate, or an amine base such as triethylamine. In another embodiment, the solvent is N,N-dimethylformamide and the base is potassium carbonate, or an amine base such as triethylamine. The reaction produces a dihydropyrimidine intermediate.

Preferably in the same reaction vessel, the dihydropyrimidine intermediate may be oxidized to a compound of formula (I) by the addition of an oxidizing agent The reaction may be heated to 50–150° C. or performed at ambient temperature. Preferably, the oxidizing agent is oxygen ($O_2$), palladium on carbon, 2,3-dichloro-5,6dicyano-1,4-benzoquinone, or the like.

Compounds of formula (XX) may be conveniently prepared by oxidation of compounds of formula (XIX).

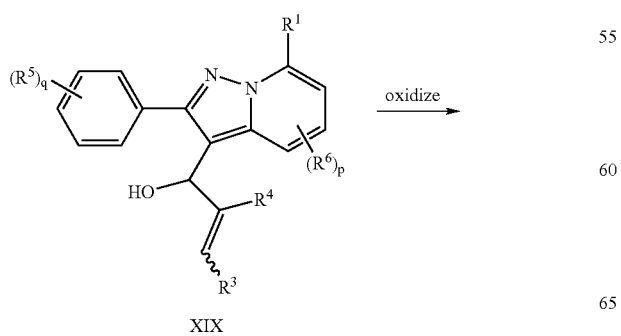

XIX wherein all variables are as defined above in connection with Scheme 3.

Preferred oxidizing agents for the oxidation of compounds of formula (XIX) include but are not limited to manganese dioxide, and the like. The oxidation is typically carried out in an inert solvent such as for example, dichloromethane, chloroform, N,N-dimethylformamide, ether, and the like.

Compounds of formula (XIX) may be conveniently prepared by reacting a compound of formula (XIII) with a compound of formula (XVIII).

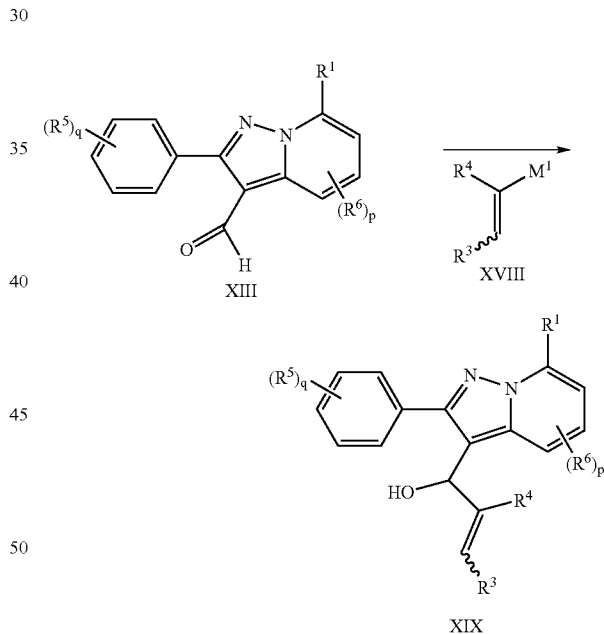

wherein $M^1$ is a metal such as for example, lithium, magnesium(II) halides, cerium(III) halides, and the like and all other variables are as defined above in connection with Scheme 3. Compounds of formula (XVIII) may be purchased from commercial sources or prepared by methods known to one skilled in the art. The compounds of formula (XIII) may be prepared using the methods described above in connection with Scheme 2 above.

In addition to the foregoing process for preparing certain compounds of formula (I), the present invention also provides certain intermediate compounds for use in the preparation of such compounds of formula (I) according to the foregoing process. Such intermediates are depicted in Scheme 3 above.

In another embodiment, compounds of formula (I) wherein Y is N; and $R^2$ is selected from the group consisting of alkyl, cycloalkyl, alkenyl, cycloalkenyl, Ay, Het, —$OR^7$, —OAy, —OHet, —$OR^{10}$Het, —$S(O)_nR^9$, —$S(O)_n$Ay, —$S(O)_n$Het, —$S(O)NR^7R^8$, —$NR^7R^8$, —NH Het, —$NHR^{10}$Het, —$NHR^{10}$Ay, —$R^{10}NR^7R^8$ and —$R^{10}NR^7$Ay, may be conveniently prepared by the process outlined in Scheme 3-A below.

Scheme 3-A

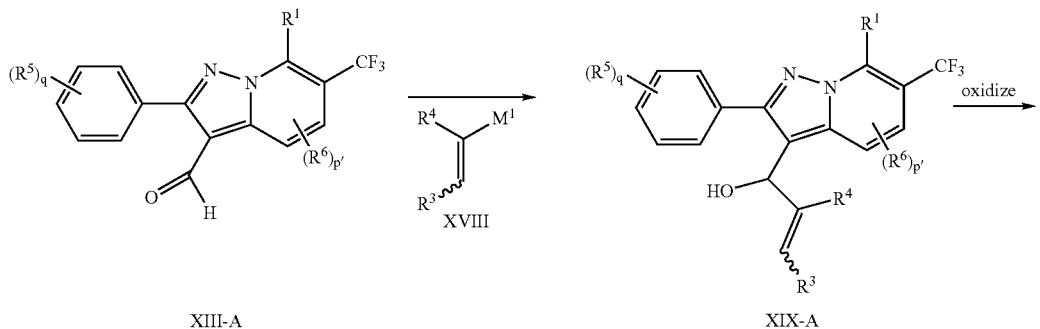

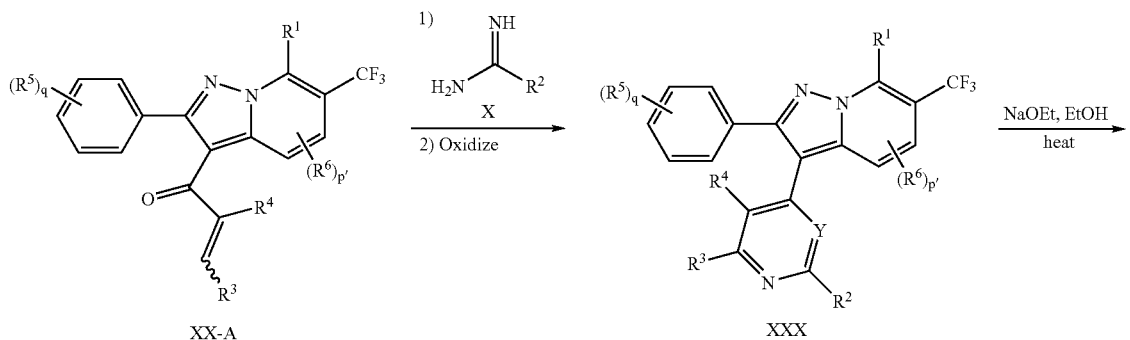

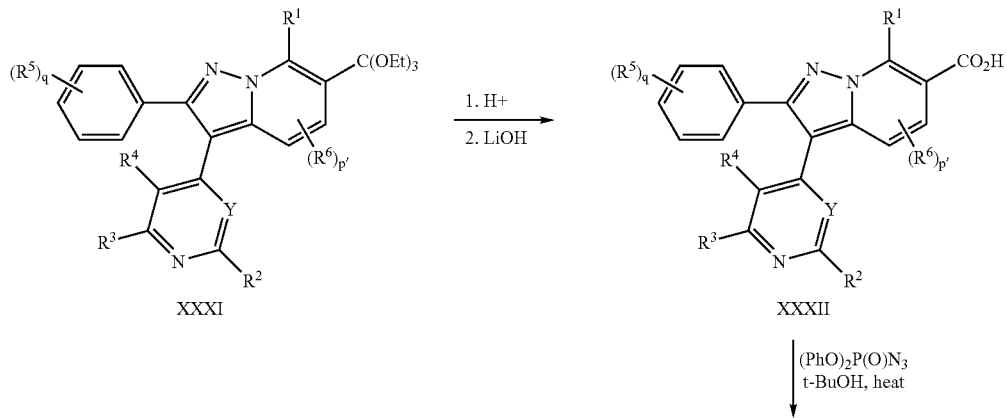

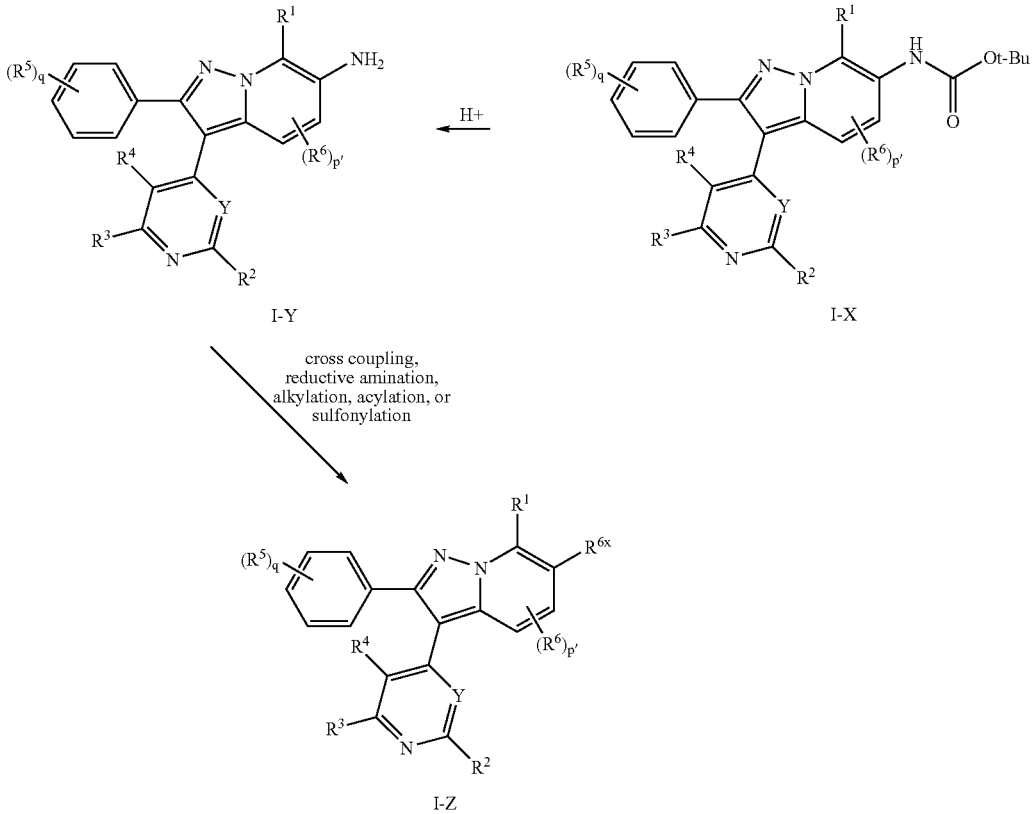

wherein:

R[1] is H;

R[2] is selected from the group consisting of halo, alkyl, cycloalkyl, alkenyl, cycloalkenyl, Ay, Het, —OR[7], —OAy, —OHet, —OR[10]Het, —S(O)$_n$R[9], —S(O)$_n$Ay, —S(O)$_n$Het, —S(O)$_n$NR[7]R[8], —NR[7]R[8], NHHet, —NHR[10]Het, —NHR[10]Ay, —R[10]NR[7]R[8] and —R[10]NR[7]Ay;

each R[7] and R[8] are the same or different and are independently selected from the group consisting of H, alkyl, cycloalkyl, alkenyl, cycloalkenyl, —OR[9], —C(O)R[9], —CO$_2$R[9], —C(O)NR[9]R[11], —C(S)NR[9]R[11], —C(NH)NR[9]R[11], —SO$_2$R[10], —SO$_2$NR[9]R[11], —R[10]cycloalkyl, —R[10]OR[9], —R[10]NR[9]R[11], —R[10]C(O)R[9], —R[10]CO$_2$R[9], —R[10]C(O)NR[9]R[11], —R[10]C(S)NR[9]R[11], —R[10]NHC(NH)NR[9]R[11], —R[10]C(NH)NR[9]R[11], —R[10]SO$_2$R[10], —R[10]SO$_2$NR[9]R[11], —R[10]NHSO$_2$R[9], —R[10]NHCOR[9] and —R[10]SO$_2$NHCOR[9];

each R[9] and R[11] are the same or different and are independently selected from the group consisting of H, alkyl, cycloalkyl, —R[10]cycloalkyl, —R[10]OH, —R[10](OR[10])$_w$ where w is 1–10, and —R[10]NR[10]R[10];

each R[10] is the same or different and is independently selected from the group consisting of alkyl, cycloalkyl, alkenyl, cycloalkenyl and alkynyl;

n is 0, 1 or 2;

Ay is aryl;

Het is a 5- or 6-membered heterocyclic or heteroaryl group;

Y is N;

R[3] and R[4] are the same or different and are each independently selected from the group consisting of H, halo, alkyl, cycloalkyl, alkenyl, Ay, Het, —OR[7], —OAy, —C(O)R[7], —C(O)Ay, —CO$_2$R[7], —CO$_2$Ay, —SO$_2$NHR[9], —NR[7]R[8], —NR[7]Ay, —NHHet, —NHR[10]Het, —R[10]OR[7], —R[10]OAy, —R[10]NR[7]R[8] and R[10]NR[7]Ay;

q is 0, 1, 2, 3, 4 or 5;

each R[5] is the same or different and is independently selected from the group consisting of halo, alkyl, cycloalkyl, alkenyl, cycloalkenyl, alkynyl, Ay, Het, —OR[7], —OAy, —OHet, —C(O)R[9], —CO$_2$R[9], —C(O)NR[7]R[8], —C(O)Ay, —C(O)NR[7]Ay, —C(O)Het, —C(O)NHR[10]Het, —C(S)NR[9]R[11], —C(NH)NR[7]R[8], —C(NH)NR[7]Ay, —S(O)$_n$R[9], —S(O)$_2$NR[7]R[8], —S(O)$_2$NR[7]Ay, —NR[7]R[8], —NR[7]Ay, —NHHet, —NHR[10]Ay, —NHR[10]Het, —R[10]cycloalkyl, —R[10]OR[9], —R[10]NR[7]R[8], —R[10]NR[7]Ay, —R[10]C(O)R[9], —R[10]CO$_2$R[9], —R[10]C(O)NR[9]R[11], —R[10]C(S)NR[9]R[11], —R[10]NHC(NH)NR[9]R[11], —R[10]C(NH)NR[9]R[11], —R[10]SO$_2$R[9], —R[10]SO$_2$NHCOR[9], —R[10]SO$_2$NR[9]R[11], cyano, nitro and azido; or two adjacent R[5] groups together with the atoms to which they are bonded form a $C_{5-6}$ cycloalkyl or aryl;

p' is 1, 2 or 3; and each R[6] is the same or different and is independently selected from the group consisting of halo, alkyl, cycloalkyl, alkenyl, cycloalkenyl, alkynyl, Ay, Het, —OR[7], —OAy, —OHet, —OR[10]Ay, —OR[10]Het, —C(O)R[9], —CO$_2$R[9], —C(O)NR[7]R[9], —C(O)Ay, —C(O)NR[7]Ay, —C(O)NHR[10]Ay, —C(O)Het, —C(O)NHR[10]Het, —C(S)NR[9]R[11], —C(NH)NR[7]R[8], —C(NH)NR[7]Ay, —S(O)$_n$R[9], —S(O)$_n$Ay, —S(O)$_n$Het, —S(O)$_2$NR$^7$R$^8$, —S(O)$_2$NR$^7$Ay, —NR$^7$R$^8$, —NR$^7$Ay, —NHR$^{10}$Ay, —NHHet, —NHR$^{10}$Het, —R$^{10}$cycloalkyl, —R$^{10}$Ay, —R$^{10}$Het, —R$^{10}$OR$^9$, —R$^{10}$—O—C(O)R$^9$, —R$^{10}$—O—C(O)Ay, —R$^{10}$—O—C(O)Het, —R$^{10}$—O—S(O)$_n$R$^9$, —R$^{10}$NR$^7$R$^8$, —R$^{10}$NR$^7$Ay, —R$^{10}$C(O)R$^9$, —R$^{10}$CO$_2$R$^9$, —R$^{10}$C(O)NR$^9$R$^{11}$, —R$^{10}$C(S)NR$^9$R$^{11}$, —R$^{10}$NHC(NH)NR$^9$R$^{11}$, —R$^{10}$C(NH)NR$^9$R$^{11}$, —R$^{10}$SO$_2$R$^9$, —R$^{10}$SO$_2$NHCOR$^9$, —R$^{10}$SO$_2$NR$^9$R$^{11}$, cyano, nitro and azido; or two adjacent R$^6$ groups together with the atoms to which they are bonded form a C$_{5-6}$ cycloalkyl or a 5- or 6-membered heterocyclic group containing 1 or 2 heteroatoms;

R$^{6x}$ is selected from the group consisting of —NR$^7$R$^8$ where R$^7$ and R$^8$ are not both H, —NR$^7$Ay, —NHHet, —NHR$^{10}$Het and —NHR$^{10}$Ay; and M$^1$ is Li, Mg-halide or cerium-halide, wherein halide is halo.

Generally, the process for preparing compounds of formula (I) wherein Y is N; and R$^2$ is selected from the group consisting of alkyl, cycloalkyl, alkenyl, cycloalkenyl, Ay, Het, —OR$^7$, —OAy, —OHet, —OR$^{10}$Het—S(O)$_n$R$^9$, —S(O)$_n$Ay, —S(O)$_n$Het, —S(O)$_n$NR$^7$R$^8$, —NR$^7$R$^8$, —NHHet, —NHR$^{10}$Het, —NHR$^{10}$Ay, —R$^{10}$NR$^7$R$^8$ and —R$^{10}$NR$^7$Ay, (all formulas and all other variables having been defined above in connection with Scheme 3-A), comprises the following steps:

(a) reacting a 2-chloro-5-trifluoromethylpyridine of formula (XI-A) with an acetophenone of formula (XXVII) to prepare a compound of formula (III-A);
(b) reacting the compound of formula (III-A) with a hydroxylamine source to prepare a compound of formula (IV-A);
(c) reacting the compound of formula (IV-A) with an acylating or sulfonylating agent to prepare a compound of formula (V-A);
(d) rearranging the compound of formula (V-A) to prepare a compound of formula (VI-A);
(e) formylating the compound of formula (VI-A) to prepare a compound of formula (XIII-A);
(f) reacting the compound of formula (XIII-A) with a compound of formula (XVIII) to prepare a compound of formula (XIX-A);
(g) oxidizing the compound of formula (XIX-A) to prepare a compound of formula (XX-A);
(h) reacting a compound of formula (XX-A) with a compound of formula (X) followed by oxidative aromatization to prepare a compound of formula (XXX);
(i) reacting the compound of formula (XXX) with sodium ethoxide to prepare a compound of formula (XXXI);
(j) reacting the compound of formula (XXXI) with an acid, followed by hydrolysis of the resulting ester to give a compound of formula (XXXII);
(k) reacting the compound of formula (XXXII) with diphenylphosphoryl azide in tert-butanol to give a compound of formula (I-X);
(l) optionally cleaving the compound of formula (I-X) to give a compound of formula (I-Y); and
(m) optionally converting the compound of formula (I-Y) to a compound of formula (I-Z) using conditions selected from the group consisting of cross coupling, reductive amination, alkylation, acylation and sulfonylation.

More specifically, compounds of formula (I) wherein Y is N; and R$^2$ is selected from the group consisting of alkyl, cycloalkyl, alkenyl, cycloalkenyl, Ay, Het, —OR$^7$, —OAy, —OHet, —OR$^{10}$Het—S(O)$_n$R$^9$, —S(O)Ay, —S(O)$_n$Het, —S(O)$_n$NR$^7$R$^8$, —NR$^7$R$^8$, —NHHet, —NHR$^{10}$Het, —NHR$^{10}$Ay, —R$^{10}$NR$^7$R$^8$ and —R$^{10}$NR$^7$Ay, can be prepared by converting a compound of formula (XXX) to a compound of formula (I) using the methods described above in connection with the process of Scheme 1-A.

Compounds of formula (XXX) can be prepared using methods analogous to those described above for the preparation of compounds of formula (XVII) according to Scheme 3, with the exception that the first step (i.e., the preparation of compounds of formula (III-A)) involves the condensation of 2-chloro-5-trifluoromethylpyridine with the acetophenone of formula (XXVII) under basic conditions, in place of the reaction of the picoline of formula (XI) with the benzoylating agent of formula (II) as is employed in the synthesis of compounds of formula (VI) as described in Scheme 1.

The compounds of formula (XXX) can be converted to compounds of formula (I) using the methods described above in connection with Scheme (1-A).

Compounds of formula (I), may be conveniently prepared by the process outlined in Scheme 4 below.

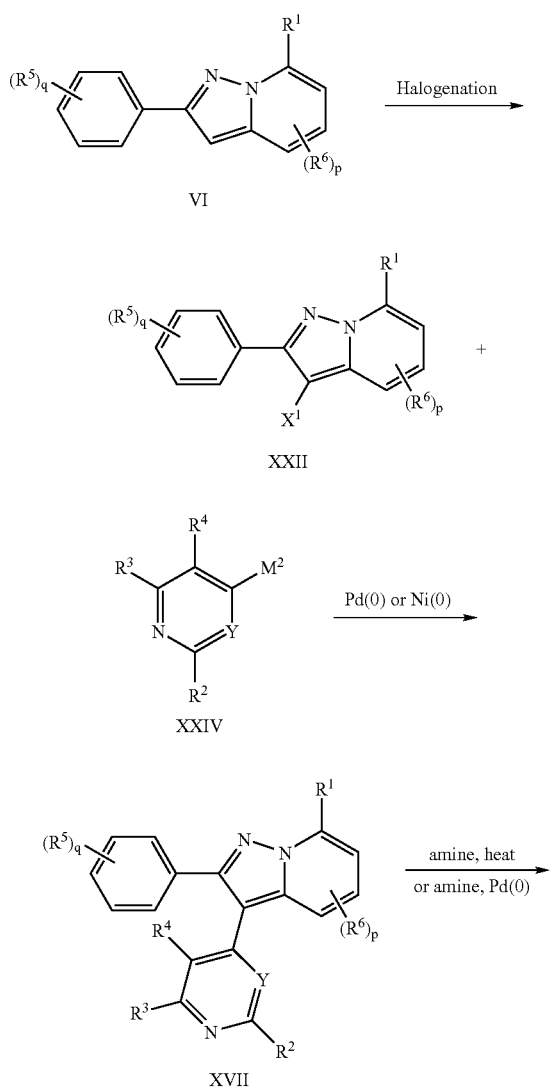

-continued

![Structure of formula I showing phenyl group with (R^5)_q substituents, connected to pyrazolopyridine core with R^1, R^4, R^3, and (R^6)_p substituents, with Y and R^2 groups]

when no $R^6$ is —NR$^7$R$^8$, —NR$^7$Ay, —NHHet, —NHR$^{10}$Ay, or —NHR$^{10}$Het

I wherein:

$R^1$ is H;

$R^2$ is selected from the group consisting of halo, alkyl, cycloalkyl, alkenyl, cycloalkenyl, Ay, Het, —OR$^7$, —OAy, —OHet, —OR$^{10}$Het, —S(O)$_n$R$^9$, —S(O)$_n$Ay, —S(O)$_n$Het, —S(O)$_n$NR$^7$R$^8$, —NR$^7$R$^8$, —NHHet, —NHR$^{10}$Het, —NHR$^{10}$Ay, —R$^{10}$NR$^7$R$^8$ and —R$^{10}$NR$^7$Ay;

each $R^7$ and $R^8$ are the same or different and are independently selected from the group consisting of H, alkyl, cycloalkyl, alkenyl, cycloalkenyl, —OR$^9$, —C(O)R$^9$, —CO$_2$R$^9$, —C(O)NR$^9$R$^{11}$, —C(S)NR$^9$R$^{11}$, —C(NH)NR$^9$R$^{11}$, —SO$_2$R$^{10}$, —SO$_2$NR$^9$R$^{11}$, —R$^{10}$cycloalkyl, —R$^{10}$OR$^9$, —R$^{10}$NR$^9$R$^{11}$, —R$^{10}$C(O)R$^9$, —R$^{10}$CO$_2$R$^9$, —R$^{10}$C(O)NR$^9$R$^{11}$, —R$^{10}$C(S)NR$^9$R$^{11}$, —R$^{10}$NHC(NH)NR$^9$R$^{11}$, —R$^{10}$C(NH)NR$^9$R$^{11}$, —R$^{10}$SO$_2$R$^{10}$, —R$^{10}$SO$_2$NR$^9$R$^{11}$, —R$^{10}$NHSO$_2$R$^9$, —R$^{10}$NHCOR$^9$ and —R$^{10}$SO$_2$NHCOR$^9$;

each $R^9$ and $R^{11}$ are the same or different and are independently selected from the group consisting of H, alkyl, cycloalkyl, —R$^{10}$cycloalkyl, —R$^{10}$OH, —R$^{10}$(OR$^{10}$)$_w$ where w is 1–10, and —R$^{10}$NR$^{10}$R$^{10}$;

each $R^{10}$ is the same or different and is independently selected from the group consisting of alkyl, cycloalkyl, alkenyl, cycloalkenyl and alkynyl;

n is 0, 1 or 2;

Ay is aryl;

Het is a 5- or 6-membered heterocyclic or heteroaryl group;

Y is N or CH;

$R^3$ and $R^4$ are the same or different and are each independently selected from the group consisting of H, halo, alkyl, cycloalkyl, alkenyl, Ay, Het, —OR$^7$, —OAy, —C(O)R$^7$, —C(O)Ay, —CO$_2$R$^7$, —CO$_2$Ay, —SO$_2$NHR$^9$, —NR$^7$R$^8$, —NR$^7$Ay, —NHHet, —NHR$^{10}$Het, —R$^{10}$OR$^7$, —R$^{10}$OAy, —R$^{10}$NR$^7$R$^8$ and R$^{10}$NR$^7$Ay;

q is 0, 1, 2, 3, 4 or 5;

each $R^5$ is the same or different and is independently selected from the group consisting of halo, alkyl, cycloalkyl, alkenyl, cycloalkenyl, alkynyl, Ay, Het, —OR$^7$, —OAy, —OHet, —C(O)R$^9$, —CO$_2$R$^9$, —C(O)NR$^7$R$^8$, —C(O)Ay, —C(O)NR$^7$Ay, —C(O)Het, —C(O)NHR$^{10}$Het, —C(S)NR$^9$R$^{11}$, —C(NH)NR$^7$R$^8$, —C(NH)NR$^7$Ay, —S(O)$_n$R$^9$, —S(O)$_2$NR$^7$R$^8$, —S(O)$_2$NR$^7$Ay, —NR$^7$R$^8$, —NR$^7$Ay, —NHHet, —NHR$^{10}$Ay, —NHR$^{10}$Het,
—R$^{10}$cycloalkyl, —R$^{10}$OR$^9$, —R$^{10}$NR$^7$R$^8$, —R$^{10}$NR$^7$Ay, —R$^{10}$C(O)R$^9$, —R$^{10}$CO$_2$R$^9$, —R$^{10}$C(O)NR$^9$R$^{11}$, —R$^{10}$C(S)NR$^9$R$^{11}$, —R$^{10}$NHC(NH)NR$^9$R$^{11}$, —R$^{10}$C(NH)NR$^9$R$^{11}$, —R$^{10}$SO$_2$R$^9$, —R$^{10}$SO$_2$NHCOR$^9$, —R$^{10}$SO$_2$NR$^9$R$^{11}$, cyano, nitro and azido; or two adjacent $R^5$ groups together with the atoms to which they are bonded form a $C_{5-6}$ cycloalkyl or aryl;

p is 1, 2 or 3; and each $R^6$ is the same or different and is independently selected from the group consisting of halo, alkyl, cycloalkyl, alkenyl, cycloalkenyl, alkynyl, Ay, Het, —OR$^7$, —OAy, —OHet, —OR$^{10}$Ay, —OR$^{10}$Het, —C(O)R$^9$, —CO$_2$R$^9$, —C(O)NR$^7$R$^9$, —C(O)Ay, —C(O)NR$^7$Ay, —C(O)NHR$^{10}$Ay, —C(O)Het, —C(O)NHR$^{10}$Het, —C(S)NR$^9$R$^{11}$, —C(NH)NR$^7$R$^8$, —C(NH)NR$^7$Ay, —S(O)$_n$R$^9$, —S(O)$_n$Ay, —S(O)$_n$Het, —S(O)$_2$NR$^7$R$^8$, —S(O)$_2$NR$^7$Ay, —NR$^7$R$^8$, —NR$^7$Ay, —NHR$^{10}$Ay, —NHHet, —NHR$^{10}$Het, —R$^{10}$cycloalkyl, —R$^{10}$Ay, —R$^{10}$Het, —R$^{10}$OR$^9$, —R$^{10}$—O—C(O)R$^9$, —R$^{10}$—O—C(O)Ay, —R$^{10}$—O—C(O)Het, —R$^{10}$—O—S(O)$_n$R$^9$, —R$^{10}$NR$^7$R$^8$, —R$^{10}$NR$^7$Ay, —R$^{10}$C(O)R$^9$, —R$^{10}$CO$_2$R$^9$, —R$^{10}$C(O)NR$^9$R$^{11}$, —R$^{10}$C(S)NR$^9$R$^{11}$, —R$^{10}$NHC(NH)NR$^9$R$^{11}$, —R$^{10}$C(NH)NR$^9$R$^{11}$, —R$^{10}$SO$_2$R$^9$, —R$^{10}$SO$_2$NHCOR$^9$, —R$^{10}$SO$_2$NR$^9$R$^{11}$, cyano, nitro and azido; or two adjacent $R^6$ groups together with the atoms to which they are bonded form a $C_{5-6}$ cycloalkyl or a 5- or 6-membered heterocyclic group containing 1 or 2 heteroatoms;

wherein in the compounds of formula (VI), (XXII) and (XVII) at least one $R^6$ is selected from the group consisting of halo, —NR$^7$R$^8$, —NR$^7$Ay, —NHHet, —NHR$^{10}$Ay and —NHR$^{10}$Het; and wherein in the compounds of formula (I), at least one $R^6$ is selected from the group consisting of —NR$^7$R$^8$, —NR$^7$Ay, —NHHet, —NH R$^{10}$Ay and —NHR$^{10}$Het;

$X^1$ is chloro, bromo or iodo; and $M^2$ is —B(OH)$_2$, —B(ORa)$_2$, —B(Ra)$_2$, —Sn(Ra)$_3$, Zn-halide, ZnRa, or Mg-halide where Ra is alkyl or cycloalkyl and halide is halo.

Generally, the process for preparing compounds of formula (I) (all formulas and variables having been defined above in connection with Scheme 4), comprises the following steps:

(a) reacting a picoline of formula (XI) with a benzoylating agent of formula (II) to prepare a compound of formula (III);

(b) reacting the compound of formula (III) with a hydroxylamine source to prepare a compound of formula (IV);

(c) reacting the compound of formula (IV) with an acylating or sulfonylating agent to prepare a compound of formula (V);

(d) rearranging the compound of formula (V) to prepare a compound of formula (VI);

(e) halogenating a compound of formula (VI) to prepare a compound of formula (XXII);

(f) reacting a compound of formula (XXII) with a compound of formula (XXIV) to prepare a compound of formula (XVII); and (g) in the embodiment wherein no $R^6$ in the compound of formula (XVII) is selected from the group consisting of —NR⁷R⁸, —NR⁷Ay, —NHHet, —NHR¹⁰Ay and —NHR¹⁰Het (i.e., R⁶ halo), replacing the R⁶ halo of the compound of formula (XIII) with an amine substituent selected from the group consisting of —NR⁷R⁸, —NR⁷Ay, —NHHet, —NHR¹⁰Ay and —NHR¹⁰Het to prepare a compound of formula (I).

More specifically, when no R⁶ is selected from the group consisting of —NR⁷R⁸, —NR⁷Ay, —NHHet, —NHR¹⁰Ay and —NHR¹⁰Het (i.e., R⁶ halo), compounds of formula (I) can be prepared by replacing the R⁶ halo on the compounds of formula (XVII) with an amine substituent selected from the group consisting of —NR⁷R⁸, —NR⁷Ay, —NHHet, —NHR¹⁰Ay and —NHR¹⁰Het Methods for the conversion of compounds of formula (XVII) to compounds of formula (I) are described above in connection with the description of Scheme 2.

Compounds of formula (XVII) can be prepared by reacting a compound of formula (XXII) with a compound of formula (XXIV).

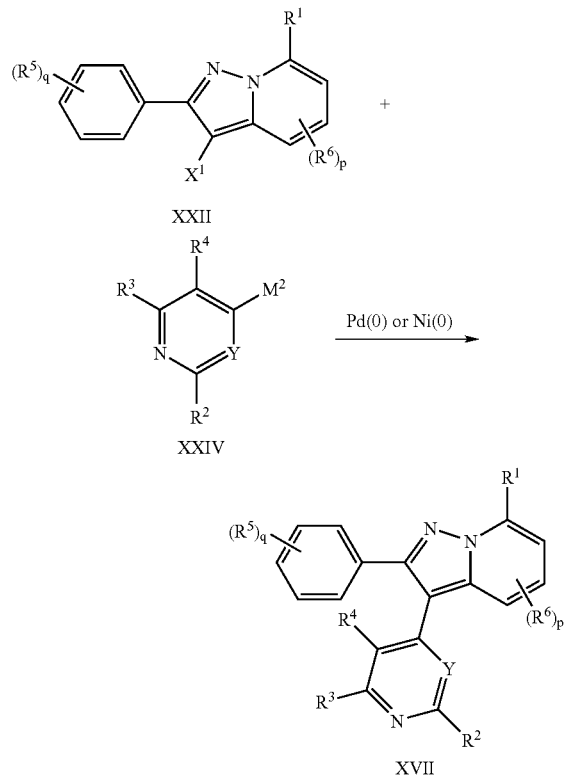

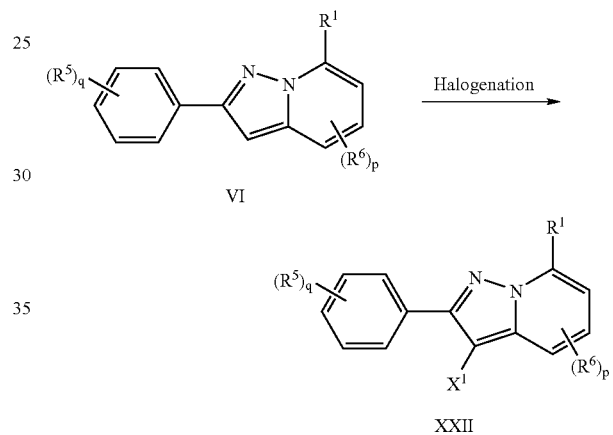

wherein all variables are as defined above in connection with Scheme 4.

The reaction may be carried out in an inert solvent, in the presence of a palladium (0) or nickel (0) catalyst The reaction may optionally be heated to about 50–150° C. Preferably the reaction is performed by reacting equimolar amounts of a compound of formula (XXII) with a Het-metal compound of formula (XXIV), but the reaction may also be performed in the presence of an excess of compound of the formula (XXIV). The palladium or nickel catalyst is preferably present in 1–10 mol/compared to the compound of formula (XXII). Examples of suitable palladium catalysts include but are not limited to, tetrakis(triphenylphosphine) palladium (0), dichlorobis(triphenylphosphine)palladium (II), tris(dibenzylidene acetone) dipalladium (0) and bis (diphenylphosphinoferrocene)palladium (II) dichloride. Suitable solvents include but are not limited to, N,N-dimethylformamide, toluene, tetrahydrofuran, dioxane, and 1-methyl-2-pyrrolidinone. When the Het-metal compound of formula (XXIV) is an arylboronic acid or ester or an arylborinate the reaction is more conveniently carried out by adding a base in a proportion equivalent to, or greater than, that of the compound of formula (XXIV). Het-metal compounds of formula (XXIV) may be obtained from commercial sources or prepared either as discreet isolated compounds or generated in situ using methods known to one skilled in the art (Suzuki, A. *J. Organomet Chem*. 1999, 576, 147; Stille, J. *Angew. Chem. Int. Ed. Engl*. 1986, 25, 508; Snieckus, V. *J. Org. Chem*. 1995, 60, 292.)

Compounds of formula (XXII) can be prepared from compounds of formula (VI) by a halogenation procedure.

wherein all variables are as defined above in connection with Scheme 4.

Typically, the halogenation reaction is carried out by subjecting the compounds of formula (VI) to a halogenating agent in a suitable solvent. Suitable halogenating agents include but are not limited to, N-bromosuccinimide, trialkylammonium tribromides, bromine, N-chlorosuccinimide, N-iodosuccinimide, iodine monochloride, and the like. Suitable solvents include, for example, N,N-dimethylformamide, tetrahydrofuran, dioxane, 1-methyl-2-pyrrolidinone, carbon tetrachloride, toluene, dichloromethane, diethyl ether, and the like.

The compounds of formula (VI) may be prepared according to the methods described above in connection with Scheme 1.

In addition to the foregoing process for preparing compounds of formula (I), the present invention also provides certain intermediate compounds for use in the preparation of compounds of formula (I) according to the foregoing process. Such intermediates are depicted in Scheme 4 above.

In yet another embodiment of the present invention, compounds of formula (I) may be conveniently prepared by the process outlined in Scheme 4-A below.

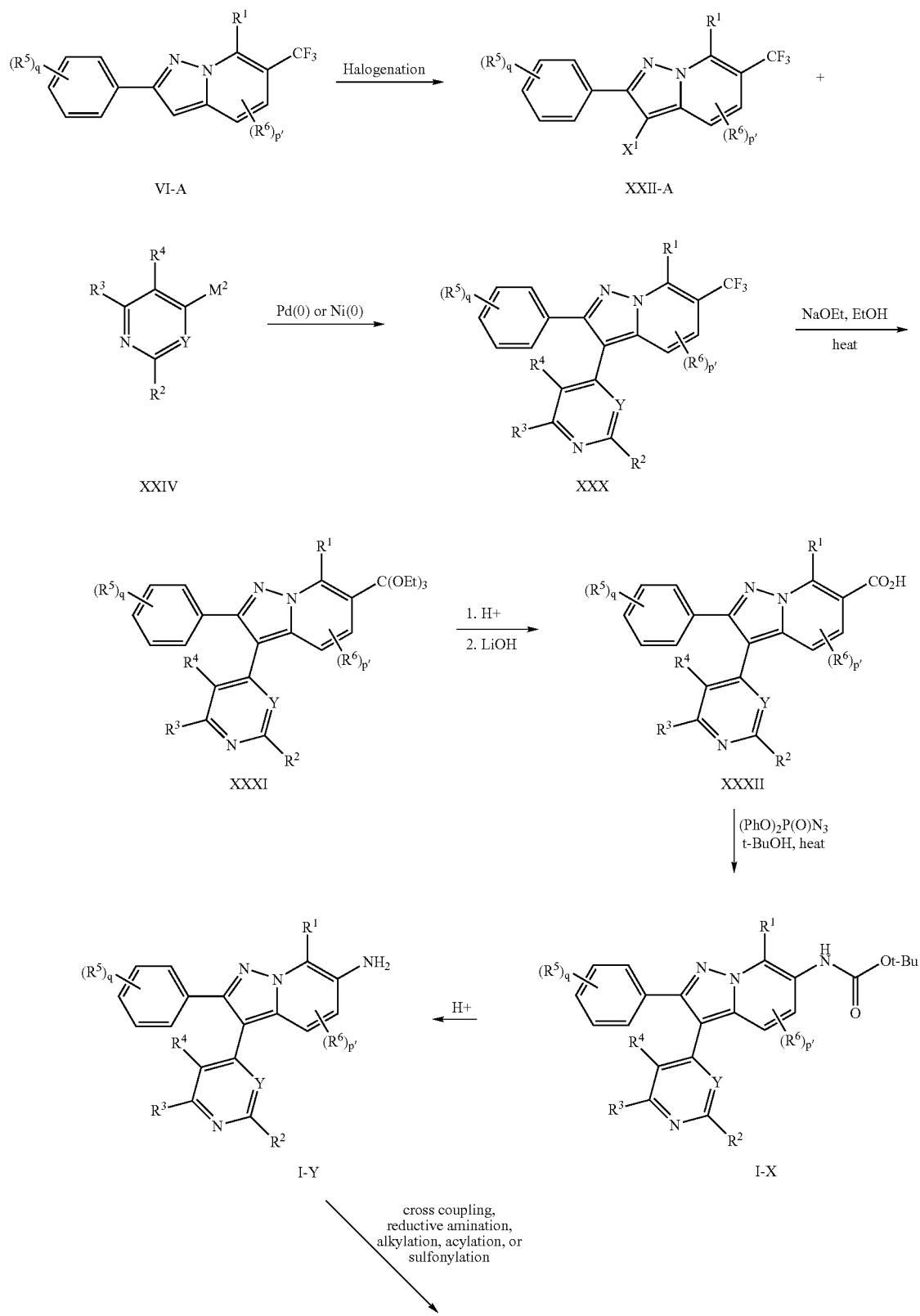

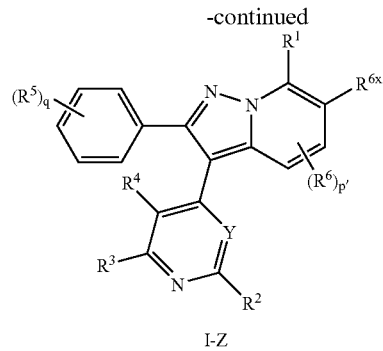

I-Z wherein:
R¹ is H;
R² is selected from the group consisting of halo, alkyl, cycloakyl, alkenyl, cycloalkenyl, Ay, Het, —OR⁷, —OAy, —OHet, —OR¹⁰Het, —S(O)$_n$R⁹, —S(O)$_n$Ay, —S(O)$_n$Het, —S(O)$_n$NR⁷R⁸, —NR⁷R⁸, —NHHet, —NHR¹⁰Het, —NHR¹⁰Ay, —R¹⁰NR⁷R⁸ and —R¹⁰NR⁷Ay;

each R⁷ and R⁸ are the same or different and are independently selected from the group consisting of H, alkyl, cycloalkyl, alkenyl, cycloalkenyl, —OR⁹, —C(O)R⁹, —CO₂R⁹, —C(O)NR⁹R¹¹, —C(S)NR⁹R¹¹, —C(NH)NR⁹R¹¹, —SO₂R¹⁰, —SO₂NR⁹R¹¹, —R¹⁰cycloalkyl, —R¹⁰OR⁹, —R¹⁰NR⁹R¹¹, —R¹⁰C(O)R⁹, —R¹⁰CO₂R⁹, —R¹⁰C(O)NR⁹R¹¹, —R¹⁰C(S)NR⁹R¹¹, —R¹⁰NHC(NH)NR⁹R¹¹, —R¹⁰C(NH)NR⁹R¹¹, —R¹⁰SO₂R¹⁰, —R¹⁰SO₂NR⁹R¹¹, —R¹⁰NHSO₂R⁹, —R¹⁰NHCOR⁹ and —R¹⁰SO₂NHCOR⁹;

each R⁹ and R¹¹ are the same or different and are independently selected from the group consisting of H, alkyl, cycloalkyl, —R¹⁰cycloalkyl, —R¹⁰OH, —R₁₀(OR¹⁰)$_w$ where w is 1–10, and —R¹⁰NR¹⁰R¹⁰;

each R¹⁰ is the same or different and is independently selected from the group consisting of alkyl, cycloalkyl, alkenyl, cycloalkenyl and alkynyl;

n is 0, 1 or 2;
Ay is aryl;
Het is a 5- or 6-membered heterocyclic or heteroaryl group;
Y is N or CH;
R³ and R⁴ are the same or different and are each independently selected from the group consisting of H, halo, alkyl, cycloalkyl, alkenyl, Ay, Het, —OR⁷, —OAy, —C(O)R⁷, —C(O)Ay, —CO₂R⁷, —CO₂Ay, —SO₂NHR⁹, —NR⁷R⁸, —NR⁷Ay, —NHHet, —NHR¹⁰Het, —R¹⁰OR⁷, —R¹⁰OAy, —R¹⁰NR⁷R⁸ and R¹⁰NR⁷Ay;

q is 0, 1, 2, 3, 4 or 5;
each R⁵ is the same or different and is independently selected from the group consisting of halo, alkyl, cycloalkyl, alkenyl, cycloalkenyl, alkynyl, Ay, Het, —OR⁷, —OAy, —OHet, —C(O)R⁹, —CO₂R⁹, —C(O)NR⁷R⁸, —C(O)Ay, —C(O)NR⁷Ay, —C(O)Het, —C(O)NHR¹⁰Het, —C(S)NR⁹R¹¹, —C(NH)NR⁷R⁸, —C(NH)NR⁷Ay, —S(O)$_n$R⁹, —S(O)₂NR⁷R⁸, —S(O)₂NR⁷Ay, —S(O)₂NR⁷R⁸, —NR⁷Ay, —NHHet, —NHR¹⁰Ay, —NHR¹⁰Het, —R¹⁰cycloalkyl, —R¹⁰OR⁹, —R¹⁰NR⁷R⁸, —R¹⁰NR⁷Ay, —R¹⁰C(O)R⁹, —R¹⁰CO₂R⁹, —R¹⁰C(O)NR⁹R¹¹, —R¹⁰C(S)NR⁹R¹¹, —R¹⁰NHC(NH)NR⁹R¹¹, —R¹⁰C(NH)NR⁹R¹¹, —R¹⁰SO₂R⁹, —R¹⁰SO₂NHCOR⁹, —R¹⁰SO₂NR⁹R¹¹, cyano, nitro and azido; or two adjacent R⁵ groups together with the atoms to which they are bonded form a C$_{5-6}$ cycloalkyl or aryl;

p' is 0, 1 or 2; and
each R⁶ is the same or different and is independently selected from the group consisting of halo, alkyl, cycloalkyl, alkenyl, cycloalkenyl, alkynyl, Ay, Het, —OR⁷, —OAy, —OHet, —OR¹⁰Ay, —OR¹⁰Het, —C(O)R⁹, —CO₂R⁹, —C(O)NR⁷R⁹, —C(O)Ay, —C(O)NR⁷Ay, —C(O)NHR¹⁰Ay, —C(O)Het, —C(O)NHR¹⁰Het, —C(S)NR⁹R¹¹, —C(NH)NR⁷R⁸, —C(NH)NR⁷Ay, —S(O)$_n$R⁹, —S(O)$_n$Ay, —S(O)$_n$Het, —S(O)₂NR⁷R⁸, —S(O)₂NR⁷Ay, —NR⁷R⁸, —NR⁷Ay, —NHR¹⁰Ay, —NHHet, —NHR¹⁰Het, —R¹⁰cycloalkyl, —R¹⁰Ay, —R¹⁰Het, —R¹⁰OR⁹, —R¹⁰—O—C(O)R⁹, —R¹⁰—O—C(O)Ay, —R¹⁰—O—C(O)Het, —R¹⁰—O—S(O)$_n$R⁹, —R¹⁰NR⁷R⁸, —R¹⁰NR⁷Ay, —R¹⁰C(O)R⁹, —R¹⁰CO₂R⁹, —R¹⁰C(O)NR⁹R¹¹, —R¹⁰C(S)NR⁹R¹¹, —R¹⁰NHC(NH)NR⁹R¹¹, —R¹⁰C(NH)NR⁹R¹¹, —R¹⁰SO₂R⁹, —R¹⁰SO₂NHCOR⁹, —R¹⁰SO₂NR⁹R¹¹, cyano, nitro and azido; or two adjacent R⁶ groups together with the atoms to which they are bonded form a C$_{5-6}$cycloalkyl or a 5- or 6-membered heterocyclic group containing 1 or 2 heteroatoms; —NHR¹⁰Het; and R⁶ˣ is selected from the group consisting of —NR⁷R⁸ wherein —R⁷ and —R⁸ are not both H, —NR⁷Ay, —NHHet, —NHR¹⁰Ay and —NHR¹⁰Het;

X¹ is chloro, bromo or iodo; and
M² is —B(OH)₂, —B(ORa)₂, —B(Ra)₂, —Sn(Ra)₃, Zn-halide, ZnRa, or Mg-halide where Ra is alkyl or cycloalkyl and halide is halo.

Generally, the process for preparing compounds of formula (I) (all formulas and variables having been defined above in connection with Scheme 4-A), comprises the following steps:

(a) reacting a 2-chloro-5-trifluoromethylpyridine of formula (XI-A) with an acetophenone of formula (XXVII) to prepare a compound of formula (III-A);
(b) reacting the compound of formula (III-A) with a hydroxylamine source to prepare a compound of formula (IV-A);
(c) reacting the compound of formula (IV-A) with an acylating or sulfonylating agent to prepare a compound of formula (V-A);
(d) rearranging the compound of formula (V-A) to prepare a compound of formula (VI-A);
(e) halogenating a compound of formula (VI-A) to prepare a compound of formula (XXII-A);

(f) reacting a compound of formula (XXII-A) with a compound of formula (XXIV) to prepare a compound of formula (XXX);

(g) reacting the compound of formula (XXX) with sodium ethoxide to prepare a compound of formula (XXXI);

(h) reacting the compound of formula (XXXI) with an acid, followed by hydrolysis of the resulting ester to give a compound of formula (XXXII);

(i) reacting the compound of formula (XXXII) with diphenylphosphoryl azide in tert-butanol to give a compound of formula (I-X);

(j) optionally cleaving the compound of formula (I-X) to give a compound of formula (I-Y); and (k) optionally converting the compound of formula (I-Y) to a compound of formula (I-Z) using conditions selected from the group consisting of cross coupling, reductive amination, alkylation, acylation and sulfonylation.

More specifically, compounds of formula (I) can be prepared by converting the compounds of formula (XXX) to compounds of formula (I) using the methods described above in connection with the process of Scheme 1-A.

Compounds of formula (XXX) can be prepared using methods analogous to those described above for the preparation of compounds of formula (XVII) according to Scheme 4, with the exception that the first step (i.e., the preparation of compounds of formula (III-A)) involves the condensation of 2-chloro-5-trifluoromethylpyridine with the acetophenone of formula (XXVII) under basic conditions, in place of the reaction of the picoline of formula (XI) with the benzoylating agent of formula (II) as is employed in the synthesis of compounds of formula (VI) as described in Scheme 1. As will be apparent to those skilled in the art, a particular compound of formula (I) may be converted to other compounds of formula (I) using techniques well known in the art. The foregoing synthesis of Schemes 1-A, 2-A, 3-A and 4A demonstrate certain methods for converting a compound of formula (I) to another compound of formula (I). Another method of converting a compound of formula (I) to another compound of formula (I) comprises a) oxidizing the compound of formula (I-A) to prepare a compound of formula (I-B) and then b) optionally reacting a compound of formula (I-B) with an oxygen or amine nucleophile of formula $R^2$, wherein $R^2$ is selected from the group consisting of —$NR^7R^8$, —$OR^7$, —OAy, Het bonded through N, —NHHet, $NHR^{10}$Het, OHet and —$OR^{10}$Het to produce a compound of formula I wherein $R^2$ is selected from the group consisting of —$NR^7R^8$, —$OR^7$, —OAy, Het bonded through N, —NHHet, $NHR^{10}$Het, OHet and —$OR^{10}$Het.

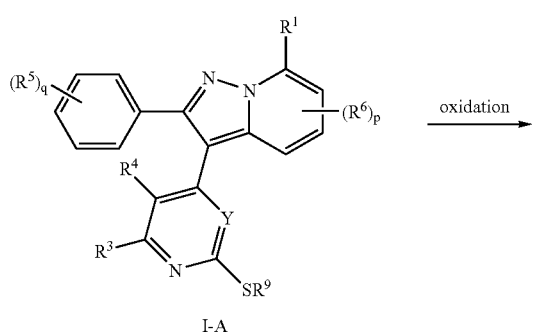

I-A

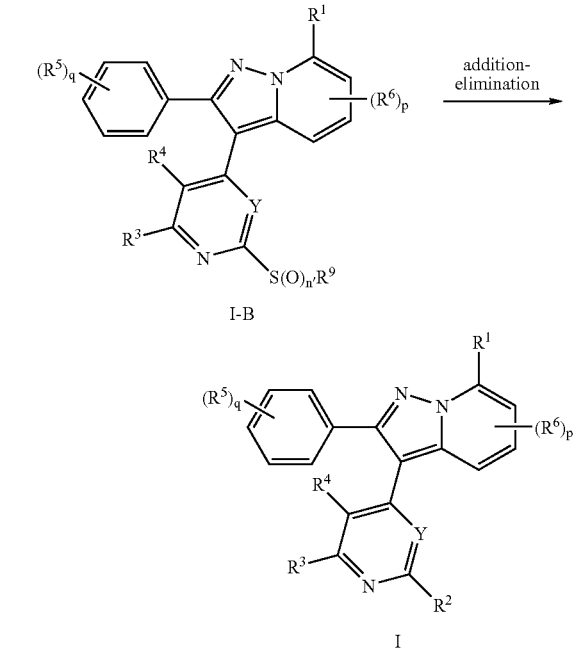

wherein $R^2$ is selected from the group consisting of —$NR^7R^8$, —$OR^7$, —OAy, Het bonded through N, —NHHet, $NHR^{10}$Het, OHet and —$OR^{10}$Het; p is 1, 2 or 3; n' is 1 or 2 and all other variables are as defined in connection with any of the processes described above.

More specifically, compounds of formula (I) can be prepared by reacting a compound of formula (I-B) (i.e., compounds of formula I wherein $R^2$ is $S(O)_{n'}R^9$ where n' is 1 or 2) with an oxygen or amine nucleophile of formula $R^2$, wherein $R^2$ is selected from the group consisting of —$NR^7R^8$, —$OR^7$, —OAy, Het bonded through N, —NHHet, $NHR^{10}$Het, OHet and —$OR^{10}$Het. The reaction may be carried out neat or in a suitable solvent and may be heated to 50–150° C. Typically the solvent is a lower alcohol such as methanol, ethanol, isopropanol and the like or solvent such as N,N-dimethylformamide or tetrahydrofuran, and the like. Optionally a base may be used to facilitate the reaction. Typically the base can be potassium carbonate, or an amine base such as triethylamine.

Compounds of formula (I-B) may be conveniently prepared by reacting a compound of formula (I-A) (i.e., compounds of formula (I) wherein $R^2$ is —$S(O)_nR^9$ where n is 0) with an oxidizing agent in an inert solvent, optionally in the presence of a base.

Typically the oxidizing agent is a peracid such as m-chloroperbenzoic acid or the like optionally with a base such as sodium bicarbonate. Careful monitoring of the stoichiometry between the oxidizing agent and the substrate allows the product distribution between sulfoxide (n=1), and sulfone (n=2) to be controlled. Suitable solvents include but are not limited to, dichloromethane, chloroform and the like.

Compounds of formula (I-A) are prepared by methods described above wherein $R^2$ is —$SR^9$ from the reaction of compounds selected from the group consisting of compounds of formula (XVI), compounds of formula (IX) and compounds of formula (XX) with a compound of formula (X-A) (i.e., the compound of formula (X) wherein $R^2$ is —$SR^9$). The requisite compound of formula (X-A) can be obtained from commercial sources or prepared by methods known to one skilled in the art.

Another particularly useful method for converting a compound of formula (I) to another compound of formula (I) comprises reacting a compound of formula (I-C) (i.e., a compound of formula (I) wherein $R^2$ is fluoro) with an amine (including substituted amines, heterocycles and heteroaryls, particularly those linked through N), and optionally heating the mixture to 50–150° C. to prepare a compound of formula (I-D) (i.e., a compound of formula (I) wherein $R^2$ is selected from the group consisting of —$NR^7R^8$, Het, —NHHet and —$NHR^{10}$Het).

foregoing conversions are represented schematically as follows:

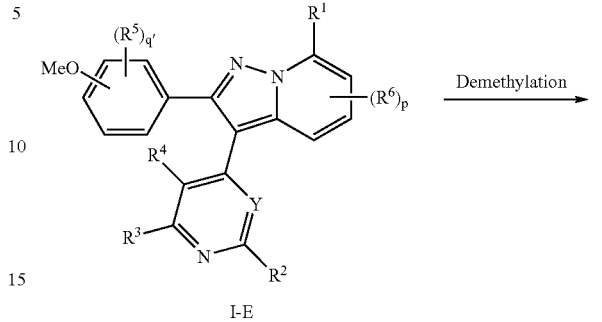

I-E

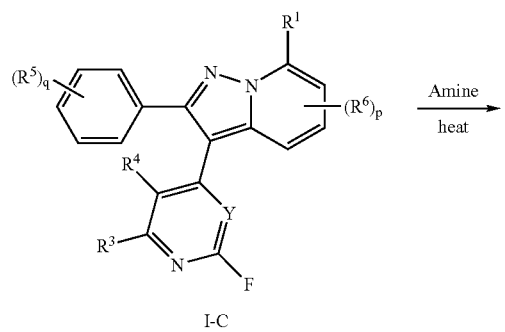

I-C

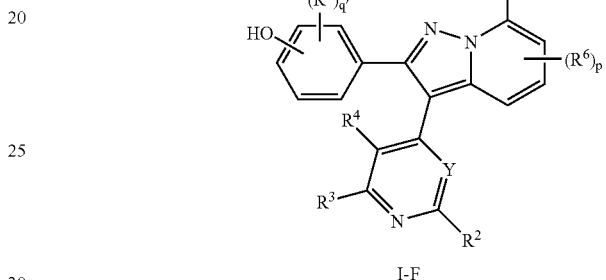

I-F

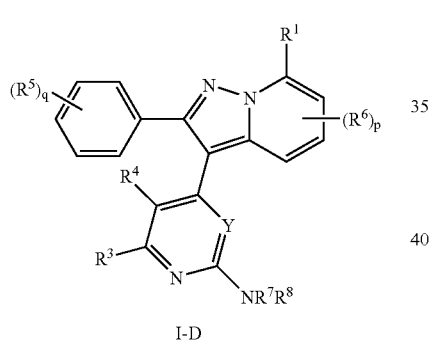

I-D

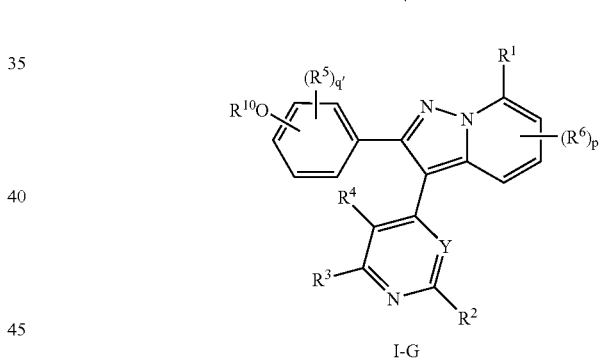

I-G wherein all other variables are as defined in connection with any of the processes described above.

This procedure may be carried out by mixing a compound of formula (I-C) in an amine neat, or in a suitable solvent with an excess of amine to produce a compound of formula (I-D). Typically the solvent is a lower alcohol such as methanol, ethanol, isopropanol and the like. Other suitable solvents may include N,N-dimethylformamide, 1-methyl-2-pyrrolidine and the like.

As a further example, a compound of formula (I-E) (i.e., a compound of formula (I) wherein q is 1 or more and at least one $R^5$ is O-methyl) may be converted to a compound of formula (I-F) (i.e., a compound of formula (I) wherein q is 1 or more and at least one $R^5$ is OH) using conventional demethylation techniques. Additionally, a compound of formula (I-F) may optionally be converted to a compound of formula (I-G) (i.e., a compound of formula (I) wherein q is 1 or more and at least one $R^5$ is $OR^{10}$). For example, the wherein q' is 0, 1, 2, 3 or 4; Me is methyl, and all other variables are as defined in connection with any of the processes described above.

The demethylation reaction may be carried out by treating a compound of formula (I-E) in a suitable solvent with a Lewis acid at a temperature of −78° C. to room temperature, to produce a compound of formula (I-F). Typically the solvent is an inert solvent such as dichloromethane, chloroform, acetonitrile, toluene and the like. The Lewis acid may be boron tribromide, trimethylsilyl iodide or the like.

Optionally, a compound of formula (I-F) may be further converted to a compound of formula (I-G) by an alkylation reaction. The alkylation reaction may be carried out by treating a compound of formula (I-F) in suitable solvent with an alkyl halide of formula $R^{10}$-Halo where $R^{10}$ is as defined above, to form a compound of formula (I-G). The reaction is preferably carried out in the presence of a base and with optionally heating to 50–200° C. The reaction may be carried out in solvents such as N,N-dimethylformamide, dimethylsulfoxide and the like. Typically the base is potassium carbonate, cesium carbonate, sodium hydride or the like. Additionally, as will be apparent to one skilled in the art, the alkylation reaction can be carried out under Mitsunobu conditions.

As a further example of methods for converting a compound of formula (I) to another compound of formula (I), a compound of formula (I-H) (i.e., a compound of formula (I) wherein q is 1 or more and at least one $R^5$ is halo) may be converted to a compound of formula (I-J) (i.e., a compound of formula (I) wherein q is 1 or more and at least one $R^5$ is Het) or a compound of formula (I-K) (i.e., a compound of formula (I) wherein q is 1 or more and at least one $R^5$ is Ay). For example, the conversion of a compound of formula (I-H) to a compound of formula (I-J) or a compound of formula (I-K) is shown schematically below.

Het-$M^4$ or Ay-$M^4$ (depending upon whether a compound of formula (I-J) or a compound of formula (I-K) are desired). The reaction may also be performed in the presence of an excess Het-$M^4$ or Ay-$M^4$. The palladium (0) catalyst is preferably present in 1–25 mol % compared to the compound of formula (I-H). Examples of suitable palladium catalysts include but are not limited to, tetrakis(triphenylphosphine)palladium (0), dichlorobis(triphenyl-phosphine)palladium(II), and bis(diphenylphosphinoferrocene) palladium (II) dichloride. Suitable solvents include but are not limited to, N,N-dimethylformamide, toluene, tetrahydrofuran, dioxane, and 1-methyl-2-pyrrolidinone. When the compound of formula Het-$M^4$ or Ay-$M^4$ is a boronic acid or ester or a borinate the reaction is more conveniently carried out by adding a base in a proportion equivalent to, or greater than, that of the compound of formula Het-$M^4$ or Ay-$M^4$.

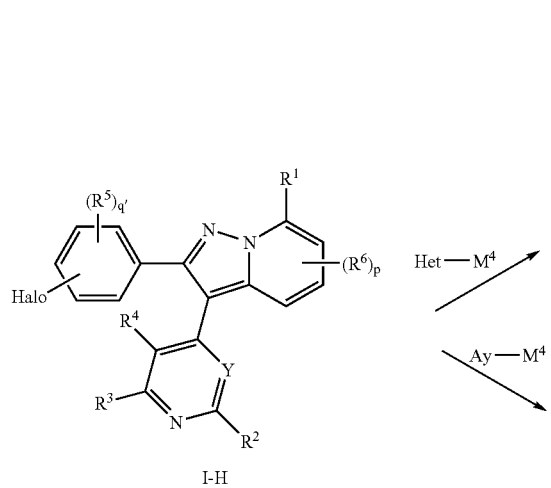

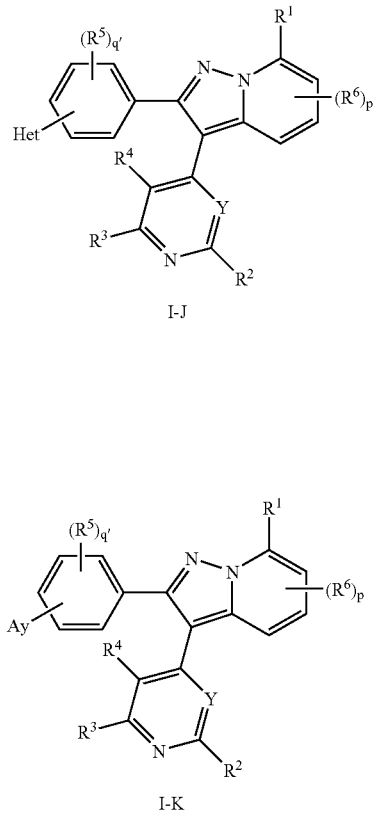

wherein q' is 0 1, 2, 3 or 4; $M^4$ is selected from the group consisting of —B(OH)$_2$, —B(ORa)$_2$, —B(Ra)$_2$, and —Sn (Ra)$_2$ wherein Ra is alkyl or cycloalkyl; and all other variables are as defined in connection with any of the processes described above.

The conversion of a compound of formula (I-H) to a compound of formula (I-J) or (I-K) is carried out by coupling the compound of formula (I-H) with a compound of formula Het-$M^4$ to make a compound of formula (I-J) or a compound of formula Ay-$M^4$ to make a compound of formula (I-K). The reaction may be carried out in an inert solvent, in the presence of a palladium (0) source. The reaction may optionally be heated to 50–150° C. Preferably the reaction is performed by reacting equimolar amounts of a compound of formula (I-H) with a compound of formula Compounds of formula Het-$M^4$ and Ay-$M^4$ may be obtained from commercial sources or prepared either as discreet isolated compounds or generated in situ using methods known to one skilled in the art. (Suzuki, A. *J. Organomet Chem.* 1999, 576, 147; Stille, J. *Angew. Chem. Int. Ed. Engl.* 1986, 25, 508; Snieckus, V. *J. Org. Chem.* 1995, 60, 292.)

In yet another example, a compound of formula (I-H) (i.e., a compound of formula (I) wherein q is 1 or more and at least one $R^5$ is halo) is converted to a compound of formula (I-L) (i.e., a compound of formula (I) wherein q is 1 or more and at least one $R^5$ is NH$_2$). Optionally, a compound of formula (I-L) may then be converted to a compound of formula (I-M) (i.e., a compound of formula (I)

wherein q is 1 or more and at least one $R^5$ is —$NR^7R^8$). For example, the foregoing conversions are represented schematically as follows:

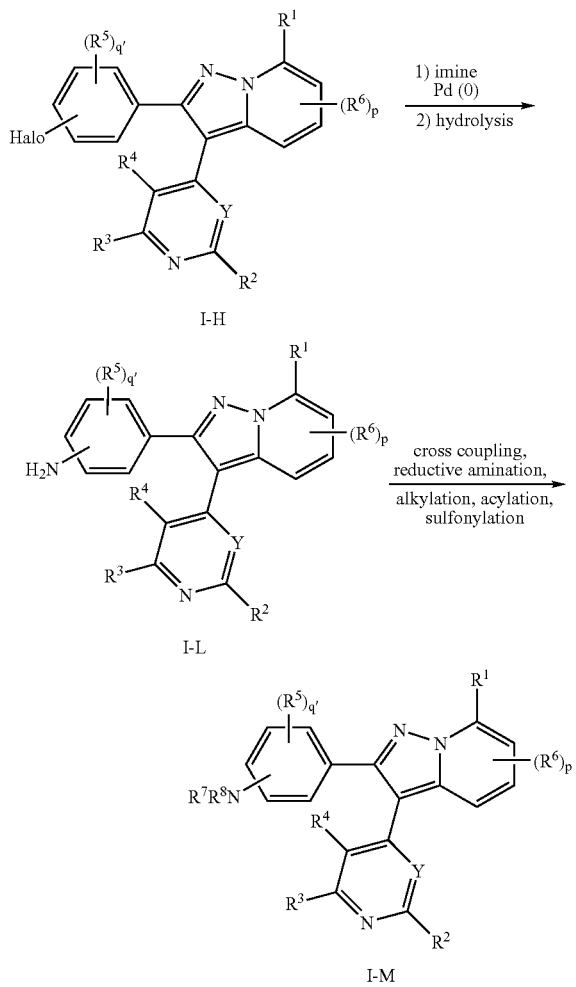

wherein q' is 0, 1, 2, 3 or 4, and all other variables are as defined in connection with any of the processes described above, with the proviso that in compounds of formula (I-M) both $R^7$ and $R^8$ of the amine attached to the 2-phenyl are not H.

The process of converting a compound of formula (1-H) to a compound of formula (I-L) is carried out by reacting a compound of formula (I-H) with an imine in the presence of a palladium (0) source, a base and a suitable ligand, followed by hydrolysis to give a compound of formula (I-L). See J. Wolfe, et al., *Tetrahedron Letters* 38:6367–6370 (1997). Typically the imine is benzophenoneimine, the palladium (0) source is tris(dibenzylideneacetone)dipalladium(0), the base is sodium tert-butoxide and the ligand is racemic-2,2'-bis(diphenylphosphino)-1,1'-binaphthyl. Suitable solvents include N,N-dimethylformamide and the like.

Reaction of a compound of formula (I-L) with a compound of formula $R^7$-halogen in a suitable solvent in the presence of base, optionally with heating may be used to prepare a compound of formula (I-M). Typically the base is triethylamine or pyridine and the solvent N,N-dimethylformamide and the like. Transformations well known to those skilled in the art for use with anilines can be used to convert the compounds of formula (I-L) to compounds of formula (I-M).

Additional compounds of formula (I-M) can be obtained by reductive amination of compounds of formula (I-L) with ketones or aldehydes. See, A. Abdel-Magid, et al., *J. Org. Chem.* 61:3849–3862 (1996). Typically a compound of formula (I-L) is treated with an aldehyde or a ketone in the presence of an acid, such as acetic acid, and a reducing agent, such as sodium triacetoxyborohydride and the like, in an inert solvent such as dichloroethane and the like.

Based on this disclosure and the examples contained herein one skilled in the art can readily convert compounds of formula (I) or a pharmaceutically acceptable salt, solvate or physiologically functional derivative thereof into other compounds of formula (I), or a pharmacetuically acceptable salt, solvate or physiologically functional derivative thereof.

The present invention also provides radiolabeled compounds of formula (I) and biotinylated compounds of formula (I). Radiolabeled compounds of formula (I) and biotinylated compounds of formula (I) can be prepared using conventional techniques. For example, radiolabeled compounds of formula (I) can be prepared by reacting the compound of formula (I) with tritium gas in the presence of an appropriate catalyst to produce radiolabeled compounds of formula (I).

In one preferred embodiment, the compounds of formula (I) are tritiated.

The radiolabeled compounds of formula (I) and biotinylated compounds of formula (I) are useful in assays for the identification of compounds for the treatment or prophylaxis of viral infections such as herpes viral infections. Accordingly, the present invention provides an assay method for identifying compounds which have activity for the treatment or prophylaxis of viral infections such as herpes viral infections, which method comprises the step of specifically binding the radiolabeled compound of formula (I) or the biotinylated compound of formula (I) to the target protein. More specifically, suitable assay methods will include competition binding assays. The radiolabeled compounds of formula (I) and biotinylated compounds of formula (I) can be employed in assays according to the methods conventional in the art.

The following examples are intended for illustration only and are not intended to limit the scope of the invention in any way. Reagents are commercially available or are prepared according to procedures in the literature. Example numbers refer to those compounds listed in the tables above. $^1$H and $^{13}$C NMR spectra were obtained on Varian Unity Plus NMR spectrophotometers at 300 or 400 MHz, and 75 or 100 MHz respectively. $^{19}$F NMR were recorded at 282 MHz. Mass spectra were obtained on Micromass Platform, or ZMD mass spectrometers from Micromass Ltd. Altrincham, UK, using either Atmospheric Chemical Ionization (APCI) or Electrospray Ionization (ESI). Analytical thin layer chromatography was used to verify the purity of some intermediates which could not be isolated or which were too unstable for full characterization, and to follow the progress of reactions. Unless otherwise stated, this was done using silica gel (Merck Silica Gel 60 F254). Unless otherwise stated, column chromatography for the purification of some compounds, used Merck Silica gel 60 (230–400 mesh), and the stated solvent system under pressure. All compounds were characterized as their free-base form unless otherwise stated. On occasion the corresponding hydrochloride salts were formed to generate solids where noted.

EXAMPLE 1

4-[5-Chloro-2-(4-fluorophenyl)pyrazolo[1,5-α]pyridin-3-yl]-N-cyclopentyl-2-pyrimidinamine

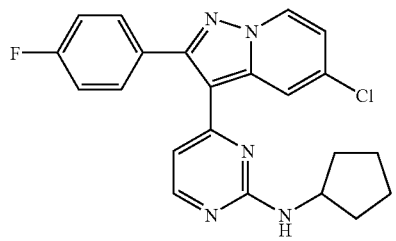

a) 2-(4-Chloro-2-pyridinyl)-1-(4-fluorophenyl)ethanone

To a cold (0 20 C.) solution of 4-chloro-2-picoline (5.0 g, 39 mmol) and ethyl 4-fluorobenzoate (6.6 g, 39 mmol) in tetrahydrofuran (100 mL) was added lithium bis(trimethylsilyl)amide (80 mL, 1.0 M in tetrahydrofuran, 80 mmol) dropwise via a pressure equalizing funnel over 30 minutes. Upon complete addition, the cold bath was removed and the resulting solution was stirred at room temperature for 15 hours. The reaction mixture was concentrated under reduced pressure and methanol was added to the reaction, resulting in the formation of a white precipitate. The precipitate was collected by filtration and dried to give 2-(4-chloro-2-pyridinyl)-1-(4-fluorophenyl)ethanone (9.6 g, 99%) as a white solid. $^1$H-NMR (DMSO-$d_6$): δ 7.90 (m, 3H), 7.11 (t, 2H), 6.56 (s, 1H), 5.67 (s, 1H), 4.14 (m, 2H); $^{19}$F-NMR (DMSO-$d_6$): δ -115.67; MS m/z 250 (M+1).

b) 2-(4-Chloro-2-pyridinyl)-1-(4-fluorophenyl)ethanone oxime

To a solution of 2-(4-chloro-2-pyridinyl)-1-(4-fluorophenyl)ethanone (9.6 g, 38 mmol) in methanol (200 mL) was added hydroxylamine hydrochloride (13.5 g, 190 mmol) followed by the addition of a sodium hydroxide solution (7.8 g, 190 mmol in 50 mL of water). The resulting suspension was heated at reflux for 2 hours and then allowed to cool to room temperature. The mixture was concentrated and water was added to the resulting slurry. A white precipitate formed, which was collected by filtration, washed with water and dried (magnesium sulfate) to give 2-(4-chloro-2-pyridinyl)-1-(4-fluorophenyl)ethanone oxime (8.45 g, 84%) as a white solid. $^1$H-NMR (DMSO-$d_6$): δ 11.56 (s, 1H), 8.44 (d, 1H), 7.80 (m, 2H), 7.40 (m, 2H), 7.22 (m, 2H), 4.29 (s, 2H); $^{19}$F-NMR (DMSO-$d_6$): δ -113.44; MS m/265 (M+1).

c) 5-Chloro-2-(4-fluorophenyl)pyrazolo[1,5-α]pyridine

To a solution of 2-(4-chloro-2-pyridinyl)-1-(4-fluorophenyl)ethanone oxime (8.0 g, 30 mmol) in 1,2-dimethoxyethane (50 mL) at 0° C. was added trifluoroacetic anhydride (6.3 g, 30 mmol), keeping the temperature below 10° C. during the addition. After the addition was complete, the reaction was warmed to room temperature. The solution was then cooled to 4° C. and a solution of triethylamine (8.4 mL, 60 mmol) in 1,2-dimethoxyethane (20 mL) was added over a period of 0.5 hours. The mixture was allowed to warm to room temperature and was stirred for 1.5 hours. To this mixture was added iron(II) chloride (40 mg) and the reaction was heated at 75° C. for 15 hours.

The reaction mixture was poured into water (300 mL). The resulting suspension was extracted with ethyl acetate. The combined organics were dried (magnesium sulfate), filtered and concentrated to a solid residue. This residue was purified by flash chromatography (1:1 ethyl acetate-hexane) to give 5-chloro-2-(4-fluorophenyl)pyrazolo[1,5-α]pyridine (4.2 g, 57%) as a white solid. $^1$H-NMR (CDCl$_3$): δ 8.36 (d, 1H), 7.93 (q, 2H), 7.49 (d, 1H), 7.15 (t, 2H), 6.70 (dd, 1H), 6.69 (s, 1H); $^{19}$F-NMR (CDCl$_3$): δ -113.30; MS m/z 247 (M+1).

d) 5-Chloro-2-(4-fluorophenyl)pyrazolo[1,5-α]pyridine-3-carbaldehyde

Phosphorous oxychloride (0.6 mL, 6.4 mmol) was added to N,N-dimethylformamide (10 mL) and the resulting mixture stirred at room temperature for 10 minutes. 5-Chloro-2-(4-fluorophenyl)pyrazolo[1,5-α]pyridine (1.0 g, 4.1 mmol) was added and the reaction mixture was stirred at room temperature for 12 hours. The reaction mixture was poured into ice-water and neutralized to pH 7 with aquous ammonium hydroxide. The resulting slurry was extracted with dichloromethane (3×40 mL). The combined organics were washed with brine, dried (magnesium sulfate), filtered and concentrated to give, after recrystallization from acetonitrile, 5-chloro-2-(4-fluorophenyl)pyrazolo [1,5-α]pyridine-3-carbaldehyde (0.95 g, 85%) as a white solid. $^1$H-NMR (CDCl$_3$): δ10.07 (s, 1H), 8.49 (d, 1H), 8.44 (d, 1H), 7.78 (q, 2H), 7.22 (t, 2H), 7.07 (dd, 1H); MS m/z 275 (M+1).

e) 1-[5-Chloro-2-(4-fluorophenyl)pyrazolo[1,5-α] pyridin-3-yl]-2-butyn-1-one To a solution of 5-chloro-2-(4-fluorophenyl)pyrazolo[1,5-α]pyridine-3-carbaldehyde (0.93 g, 3.4 mmol) in tetrahydrofuran (20 mL) at -78° C. was added ethynylmagnesium bromide (16 mL, 0.5 M in tetrahydrofuran, 8.0 mmol). The mixture was allowed to warm to room temperature and stirred for 1 hour. Water was added to the reaction and the resulting mixture was extracted with ethyl acetate. The ethyl acetate phase was dried (magnesium sulfate), filtered and concentrated to a solid residue. This residue was dissolved in dichloromethane (50 mL) and manganese dioxide (5 g) was added. This slurry was stirred at room temperature for 2 hours. The manganese dioxide was removed by filtration and the filtrate was concentrated to a solid. This solid was purified by flash chromatography (dichloromethane) to give 1-[5-chloro-2-(4-fluorophenyl)pyrazolo[1,5-α]pyridin-3-yl]-2-butyn-1-one (0.63 g, 62% for two steps) as a white solid. $^1$H-NMR (CDCl$_3$): δ 8.52 (d, 1H), 8.47 (d, 1H), 7.69 (q, 2H), 7.18 (t, 2H), 7.07 (dd, 1H), 3.00 (s, 1H); $^{19}$F-NMR (CDCl$_3$): δ -111.69; MS m/z 299 (M+1).

f) 4-[5-Chloro-2-(4-fluorophenyl)pyrazolo[1,5-α]pyridin-3-yl]-N-cyclopentyl-2-pyrimidinamine To a solution of 1-[5-chloro-2-(4-fluorophenyl)pyrazolo[1,5-α]pyridin-3-yl]-2-butyn-1-one (0.61 g. 2.0 mmol) in N,N-dimethylformamide was added cyclopentyl guanidine hydrochloride (0.67 g, 4.1 mmol) followed by anhydrous potassium carbonate (0.57 g, 4.1 mmol). The resulting mixture was heated at 80° C. for 12 hours. Upon cooling to room temperature, water was added. The mixture was extracted with ethyl acetate. The ethyl acetate phase was washed with brine, dried (magnesium sulfate), filtered and concentrated in vacuo. The resulting residue was purified by flash chromatography (1:1 ethyl acetate-hexane) to give, after recrystallization from acetonitrile, 4-[5-chloro-2-(4-fluorophenyl)pyrazolo[1,5-α]pyridin-3-yl]-N-cyclopentyl-2-pyrimidinamine (0.6 g, 74%) as a white solid. $^1$H-NMR (CDCl$_3$): δ8.54 (broad s, 1H), 8.40 (d, 1H), 8.04 (d, 1H), 7.60 (q, 2H), 7.16 (t, 2H), 6.88 (dd, 1H), 6.28 (d, 1H), 5.22 (d, 1H), 4.40 (m, 1H), 1.4–2.2 (m, 8H); $^{19}$F-NMR (CDCl$_3$): δ −112.5; MS m/z 408 (M+1).

EXAMPLE 2

N-Cyclopentyl-3-[2-(cyclopentylamino)-4-pyrimidinyl]-2-(4-fluorophenyl)pyrazolo[1,5-α]pyridin-5-amine

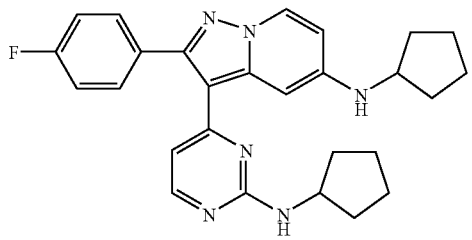

To a solution of 4-[5-chloro-2-(4-fluorophenyl)pyrazolo[1,5-α]pyridin-3-yl]-N-cyclopentyl-2-pyrimidinamine (0.1 g, 0.25 mmol) in cyclopentylamine (5 mL) was added racemic-2,2'-bis(diphenylphosphino)-1,1'-binaphthyl (46 mg, 0.08 mmol), cesium carbonate (120 mg, 0.38 mmol) and palladium (II) acetate (11 mg, 0.05 mmol).

The resulting mixture was stirred at 80° C. for 24 hours, at which time the reaction was judged complete by thin layer chromatography. The solution was cooled to room temperature and ethyl acetate and water were added to the reaction mixture. The phases were separated, and the aquous phase again extracted with ethyl acetate. The combined organics were dried (magnesium sulfate), filtered and concentrated. The resulting residue was purified by flash chromatography (1:1 hexanes-ethyl acetate) to give N-cyclopentyl-3-[2-(cyclopentylamino)-4-pyrimidinyl]2-(4-fluorophenyl)pyrazolo[1,5-α]pyridin-5-amine (78 mg, 70%) as a white solid. $^1$H-NMR (CDCl$_3$): δ 8.16 (d, 1H), 7.95 (d, 1H), 7.58 (q, 2H), 7.38 (d, 1H), 7.12 (t, 2H), 6.24 (dd, 1H), 6.20 (d, 1H), 5.05 (d, 1H), 4.40 (m, 1H), 4.13 (m, 1H), 3.89 (m, 1H), 1.5–2.2 (m, 16H); $^{19}$F-NMR (CDCl$_3$): δ −113.7; MS m/z 457 (M+1).

EXAMPLE 3

3-[2-(Cyclopentylamino)-4-pyrimidinyl]2-(4-fluorophenyl)pyrazolo[1,5-α]pyridin-5-amine

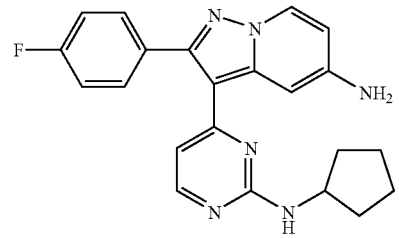

To a solution of 4-[5-chloro-2-(4-fluorophenyl)pyrazolo[1,5-α]pyridin-3-yl]-N-cyclopentyl-2-pyrimidinamine (0.1 g, 0.25 mmol) in toluene (5 mL) was added benzophenone imine (0.13 g, 0.75 mmol), tris(dibenzylideneacetone)dipalladium (0.02 g, 0.03 mmol), racemic-2,2'-bis(diphenylphosphino)-1,1'-binaphthyl (0.05 g, 0.09 mmol) and sodium tert-butoxide (0.07 g, 0.75 mmol). The reaction was heated at 100° C. for 3 hours, then allowed to cool to room temperature. Aqueous sodium bicarbonate and ethyl acetate were added to the reaction mixture. The phases were separated and the organic phase was washed with brine and dried (magnesium sulfate). Filtration and concentration, followed by purification by flash chromatography (1:4 ethyl acetate-hexanes to 1:1 ethyl acetate-hexanes) gave 3-[2-(cyclopentylamino)-4-pyrimidinyl]-N-(diphenylmethylene)-2-(4-fluorophenyl)pyrazolo[1,5-α]pyridin-5-amine as a solid. This solid was dissolved in tetrahydrofuran (10 mL). To this solution at 0° C. was added 4N hydrochloric acid (2 mL) dropwise. Subsequently, the reaction mixture was stirred for 30 minutes. The reaction mixture was diluted with ethyl acetate, then saturated aquous bicarbonate was added slowly until the ethyl acetate layer turned clear. The resulting mixture was stirred for 30 minutes. The organic phase was washed with water, brine and dried (magnesium sulfate). Filtration and concentration, followed by flash chromatography (ethyl acetate) gave 3-[2-(cyclopentylamino)-4-pyrimidinyl]-2-(4-fluorophenyl)pyrazolo[1,5-α]pyridin-5-amine (54 mg, 57%) as a yellow foam. $^1$H-NMR (CDCl$_3$): δ 8.22 (d, 1H), 7.97 (d, 1H), 7.58 (q, 2H), 7.11 (t, 2H), 6.34 (dd, 1H), 6.20 (d, 1H), 5.14 (d, 1H), 4.31 (m, 1H), 4.10 (m, 3H), 1.5–2.2 (m, 8H); $^{19}$F-NMR (CDCl$_3$): δ −113.4; MS m/z 389 (M+1).

EXAMPLE 4

N-[3-[2-(Cyclopentylamino)-4-pyrimidinyl]-2-(4-fluorophenyl)pyrazolo[1,5-α]pyridin-5-yl]methanesulfonamide

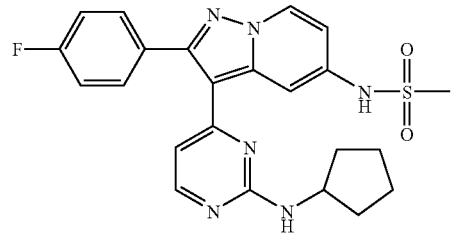

To a solution of 3-[2-(cyclopentylamino)-4-pyrimidinyl]-2-(4-fluorophenyl)pyrazolo[1,5-α]pyridin-5-amine (60 mg, 0.15 mmol) in anhydrous pyridine (5 mL) was added methylsulfonyl chloride (36 mg, 0.3 mmol). The reaction was stirred at room temperature overnight. The reaction mixture was diluted with ethyl acetate, then saturated aquous bicarbonate was added. The phases were separated, the organic phase was washed with water, brine and dried (magnesium sulfate). Filtration and concentration, followed by flash chromatography (1:1 ethyl acetate-hexane) gave N-[3-[2-(cyclopentylamino)-4-pyrimidinyl]-2-(4-fluorophenyl)pyrazolo[1,5-α]pyridin-5-yl]methanesulfonamide (35 mg, 50%) as a solid. $^1$H-NMR (CDCl$_3$): δ 8.42 (d, 1H), 8.15 (d, 1H), 8.05 (d, 1H), 7.60 (q, 2H), 7.13 (t, 2H), 6.90 (dd, 1H), 6.30 (d, 1H), 5.34 (d, 1H), 4.30 (m, 1H), 3.12 (s, 3H), 1.5–2.2 (m, 8H); $^{19}$F-NMR (CDCl$_3$): δ −112.64; MS m/z 467 (M+1).

EXAMPLE 5

3-[2-(cyclopentylamino)-4-pyrimidinyl]-2-(4-fluorophenyl)pyrazolo[1,5-α]pyridin-6-amine

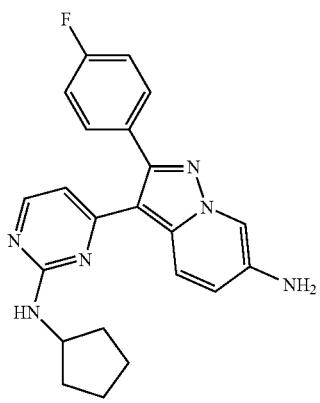

a) 1-(4-Fluorophenyl)-2-(2-(5-trifluoromethyl)pyridyl)ethanone

To a solution of 4-fluoroacetophenone (13.8 g, 0.100 mol) and 2-chloro-5-trifluoromethylpyridine (20.0 g, 0.110 mol) in tetrahydrofuran (400 mL) was added sodium hydride (950%, 5.56 g, 0.220 mol) in several portions. The reaction was stirred at room temperature for 72 hours then carefully quenched by the addition of water (300 mL) and diethyl ether (200 mL). The organic layer was separated and extracted with 6N HCl (2×300 mL). The aqueous extracts were cooled to 0° C. and 6N NaOH was used to adjust the solution to pH12. The mixture was then extracted with diethyl ether and the combined organic extracts were dried over magnesium sulfate. The drying agent was removed by filtration and the filtrate was evaporated to dryness to afford the title compound as a tautomeric mixture, 20.9 g (73%). $^1$H NMR (CDCl$_3$): δ 8.87(s), 8.63(s), 8.14(dd, J=5.1, 8.4 Hz), 8.00–7.83(m), 7.51(d, J=8.4 Hz), 7.22–7.12(m), 6.13(s), 4.60(s). MS (ES): 284 (M+1).

b) 1-(4-Fluorophenyl)-2-(2-(5-trifluoromethyl)pyridyl)ethanone oxime

To a solution of 1-(4-fluorophenyl)-2-(2-(5-trifluoromethyl)pyridyl)ethanone (80.0 g, 0.282 mol) in methanol (1 L) at room temperature was added 10% aqueous sodium hydroxide (436 mL, 1.09 mol). The resulting solution was stirred vigorously as solid hydroxylamine hydrochloride (98.0 g, 1.40 mol) was added. The mixture was heated to reflux for 2 hours, treated with decolorizing charcoal while hot, then filtered through Celite while hot The filtrate was concentrated to one-half its original volume and then cooled to 0° C. with stirring for one hour. The resulting solids were collected by filtration, washed with water, and dried under vacuum at 50° C. overnight to provide the title compound as a light yellow powder, 73.9 g (88%). $^1$H NMR (DMSO-d$_6$): δ 11.60(s, 1H), 8.86(s, 1H), 8.14(dd, 1H, J=2.1, 8.1 Hz), 7.78(dd, 2H, J=5.7, 9.0 Hz), 7.53(d, 1H, J=8.4 Hz), 7.23(t, 2H, J=9.0 Hz), 4.40(s, 2H). MS (ES): 299 (M+1).

c) 3-(4-Fluorophenyl)-2-(2-(5-trifluoromethyl)pyridyl)-2H-azirine

To a solution of 1-(4-fluorophenyl)-2-(2-(5-trifluoromethyl)pyridyl)ethanone oxime (25.0 g, 0.084 mol) in methylene chloride (400 mL) was added triethylamine (46.7 mL, 0.335 mol). The solution was cooled to 0° C. under a nitrogen atmosphere, and trifluoroacetic anhydride (14.1 mL, 0.100 mol) was added dropwise. The reaction was stirred for 0.5 hours then quenched with water. The organic layer was separated and dried over anhydrous magnesium sulfate. The drying agent was removed by filtration and the solvent was evaporated from the filtrate to leave an oil. The residue was loaded onto a silica gel column and eluted with 15% ethyl acetate in hexanes to give the title compound as an oil which solidified on standing, 19.4 g (82%). $^1$H NMR (CDCl$_3$): δ 8.76(s, 1H), 7.93(dd, 2H, J=5.4, 8.7 Hz), 7.83 (dd, 1H, J=2.1, 8.4 Hz), 7.27(t, 2H, J=8.7 Hz), 7.21 (d, 1H, J=8.1 Hz), 3.54 (s, 1H). MS (ES): 281 (M+1).

d) 2-(4-Fluorophenyl)-6-(trifluoromethyl)pyrazolo[1,5-α]pyridine 3-(4-Fluorophenyl)-2-(2-(5-trifluoromethyl)pyridyl)-2H-azirine (40.0 g, 0.143 mol) was dissolved in 1,2,4-trichlorobenzene (400 mL) and the mixture was heated to 200° C. for 10 hours. The reaction mixture was then cooled to room temperature and poured onto a silica gel column. The column was eluted with hexanes to remove the 1,2,4-trichlorobenzene, and then with 20% diethyl ether in hexanes to elute the product. The desired fractions were combined and the solvent was evaporated under reduced pressure to leave the title compound, 28.7 g (710%). $^1$H NMR (CDCl$_3$): δ 8.84(s, 1H), 7.98(dd, 2H, J=5.4, 8.7 Hz), 7.65(d, 1H, J=9.3 Hz), 7.28(d, 1H, J=9.3Hz), 7.20(t, 2H, J=8.7 Hz), 6.88(s, 1H). MS (ES): 281 (M+1).

e) 2-(4-Fluorophenyl)-6-(trifluoromethyl)pyrazolo[1,5-α]pyridine-3-carbaldehyde

To a cold (0° C.) solution of phosphorus oxychloride (8.0 mL 86 mmol) in N,N-dimethylformamide (160 mL) was added 2-(4-fluorophenyl)-6-(trifluoromethyl)pyrazolo[1,5-α]pyridine (11.0 g, 39.3 mmol). The reaction mixture was stirred at room temperature for 72 hours, then quenched with ice water. The solid precipitate was collected on a filter to provide 2-(4-fluorophenyl)-6-(trifluoromethyl)pyrazolo[1, 5-α]pyridine-3-carbaldehyde (11.4 g, 94%) as a white solid. $R_f$ 0.45 (4:1 hexanes:ethyl acetate); $^1H$ NMR (400 MHz, CDCl$_3$): δ 10.15 (s, 1H), 8.92 (s, 1H), 8.53 (d, 1H), 7.80 (m, 2H), 7.70 (d, 1H), 7.27 (t, 2H); $^{19}F$ NMR (CDCl$_3$) δ −62.62, −110.62; MS m/z 307 (M−1).

f) 1-[2-(4-Fluorophenyl)-6-(trifluoromethyl)pyrazolo[1,5-α]pyridin-3-yl]-2-propyn-1-ol To a cold (−78° C.) suspension of 2-(4-fluorophenyl)-6-(trifluoromethyl)pyrazolo[1,5-α]pyridine-3-carbaldehyde (11.4 g, 37.0 mmol) in tetrahydrofuran (100 mL) was added ethynylmagnesium bromide (111 mL, 0.5 M in tetrahydrofuran, 56 mmol). The reaction mixture was warmed to room temperature and stirred for 14 hours. The reaction mixture was poured into water and adjusted to neutral pH with 1N aqueous hydrochloric acid. The aqueous mixture was extracted with ethyl acetate. The combined extracts were washed with water and brine. The organic layer was dried over magnesium sulfate. Filtration and concentration provided 1-[2-(4-fluorophenyl)-6-(trifluoromethyl)pyrazolo[1,5-α]pyridin-3-yl]-2-propyn-1-ol (11.9 g, 96%) as a tan solid. $R_f$ 0.18 (4:1 hexanes:ethyl acetate); $^1H$ NMR (300 MHz, CDCl$_3$) δ 8.81 (s, 1H), 8.15 (d, 1H), 7.75 (m, 2H), 7.35 (d, 1H), 7.19 (t, 2H), 5.76 (s, 1H), 2.71 (d, 1H), 2.60 (d, 1H); MS m/z 335 (M+1).

g) 1-[2-(4-Fluorophenyl)-6-(trifluoromethyl)pyrazolo[1,5-α]pyridin-3-yl]-2-propyn-1-one To a cold (0° C.) solution of 1-[2-(4-fluorophenyl)-6-(trifluoromethyl)pyrazolo[1,5-α]pyridin-3-yl]-2-propyn-1-ol (5.00 g, 15.0 mmol) in chloroform (400 mL) was added manganese dioxide (130 g, 1.50 mol). The reaction mixture was stirred at 0° C. for 1.5 hours. The reaction mixture was filtered through a pad of Celite. The filtrate was concentrated in vacuo to provide 1-[2-(4-fluorophenyl)-6-(trifluoromethyl)pyrazolo[1,5-α]pyridin-3-yl]-2-propyn-1-one (3.44 g, 690/%) as a clear oil. $R_f$ 0.39 (4:1 hexanes:ethyl acetate); $^1H$ NMR (400 MHz, CDCl$_3$) δ 8.90 (s, 1H), 8.61 (d, 1H), 7.72–7.69 (m, 3H), 7.17 (m, 2H), 3.06 (s, 1H); MS m/333 (M+1).

h) N-Cyclopentyl-4-[2-(4-fluorophenyl)-6-(trifluoromethyl)pyrazolo[1,5-α]pyridin-3-yl]-2-pyrimidinamine To a suspension of N-cyclopentylguanidine hydrochloride (2.20 g, 13.5 mmol) in ethanol (70 mL) was added sodium ethoxide (4.5 mL, 3 M in ethanol, 14 mmol). The mixture was stirred at room temperature for 30 minutes, then cooled to 0° C. To this mixture was added 1-[2-(4-fluorophenyl)-6-(trifluoromethyl)pyrazolo[1,5-α]pyridin-3-yl]-2-propyn-1-one (3.44 g, 10.4 mmol) portionwise. The reaction mixture was stirred at 0° C. for 30 minutes, followed by room temperature for 15 hours. The reaction mixture was diluted with water (400 mL). The solid precipitate was collected on a filter to provide N-cyclopentyl-4-[2-(4-fluorophenyl)-6-(trifluoromethyl)pyrazolo[1,5-α]pyridin-3-yl]-2-pyrimidinamide (4.48 g, 98%) as an orange solid. $^1H$ NMR (400 MHz, CDCl$_3$) δ 8.84 (s, 1H), 8.51 (d, 1H), 8.11 (d, 1H), 7.64 (dd, 2H), 7.44 (d, 1H), 7.17 (t, 2H), 6.33 (d, 1H), 5.17 (d, 1H), 4.34 (m, 1H), 2.15–2.06 (m, 2H), 1.84–1.52 (m, 6H); $^{19}F$ NMR (CDCl$_3$): δ −62.70, −112.25 MS m/z 442 (M+1); mp 155–156° C.

i) N-Cyclopentyl-4-[2-(4-fluorophenyl)-6-(triethoxymethyl)pyrazolo[1,5-α]pyridin-3-yl]-2-pyrimidinamide To a dry round bottom flask was added sodium metal (1.9 g, 83 mmol). Ethanol (110 mL) was added and allowed to react with sodium at room temperature until completely dissolved. N-Cyclopentyl-4-[2-(4-fluorophenyl)-6-(trifluoromethyl)-pyrazolo[1,5-α]pyridin-3-yl]-2-pyrimidinamide (4.48 g, 10.1 mmol) was added and the reaction mixture was stirred at 60° C. for 18 hours. The reaction mixture was cooled and concentrated in vacuo to approximately one-fourth of the original volume. The resulting mixture was diluted with water and extracted with ethyl acetate. The organic layer was washed with water and brine, then dried over magnesium sulfate. Filtration and concentration provided N-cyclopentyl-4-[2-(4-fluorophenyl)-6-(triethoxymethyl)pyrazolo[1,5-α]pyridin-3-yl]-2-pyrimidinamide (4.86 g, 92%) as an off-white solid. $R_f$ 0.15 (4:1 hexanes:ethyl acetate); $^1H$ NMR (300 MHz, CDCl$_{13}$) δ 8.81 (s, 1H), 8.39 (d, 1H), 8.06 (d, 1H), 7.62 (m, 2H), 7.47 (d, 1H), 7.14 (t, 2H), 6.32 (d, 1H), 5.12 (d, 1H), 4.35 (m, 1H), 3.43 (q, 6H), 2.08 (m, 2H), 1.80–1.51 (m, 6H), 1.21 (t, 9H); MS m/z 520 (M+1).

j) Ethyl 3-[2-(cyclopentylamino)-4-pyrimidinyl]-2-(4-fluorophenyl)pyrazolo[1,5-α]pyridine-6-carboxylate To a solution of N-cyclopentyl-4-[2-(4-fluorophenyl)-6-(triethoxymethyl)pyrazolo-[1,5-α]pyridin-3-yl]-2-pyrimidinamide (1.0 g, 1.9 mmol) in acetone (40 mL) and water (10 mL) was added p-toluenesulfonic acid monohydrate (915 mg, 4.81 mmol). The reaction mixture was stirred at room temperature for 2 hours. The pH of the reaction mixture was adjusted to slightly basic using saturated aqueous sodium bicarbonate solution. The reaction mixture was concentrated in vacuo to one third of the original volume, then diluted with water. The precipitate was collected on a filter to provide ethyl 3-[2-(cyclopentylamino)-4-pyrimidinyl]-2-(4-fluorophenyl)pyrazolo[1,5-α]pyridine-6-carboxylate (722 mg, 85%) as an orange solid. $R_f$ 0.15 (4:1 hexanes:ethyl acetate); $^1H$ NMR (300 MHz, CDCl$_3$) δ 9.22 (s, 1H), 8.38 (d, 1H), 8.08 (br, 1H), 7.85 (d, 1H), 7.64 (m, 2H), 7.16 (t, 2H), 6.34 (s, 1H), 5.26 (br, 1H), 4.44 (q, 2H), 4.35 (br, 1H), 2.08 (m, 2H), 1.80–1.52 (m, 6H), 1.43 (t, 3H); MS m/z 446 (M+1).

k) 3-[2-(Cyclopentylamino)-4-pyrimidinyl]-2-(4-fluorophenyl)pyrazolo[1,5-α]pyridine-6-carboxylic acid hydrochloride To a solution of ethyl 3-[2-(cyclopentylamino)-4-pyrimidinyl]-2-(4-fluorophenyl)pyrazolo[1,5-α]pyridine-6-carboxylate (385 mg, 0.864 mmol) in dioxane (9 mL) and water (1 mL) was added lithium hydroxide monohydrate (109 mg, 2.60 mmol). The reaction mixture was heated at 95° C. for 5 hours. The reaction mixture was concentrated in vacuo. A suspension of the concentrated residue in water was acidified with 1 N aqueous hydrochloric acid. The solid precipitate was collected on a filter to provide 3-[2-(cyclopentylamino)-4-pyrimidinyl]-2-(4-fluorophenyl)-pyrazolo[1,5-α]pyridine-6-carboxylic acid hydrochloride (359 mg, 92%) as an orange solid. $^1H$ NMR (400 MHz, DMSO-d$_6$) δ 9.27 (s, 1H), 8.73 (br, 1H), 8.46 (br, 1H), 8.12 (br, 1H), 7.97 (br, 1H), 7.67 (m, 2H), 7.36 (t, 2H), 6.35 (br, 1H), 4.18 (br, 1H), 1.95 (br, 2H), 1.71 (br, 2H), 1.56 (br, 4H); MS m/z 418 (M+1).

l) tert-Butyl 3-[2-(cyclopentylamino)-4-pyrimidinyl]-2-(4-fluorophenyl)-pyrazolo[1,5-α]pyridin-6-ylcarbamate To a suspension of 3-[2-(cyclopentylamino)-4-pyrimidinyl]-2-(4-fluorophenyl)-pyrazolo[1,5-α]pyridine-6-carboxylic acid hydrochloride (60 mg, 0.13 mmol) in tertbutanol was added triethylamine (39 μL, 0.28 mmol) and diphenylphosphoryl azide (34 μL, 0.16 mmol). The reaction mixture was heated at reflux for 2.5 hours. The reaction mixture was cooled to room temperature and diluted with ethyl acetate. The organic layer was washed with 5% aqueous citric acid solution, water, saturated aqueous sodium bicarbonate solution, and brine. The organic layer was dried over sodium sulfate. Filtration and concentration followed by flash chromatography (39:1 dichloromethane:methanol) provided tert-butyl 3-[2-(cyclopentylamino)-4-pyrimidinyl]-2-(4-fluorophenyl)pyrazolo[1,5-α]pyridin-6-ylcarbamate (35 mg, 540/%) as a light green oil. $R_f$ 0.32 (29:1 dichloromethane:methanol); $^1$H NMR (400 MHz, CDCl$_3$) δ 8.95 (br, 1H), 8.35 (d, 1H), 8.01 (br, 1H), 7.60 (m, 2H), 7.19 (d, 1H), 7.12 (t, 2H), 6.51 (s, 1H), 6.31 (d, 1H), 4.34 (m, 1H), 2.07 (m, 2H), 1.90–1.52 (m, 6H), 1.53 (s, 9H); MS m/z 489 (M+1).

m) 3-[2-(Cyclopentylamino)-4-pyrimidinyl]-2-(4-fluorophenyl)pyrazolo[1,5-α]pyridin-6-amine dihydrochloride To a solution of tert-butyl 3-[2-(cyclopentylamino)-4-pyrimidinyl]-2-(4-fluorophenyl)pyrazolo[1,5-α]pyridin-6-ylcarbamate (35 mg, 0.072 mmol) in dichloromethane was added hydrogen chloride (144 μL, 4 N in dioxane, 0.58 mmol). The reaction mixture was stirred at room temperature for 18 hours. The reaction mixture was diluted with ether and the precipitated solids were collected on a filter to provide 3-[2-(cyclopentylamino)-4-pyrimidinyl]-2-(4-fluorophenyl)pyrazolo[1,5-α]pyridin-6-amine dihydrochloride (9 mg, 27%) as a brownish yellow solid. $^1$H NMR (300 MHz, DMSO-d$_6$) δ 8.25 (br, 1H), 7.97–7.91 (m, 2H), 7.53 (m, 2H), 7.26 (t, 2H), 7.06 (d, 1H), 6.15 (br, 1H), 4.14–3.85 (br, 1H), 1.85 (br, 2H), 1.65 (br, 2H), 1.48 (br, 4H); MS m/z 389 (M+1).

EXAMPLE 6

N-Cyclopentyl-3-[2-(cyclopentylamino)-4-pyrimidinyl]-2-(4-fluorophenyl)pyrazolo[1,5-α]pyridin-6-amine.

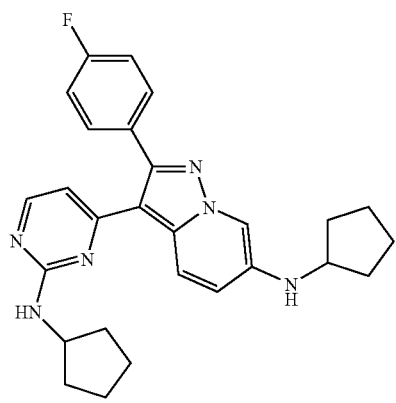

To a suspension of 3-[2-(cyclopentylamino)-4-pyrimidinyl]-2-(4-fluorophenyl)pyrazolo[1,5-α]pyridin-6-amine dihydrochloride (90 mg, 0.20 mmol) in 1,2-dichloroethane was added cyclopentanone (26 μL, 0.29 mmol), acetic acid (56 μL, 0.98), and sodium triacetoxyborohydride (82 mg, 0.39 mmol). The reaction mixture was stirred at room temperature 16 hours then quenched with water. The resultant mixture was diluted with ethyl acetate and saturated aqueous sodium bicarbonate solution. The organic layer was separated and washed with water and brine. The organic layer was dried over magnesium sulfate. Filtration and concentration followed by flash chromatography (4:1 hexanes:ethyl acetate to 7:3 hexanes:ethyl acetate) provided N-cyclopentyl-3-[2-(cyclopentylamino)-4-pyrimidinyl]-2-(4-fluorophenyl)pyrazolo[1,5-α]pyridin-6-amine (40 mg, 45%) as a green oil. $R_f$ 0.25 (2:1 hexanes:ethyl acetate); $^1$H NMR (300 MHz, CDCl$_3$) δ 8.25 (d, 1H), 8.00 (d, 1H), 7.79 (s, 1H), 7.61 (m, 2H), 7.13 (t, 2H), 6.86 (d, 1H), 6.32 (d, 1H), 5.23 (br, 1H), 4.36 (m, 1H), 3.72 (m, 1H), 3.54 (d, 1H), 2.14–2.02 (m, 4H), 1.81–1.51 (m, 12H); MS m/z 457 (M+1). To a solution of the product in ether was added 1 M HCl in ether. The precipitated solid was isolated to give the corresponding HCl salt.

EXAMPLE 7

3-[2-(Cyclopentylamino)-4-pyrimidinyl]-2-(4-fluorophenyl)-N-isopropylpyrazolo[1,5-α]pyridin-6-amine.

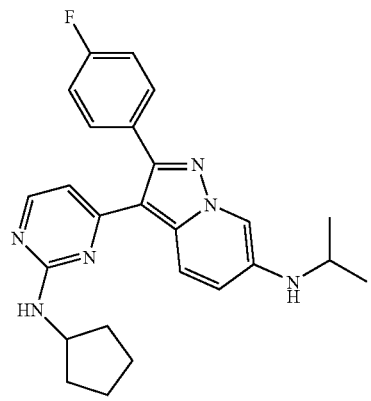

In a similar manner as described in Example 6 from 3-[2-(cyclopentylamino)-4-pyrimidinyl]-2-(4-fluorophenyl)pyrazolo[1,5-α]-6-amine dihydrochloride (40 mg, 0.087 mmol) and acetone was obtained 3-[2-(cyclopentylamino)-4-pyrimidinyl]-2-(4-fluorophenyl)-N-isopropylpyrazolo[1,5-α]-6-amine (16 mg, 43%) as a pale green solid. $R_f$ 0.21 (2:1 hexanes:EtOAc); $^1$H NMR (400 MHz, CD$_3$OD) δ 8.25 (d, 1H), 7.89 (d, 1H), 7.72 (s, 1H), 7.56 (m, 2H), 7.19 (d, 2H), 7.03 (d, 1H), 6.24 (d, 1H), 4.22 (m, 1H), 3.52 (m, 1H), 2.00 (m, 2H), 1.78–1.51 (m, 6H), 1.24 (d, 6H); MS m/z 431 M+1).

EXAMPLE 8

3-[2-(Cyclopentylamino)-4-pyrimidinyl]-2-(4-fluorophenyl)-N-(2-methoxyethyl)pyrazolo[1,5-α]pyridin-5-amine.

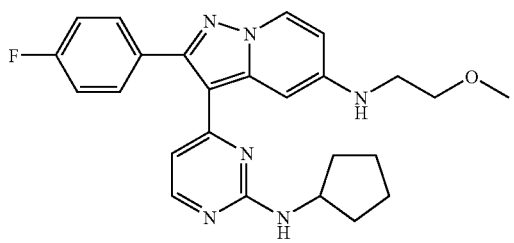

4-[5-Chloro-2-(4-fluorophenyl)pyrazolo[1,5-α]pyridin-3-yl]-N-cyclopentyl-2-pyrimidinamine (0.1 g, 0.25 mmol) and 2-methoxyethylamine were treated with rac-2,2'-bis(diphenylphosphino)-1,1'-binaphthyl, cesium carbonate and palladium (II) acetate as described in Example 2 to give, after purification by flash chromatography (1:1 hexanes-ethyl acetate), 3-[2-(cyclopentylamino)-4-pyrimidinyl]-2-(4-fluorophenyl)-N-(2-methoxyethyl)pyrazolo[1,5-α]pyridin-5-amine (65 mg, 59%) as a solid. $^1$H-NMR (CDCl$_3$): δ 8.2 (d, 1H), 7.9 (d, 1H), 7.55 (m, 2H), 7.4 (m, 1H), 7.1 (t, 2H), 6.32 (dd, 1H), 6.2 (d, 1H), 5.3 (broad s, 1H), 4.54 (t, 1H), 4.4 (m, 1H), 3.65 (m, 2H), 3.4 (s, 3H), 3.35 (m, 2H), 2.1 (m, 2H), 1.5–1.8 (m, 6H); $^{19}$F-NMR (CDCl$_3$): δ –113.46; MS m/z 447 (M+1).

EXAMPLE 9

3-[2-(Cyclopentylamino)-4-pyrimidinyl]-2-(4-fluorophenyl)-N-isopropylpyrazolo[1,5-α]pyridin-5-amine.

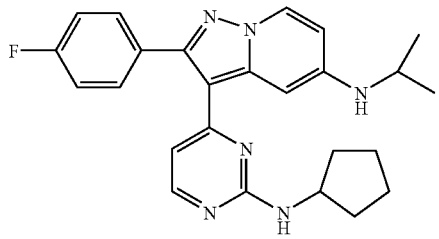

4-[5-Chloro-2-(4-fluorophenyl)pyrazolo[1,5-α]pyridin-3-yl]-N-cyclopentyl-2-pyrimidinamine (0.1 g, 0.25 mmol) and isopropylamine were treated with rac-2,2'-bis(diphenylphosphino)-1,1'-binaphthyl, cesium carbonate and palladium (II) acetate as described in Example 2 to give, after purification by flash chromatography (1:1 hexanes-ethyl acetate), 3-[2-(cyclopentylamino)-4-pyrimidinyl]-2-(4-fluorophenyl)-N-isopropylpyrazolo[1,5-α]pyridin-5-amine (70 mg, 66%) as a solid. $^1$H-NMR (CDCl$_3$): δ 8.17 (d, 1H), 7.9 (d, 1H), 7.58 (q, 2H), 7.4 (m, 1H), 7.15 (t, 2H), 6.24 (dd, 1H), 6.2 (d, 1H), 5.25 (broad s, 1H), 4.4 (m, 1H), 3.95 (d, 1H), 3.75 (m, 1H), 2.1 (m, 2H), 1.5–1.8 (m, 6H), 1.30 (d, 6H); $^{19}$F-NMR (CDCl$_3$): δ –113.45; MS m/z 431 (M+1).

EXAMPLE 10

N-Cyclopentyl-3-[2-(cyclopentylamino)-4-pyrimidinyl]-2-(4-methoxyphenyl)-pyrazolo[1,5-α]pyridin-5-amine.

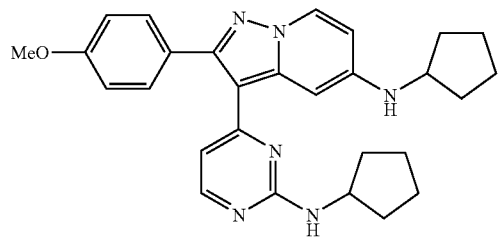

a) 2-(4-Chloro-2-pyridinyl)-1-(4-methoxyphenyl)ethanone

To a cold (0° C.) solution of 4-chloro-2-picoline (10 g, 78.4 mmol) and ethyl 4-methoxybenzoate (14.1 g, 78.4 mmol) in tetrahydrofuran (100 mL) was added lithium bis(trimethylsilyl)amide (157 mL, 1.0 M in tetrahydrofuran, 157 mmol) dropwise via a pressure equalizing funnel over half an hour. Upon complete addition, the ice bath was removed and the resulting solution was heated at 45° C. for 15 hours. The mixture was cooled to room temperature, and the solution was concentrated. Methanol was added to quench the reaction, resulting in the formation of a yellow precipitate. The precipitate was collected by filtration and dried to give the product as a mixture of enol and ketone tautomers. MS m/z 262 (M+1).

b) 2-(4-Chloro-2-pyridinyl)-1-(4-methoxyphenyl)ethanone oxime

To a solution of 2-(4-chloro-2-pyridinyl)-1-(4-methoxyphenyl)ethanone in methanol (200 mL) was added hydroxylamine hydrochloride (27.2 g, 392 mmol) followed by the addition of a sodium hydroxide solution (15.7 g, 392 mmol in 50 mL of water). The resulting suspension was heated at reflux for 1 hour and then allowed to cool to room temperature. The mixture was concentrated and water was added to the resulting slurry. A white precipitate formed, which was collected by filtration, washed with water and dried to give 2-(4-chloro-2-pyridinyl)-1-(4-methoxyphenyl)ethanone oxime (11.8 g) as a white solid. $^1$H NMR (CDCl$_3$): δ 8.47 (d, 1H), 7.72 (d, 2H), 7.36 (d, 1H), 7.19 (dd, 1H), 6.91 (d, 2H), 4.43 (s, 2H), 3.84 (s, 3H); MS m/z 277 (M+1).

c) 5-Chloro-2-(4-methoxyphenyl)pyrazolo[1,5-α]pyridine

To a solution of 2-(4-chloro-2-pyridinyl)-1-(4-methoxyphenyl)ethanone oxime (11.8 g, 42.6 mmol) in 1,2-dimethoxyethane (200 mL) at 0° C. was added trifluoroacetic anhydride (6.3 mL, 44.8 mmol), keeping the temperature below 10° C. during the addition. After the addition was complete, the reaction was warmed to 15° C. The solution was then cooled to 4° C. and a solution of triethylamine (12.5 mL, 89.5 mmol) in 1,2-dimethoxyethane (15 mL) was added over a period of 0.5 hours. The mixture was allowed to warm to room temperature and was stirred at room temperature for 5 hours. To this mixture was added iron(II) chloride (0.11 g, 0.85 mmol) and the reaction was heated at 75° C. for 15 hours. The reaction mixture was poured into water (300 mL). The resulting suspension was extracted with ethyl acetate. The organic phase was dried (magnesium sulfate), filtered and concentrated to a solid. This solid was recrystallized from methanol to give 5-chloro-2-(4-methoxyphenyl)pyrazolo[1,5-α]pyridine (6.64 g, 60%) as white needles. $^1$H NMR (CDCl$_3$): δ 8.35 (d, 1H), 7.86 (d, 2H), 7.46 (d, 1H), 6.97 (d, 2H), 6.67 (d, 1H), 6.65 (s, 1H), 3.85 (s, 3H); MS m/z 259 (M+1).

d) 1-[5-(Chloro)-2-(4-methoxyphenyl)pyrazolo[1,5-α]pyridin-3-yl]ethanone

To a solution of 5-chloro-2-(4-methoxyphenyl)pyrazolo[1,5-α]pyridine (3.0 g, 11.6 mmol) in toluene (100 mL) at room temperature was added acetic anhydride (1.6 mL, 17.4 mmol). Boron trifluoride diethyletherate (1.8 mL, 13.9 mmol) was then added dropwise and the resulting solution was heated at reflux for 4 hours. The reaction mixture was cooled to room temperature and quenched by the dropwise addition of saturated aqueous sodium bicarbonate. The reaction was extracted with ethyl acetate, and the ethyl acetate phase washed with brine, dried (magnesium sulfate), filtered and concentrated. The residue was purified by recrystallization from ethyl acetate-hexanes to give 1-[5-(chloro)-2-(4-methoxyphenyl)pyrazolo[1,5-α]pyridin-3-yl]ethanone (2.31 g, 66%). $^1$H NMR (CDCl$_3$): δ 8.44 (d, 1H), 8.40 (d, 1H), 7.49 (d, 2H), 7.02 (d, 2H), 6.97 (dd, 1H), 3.85 (s, 3H), 2.15 (s, 3H); MS m/z 301 (M+1).

e) 1-[5-(Cyclopentylamino)-2-(4-methoxyphenyl)pyrazolo[1,5-α]pyridin-3-yl]ethanone To a solution of 1-[5-(chloro)-2-(4-methoxyphenyl)pyrazolo[1,5-α]pyridin-3-yl]ethanone (1.77 g, 5.88 mmol) in toluene (60 mL) was added successively racemic-2,2'-bis(diphenylphosphino)-1,1'-binaphthyl (220 mg, 0.35 mmol), cesium carbonate (2.88 g, 8.83 mmol), cyclopentylamine (2.9 mL, 29.4 mmol), and palladium (II) acetate (53 mg, 0.24 mmol). The resulting mixture was stirred at 95° C. for 3 days, at which time the reaction was judged complete by thin layer chromatography. The solution was cooled to room temperature and diethyl ether and water were added to the reaction mixture. The phases were separated, and the aqueous phase again extracted with diethyl ether. The combined organic phases were dried (magnesium sulfate), filtered and concentrated. The resulting residue was purified by flash chromatography (3:2 hexanes:ethyl acetate) to give 1-[5-(cyclopentylamino)-2-(4-methoxyphenyl)pyrazolo[1,5-α]pyridin-3-yl]ethanone (1.14 g, 56%) as a yellow solid. $^1$H NMR (CDCl$_3$): δ 8.19 (d, 1H), 7.52 (d, 2H), 7.45 (d, 1H), 7.03 (d, 2H), 6.35 (dd, 1H), 4.15 (broad s, 1H), 3.98 (m, 1H), 3.91 (s, 3H), 2.21–2.15 (m, 2H), 2.11 (s, 3H), 1.79–1.54 (m, 6H); MS m/z 350 (M+1).

f) 1-[5-(Cyclopentylamino)-2-(4-methoxyphenyl)pyrazolo[1,5-α]pyridin-3-yl]-3-(dimethylamino)-2-propen-1-one A solution of 1-[5-(cyclopentylamino)-2-(4-methoxyphenyl)pyrazolo[1,5-α]pyridin-3yl]ethanone (1.14 g, 3.26 mmol) in N,N-dimethylformamide dimethyl acetal (25 mL) was heated at reflux for 5 days. The mixture was allowed to cool to room temperature. Water was added and the resulting mixture was extracted with ethyl acetate. The organic phase was dried (magnesium sulfate), filtered and concentrated. The resulting residue was crystallized from ethyl acetate to give 1-[5-(cyclopentylamino)-2-(4-methoxyphenyl)pyrazolo[1,5-α]pyridin-3-yl]-3-(dimethylamino)-2-propen-1-one (1.05 g, 80%) as a yellow solid. $^1$H NMR (CDCl$_3$): δ 8.11 (d, 1H), 7.56 (m, 3H), 7.41 (d, 1H), 6.95 (d, 2H), 6.22 (dd, 1H), 5.07 (d, 1H), 4.11 (d, 1H), 3.95 (m, 1H), 3.84 (s, 3H), 3.0–2.3 (broad, 6H), 2.12 (m, 2H), 1.74–1.48 (m, 6H); MS m/z 405 (M+1).

g) N-Cyclopentyl-3-[2-(cyclopentylamino)-4-pyrimidinyl]-2-(4-methoxyphenyl)-pyrazolo[1,5-α]pyridin-5-amine To a solution of 1-[5-(cyclopentylamino)-2-(4-methoxyphenyl)pyrazolo[1,5-α]pyridin-3-yl]-3-(dimethylamino)-2-propen-1-one (1.05 g, 2.60 mmol) in N,N-dimethylformamide (20 mL) was added N-cyclopentyl guanidine hydrochloride (1.27 g, 7.79 mmol; Prepared by modification of a procedure from Bannard, R. A. B. et al., *Can. J. Chem.* 1958, 36,1541–1549), followed by potassium carbonate (0.54 g, 3.89 mmol). The resulting solution was heated at reflux for 15 hours. Upon cooling to room temperature, water was added. The mixture was extracted with ethyl acetate. The ethyl acetate phase was washed with brine, dried (magnesium sulfate), filtered and concentrated in vacuo. The resulting residue was purified by flash chromatography (4:6 ethyl acetate:hexane) to give N-cyclopentyl-3-[2-(cyclopentylamino)-4-pyrimidinyl]-2-(4-methoxyphenyl)-pyrazolo[1,5-α]pyridin-5-amine (1.06 g, 87%) as a yellow solid. $^1$H NMR (CDCl$_3$): δ 8.15 (d, 1H), 7.91 (d, 1H), 7.51 (d, 2H), 7.41 (d, 1H), 6.94 (d, 2H), 6.26 (d, 1H), 6.22 (dd, 1H). 5.11 (d, 1H), 4.42 (m, 1H), 4.09 (d, 1H), 3.88 (m, 1H), 3.85 (s, 3H), 2.10–2.01 (m, 4H), 1.76–1.52 (m, 12H); MS m/z 469 (M+1).

EXAMPLE 11

4-[5-Chloro-2-(4-methoxyphenyl)pyrazolo[1,5-α]pyridin-3-yl]-N-cyclopentyl-2-pyrimidinamine

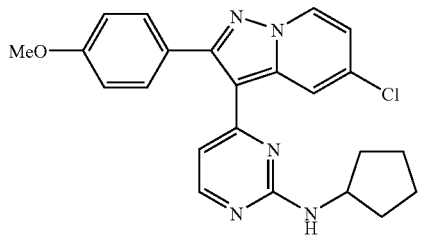

a) 5-Chloro-2-(4-methoxyphenyl)pyrazolo[1,5-α]pyridine-3-carbaldehyde

To N,N-dimethylformamide (20 mL) at 0° C. was added phosphorous oxychloride (0.54 mL, 7.8 mmol). After the addition was complete, the mixture was warmed to room temperature and stirred for 1 hour. To this was added 5-chloro-2-(4-methoxyphenyl)pyrazolo[1,5-α]pyridine[1,5-α]pyridine (1.0 g, 3.86 mmol) and the resultant solution was stirred 2 hours. Water was added, followed by dichloromethane. The aqueous layer was extracted with dichloromethane. The combined organics were washed with brine, dried over magnesium sulfate, filtered and concentrated. A white crystalline compound, 5-chloro-2-(4-methoxyphenyl) pyrazolo[1,5-α]pyridine-3-carbaldehyde (0.9 g, 81%), was obtained. ¹H NMR (CDCl₃): δ 10.12 (s, 1H), 8.52 (d, 1H), 8.47 (d, 1H), 7.76 (d, 2H), 7.11–7.06 (m, 3H), 3.93 (s, 3H); MS m/z 287 (M+1).

b) 1-[5-Chloro-2-(4-methoxyphenyl)pyrazolo[1,5-α] pyridin-3-yl]-2-propyn-1-ol

To a cold (-78° C.) suspension of 5-chloro-2-(4-methoxyphenyl)pyrazolo[1,5-α]pyridine-3-carbaldehyde (0.90 g, 3.14 mmol) in tetrahydrofuran (50 mL) was added ethynylmagnesium bromide (7.5 mL, 0.5 M in tetrahydrofuran, 3.77 mmol) dropwise. The reaction mixture was stirred at -78° C. for 1 hour, then at room temperature for 4 hours. The resultant solution was poured into saturated aqueous sodium bicarbonate and extracted with ethyl acetate. The organic layer was washed with water and brine and the combined organics were dried over magnesium sulfate. Filtration and concentration provided 1-[5-chloro-2-(4methoxyphenyl) pyrazolo[1,5-α]pyridin-3-yl]-2-propyn-1-ol (1.05 g, 100%) as a white solid. ¹H NMR (CDCl₃) δ 8.40 (d, 1H), 8.05 (s, 1H), 7.72 (d, 2H), 7.05 (d, 2H), 6.80 (dd, 1H), 5.78 (s, 1H), 3.91 (s, 3H), 2.74 (s, 1H), 2.53 (s, 1H); MS m/z 313 (M+1).

c) 1-[5-Chloro-2-(4-methoxyphenyl)pyrazolo[1,5-α] pyridin-3-yl]-2-propyn-1one

To a solution of 1-[5-chloro-2-(4-methoxyphenyl)pyrazolo[1,5-α]pyridin-3-yl]-2-propyn-1-ol (1.05 g, 3.14 mmol) in chloroform (100 mL) was added manganese dioxide (6.82 g, 78.5 mmol). The reaction mixture was stirred at room temperature for 3.5 hours. The suspension was filtered through a pad of Celite and the filtrate was concentrated to give 1-[5-chloro-2-(4-methoxyphenyl)pyrazolo[1,5-α]pyridin-3-yl]-2-propyn-1-one (0.99 g, 100%o) as a pale yellow solid. ¹H NMR (CDCl₃) δ 8.50 (d, 1H), 8.46 (d, 1H), 7.64 (d, 2H), 7.04 (dd, 1H), 6.98 (d, 2H), 3.87 (s, 3H), 2.99 (s, 1H); MS m/z 295 (M+1).

d) 4-[5-Chloro-2-(4-methoxyphenyl)pyrazolo[1,5-α] pyridin-3-yl]-N-cyclopentyl-2-pyrimidinamine.

Sodium ethylate (0.7 mL (2.09 mmol), 210% in ethanol) and cyclopentyl guanidine hydrochloride (0.47 g, 2.88 mmol) were added sequentially to ethanol (30 mL). The resulting solution was stirred at room temperature for 30 minutes. 1-[5-chloro-2-(4-methoxyphenyl)pyrazolo[1,5-α] pyridin-3-yl]-2-propyn-1-one (0.5 g, 1.61 mmol) was added, and the suspension was stirred at room temperature for 2 days. The reaction was quenched by the addition of water. The aqueous phase was extracted by ethyl acetate. The organics were combined, washed with brine and dried over magnesium sulfate. Filtration and concentration gave a solid. This solid was recrystallized from methanol to give 4-[5-chloro-2-(4-methoxyphenyl)pyrazolo[1,5-α]pyridin-3-yl]-N-cyclopentyl-2-pyrimidinamine (0.45 g, 66%) as a pale yellow solid. ¹H NMR (CDCl₃) δ 8.59 (b, 1H), 8.42 (d, 1H), 8.05 (d, 1H), 7.59 (d, 2H), 7.03 (d, 2H), 6.91 (dd, 1H), 6.39 (d, 1H), 5.34 (broad s, 1H), 4.42 (m, 1H), 3.92 (s, 3H), 2.17 (m, 2H), 1.86–1.60 (m, 6H); MS m/z 420 (M+1).

EXAMPLE 12

3-[2-(Cyclopentylamino)-4-pyrimidinyl]-N-isopropyl-2-(4-methoxyphenyl)pyrazolo[1,5-α]pyridin-5-amine

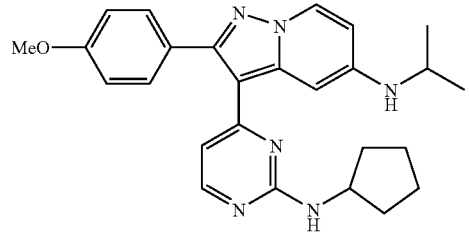

To a solution of 4-[5-chloro-2-(4-methoxyphenyl)pyrazolo[1,5-α]pyridin-3-yl]-N-cyclopentyl-2-pyrimidinamine (100 mg, 0.24 mmol) in cyclopentylamine (50 mL) was added successively racemic-2,2'-bis(diphenylphosphino)-1, 1'-binaphthyl (71 mg, 0.11 mmol), cesium carbonate (155 mg, 0.48 mmol) and palladium (II) acetate (16 mg, 0.07 mmol). The resultant mixture was heated to 95° C. for 2 days at which time the reaction was judged complete by thin layer chromatography. The solution was cooled to room temperature and ethyl acetate was added. The organic layer was washed with water and brine. The aqueous layer was extracted with ethyl acetate and the combined organics dried over magnesium sulfate. Filtration and concentration, followed by flash chromatography (3:2 hexanes:ethyl acetate) provided 3-[2-(cyclopentylamino)-4-pyrimidinyl]N-isopropyl-2-(4-methoxyphenyl)pyrazolo[1,5-α]pyridin-5-amine (62 mg, 58%) as a yellow solid. ¹H NMR (CDCl₃) δ 8.13 (d, 1H), 7.91 (d, 1H), 7.50 (d, 2H), 7.44 (d, 1H), 6.93 (d, 2H), 6.25 (d, 1H), 6.19 (dd, 1H), 5.25 (d, 1H), 4.41 (m, 1H), 4.05 (d, 1H), 3.83 (s, 3H), 3.69 (m, 1H), 2.08–2.02 (m, 2H), 1.71–1.48 (m, 6H), 1.23 (d, 6H); MS m/z 443 (M+1).

EXAMPLE 13

4Bromo-N-cyclopentyl-3-[2-(cyclopentylamino) pyrimidin-4-yl]-2-(4-fluorophenyl)pyrazolo[1,5-α] pyridin-5-amine

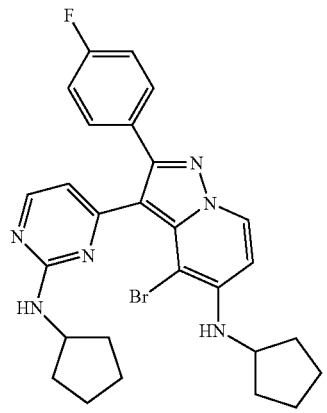

N-Cyclopentyl-3-[2-(cyclopentylamino)pyrimidin-4-yl]-2-(4-fluorophenyl)pyrazolo-[1,5-α]pyridin-5-amine (100 mg, 0.22 mmol) was dissolved in dichloromethane (5 mL) and treated with N-bromosuccinimide (40 mg, 0.22 mmol). The reaction mixture was stirred for 10 minutes. Additional dichloromethane and 1N aqueous sodium hydroxide was added. The phases were separated, the organic phase washed with water, dried (magnesium sulfate), filtered and concentrated to dryness to give 100 mg of the title compound as a yellow foam. $^1$H NMR (CDCl$_3$): δ 8.32 (d, 1H), 8.22 (d, 1H), 7.53 (q, 2H), 7.04 (t, 2H), 6.53 (m, 2H), 5.17 (d, 1H), 4.72 (d, 1H), 4.33 (m, 1H), 3.95 (m, 1H), 2.1–1.4 (m, 16H); $^{19}$F NMR (CDCl$_3$): δ –113.97; MS m/z 536 (M+1).

EXAMPLE 14

4-Chloro-N-cyclopentyl-3-[2-(cyclopentylamino) pyrimidin-4-yl]-2-(4-fluorophenyl)pyrazolo[1,5-α] pyridin-5-amine

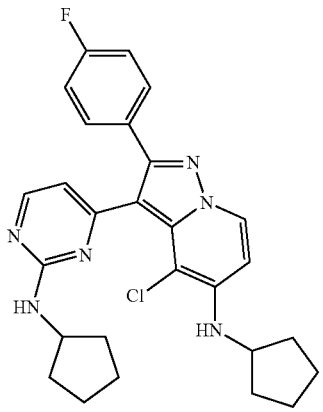

The title compound was synthesized in a similar manner as described above. $^1$H NMR (CDCl$_3$): δ 8.30 (d, 1H), 8.22 (d, 1H), 7.54 (q, 2H), 7.05 (t, 2H), 6.53 (m, 2H), 5.14 (d, 1H), 4.62 (d, 1H), 4.32 (m, 1H), 3.97 (m, 1H), 2.1–1.4 (m, 16H); $^{19}$F NMR (CDCl$_3$): δ –113.99; MS m/z 492 (M+1).

EXAMPLE 15

4-Bromo-N-cyclopentyl-3-[2-(cyclopentylamino) pyrimidin-4-yl]-2-(4-methoxyphenyl)pyrazolo[1,5-α]pyridin-5-amine

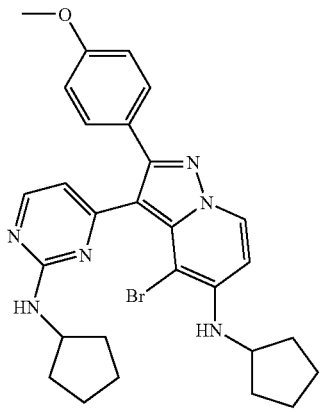

The title compound was synthesized in a similar manner as described above. $^1$H NMR (CDCl$_3$): δ 8.32 (d, 1H), 8.20 (d, 1H), 7.48 (d, 2H), 6.87 (d, 2H), 6.54 (d, 1H), 6.49 (d, 1H), 5.20 (d, 1H), 4.70 (d, 1H), 4.35 (m, 1H), 3.95 (m, 1H), 3.83 (s, 3H), 2.1–1.4 (m, 16H); MS m/z 549 (M+1).

EXAMPLE 16

4-Chloro-N-cyclopentyl-3-[2-(cyclopentylamino) pyrimidin-4-yl]-2-(4-methoxyphenyl)pyrazolo[1,5-α]pyridin-5-amine

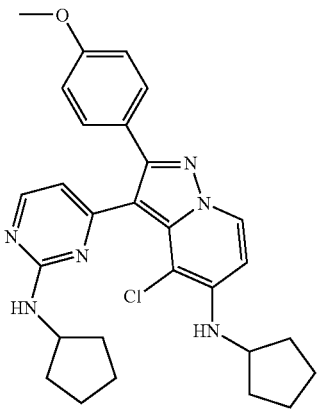

The title compound was synthesized in a similar manner as described above. $^1$H NMR (CDCl$_3$): δ 8.30 (d, 1H), 8.20 (d, 1H), 7.48 (d, 2H), 6.88 (d, 2H), 6.54 (d, 1H), 6.52 (d, 1H), 5.17 (d, 1H), 4.60 (d, 1H), 4.32 (m, 1H), 3.97 (m, 1H), 3.84 (s, 3H), 2.1–1.4 (m, 16H); MS m/z 504 (M+1).

EXAMPLE 17

N-Butyl-3-[2-(butylamino)pyridin-4-yl]-2-(4-fluorophenyl)pyrazolo[1,5-α]pyridin-4-amine

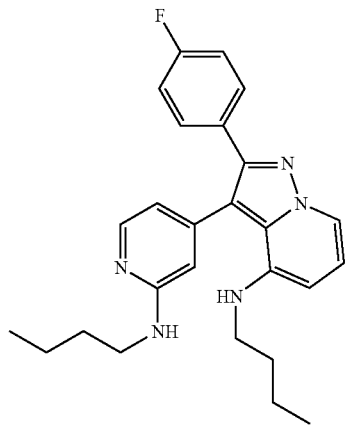

The title compound was made in a similar manner as described above. $^1$H NMR (CDCl$_3$): δ 8.01 (m, 2H), 7.50 (m, 2H), 7.35 (m, 1H), 7.06 (m, 2H), 6.78 (t, 1H), 6.66 (d, 1H), 6.46 (s, 1H), 6.17 (d, 1H), 5.93 (bs, 1H), 3.20 (m, 2H), 3.14 (m, 2H), 1.56 (m, 4H), 1.42 (m, 2H), 1.32 (m, 2H), 0.94 (M, 6H); MS m/z 432 (M+1).

EXAMPLE 18

4-{5-(Cyclopentylamino)-3-[2-(cyclopentylamino)-4-pyrimidinyl]pyrazolo[1,5-α]pyridin-2-yl}phenol

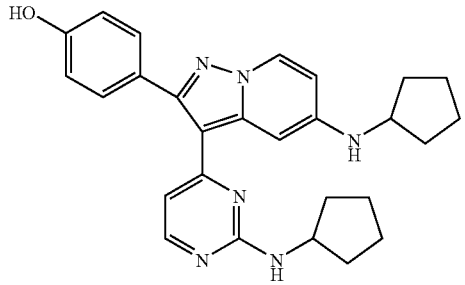

Treatment of N-cyclopentyl-3-[2-(cyclopentylamino)-4-pyrimidinyl]-2-(4-methoxyphenyl)pyrazolo[1,5-α]pyridin-5-amine (500 mg, 1.07 mmol) in dichloromethane with boron tribromide, followed by aqueous workup, gave 4-{5-(cyclopentylamino)-3-[2-(cyclopentylamino)-4-pyrimidinyl]pyrazolo[1,5-α]pyridin-2-yl}phenol (390 mg, 81%) as a yellow solid. $^1$H NMR (CD$_3$OD) δ 8.16 (d, 1H), 7.85 (d, 1H), 7.40 (m, 3H), 6.90 (d, 2H), 6.53 (dd, 1H), 6.27 (d, 1H), 4.44 (m, 1H), 3.92 (m, 1H), 2.11 (m, 4H), 1.84–1.58 (m, 12H). MS m/z 455 (M+1).

EXAMPLE 19

N-Cyclopentyl-3-[2-(cyclopentylamino)-4-pyrimidinyl]-2-(4-isobutoxyphenyl)pyrazolo[1,5-α]pyridin-5-amine

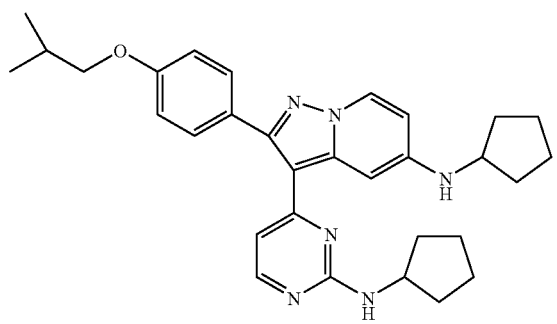

Treatment of 4-{5-(cyclopentylamino)-3-[2-(cyclopentylamino)-4-pyrimidinyl]pyrazolo[1,5-α]pyridin-2-yl}phenol (100 mg, 0.22 mmol) in N,N-dimethylformamide (5 mL) with isobutyl bromide and potassium carbonate gave N-cyclopentyl-3-[2-(cyclopentylamino)-4-pyrimidinyl]-2-(4-isobutoxyphenyl)pyrazolo[1,5-α]pyridin-5-amine (83 mg, 740/%) as a pale yellow solid. $^1$H NMR (CDCl$_3$) δ 8.14 (d, 1H), 7.92 (d, 1H), 7.49 (d, 2H), 7.41 (d, 1H), 6.93 (d, 2H), 6.27 (d, 1H), 6.20 (dd, 1H), 5.10 (d, 1H), 4.41 (m, 1H), 4.13 (d, 1H), 3.87 (m, 1H), 3.76 (d, 2H), 2.05 (m, 5H), 1.76–1.52 (m, 12H), 1.02 (d, 6H). MS m/z 511 (M+1).

EXAMPLE 20

N-Cyclopentyl-3-[2-(cyclopentylamino)-4-pyrimidinyl]-2-[4-(cyclopropylmethoxy)phenyl]pyrazolo[1,5-α]pyridin-5-amine

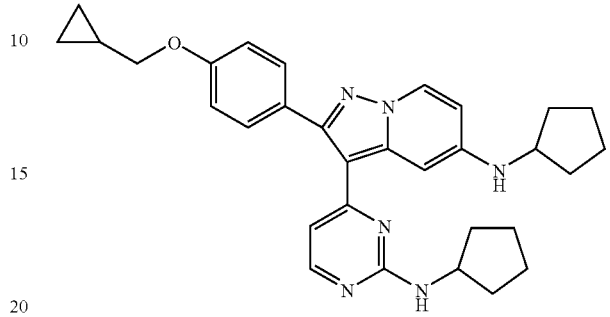

In a similar manner described above from 4-{5-(cyclopentylamino)-3-[2-(cyclopentylamino)-4-pyrimidinyl]pyrazolo[1,5-α]pyridin-2-yl}phenol (100 mg, 0.22 mmol) was obtained N-cyclopentyl-3-[2-(cyclopentylamino)-4-pyrimidinyl]-2-[4-(cyclopropylmethoxy)phenyl]pyrazolo[1,5-α]pyridin-5-amine (69 mg, 62%) as a yellow solid. $^1$H NMR (CDCl$_3$) δ 8.11 (d, 1H), 7.91 (d, 1H), 7.48 (d, 2H), 7.41 (d, 1H), 6.92 (d, 2H), 6.25 (d, 1H), 6.19 (dd, 1H), 5.18 (bs, 1H), 4.40 (m, 1H), 4.19 (bs, 1H), 3.83 (m, 3H), 2.04 (m, 4H), 1.70–1.49 (m, 12H), 1.25 (m, 1H), 0.63 (m, 2H), 0.35 (m, 2H). MS m/z 509 (M+1).

EXAMPLE 21

Biological Activity

In the following example, "MEM" means Minimal Essential Media; "FBS" means Fetal Bovine Serum; "NP40" and "Igepal" are detergents; "MOI" means Multiplicity of Infection; "NaOH" means sodium hydroxide; "MgC$_2$" means magnesium chloride; "dATP" means deoxyadenosine 5' triphosphate; "dUTP" means deoxyuridine 5' triphosphate; "dCTP" means dexoxycytidine 5' triphosphate; "dGTP" means deoxyguanosine 5' triphosphate; "GuSCN" means Guanidinium thiocyanate; "EDTA" means ethylenediamine tetraacetic acid; "TE" means Tris-EDTA; "SCC" means sodium chloride/sodium citrate; "APE" means a solution of ammonia acetate, ammonia phosphate, EDTA; "PBS" means phosphate buffered saline; and "HRP" means horseradish peroxidase.

a) Tissue Culture and HSV Infection

Vero 76 cells were maintained in MEM with Earle's salts, L-glutamine, 8% FBS (Hyclone, A-1111-L) and 100 units/mL Penicillin-100 μg/mL Streptomycin. For assay conditions, FBS was reduced to 2%. Cells are seeded into 96-well tissue culture plates at a density of 5×10$^4$ cells/well after being incubated for 45 min at 37° C. in the presence of HSV-1 or HSV-2 (MOI=0.001). Test compounds are added to the wells and the plates are incubated at 37° C. for 40–48 hours. Cell lysates are prepared as follows: media was removed and replaced with 150 μL/well 0.2 N NaOH with 1% Igepal CA 630 or NP-40. Plates were incubated up to 14 days at room temperature in a humidified chamber to prevent evaporation.

(b) Preparation of Detection DNA

For the detection probe, a gel-purified, digoxigenin-labeled, 710-bp PCR fragment of the HSV UL-15 sequence was utilized. PCR conditions included 0.5 µM primers, 180 µM dTTP, 20 µM dUTP-digoxigenin (Boehringer Mannheim 1558706), 200 µM each of dATP, dCTP, and dGTP 1×PCR Buffer II (Perkin Elmer), 2.5 mM MgCl$_2$, 0.025 units/µL of AmpliTaq Gold polymerase (Perkin Elmer), and 5 ng of gel-purified HSV DNA per 100 µL Extension conditions were 10 min at 95° C., followed by 30 cycles of 95° C. for 1 min, 55° C. for 30 sec. and 72° C. for 2 min. The amplification was completed with a 10-min incubation at 72° C. Primers were selected to amplify a 728 bp probe spanning a section of the HSV1 UL15 open reading frame (nucleotides 249–977). Single-stranded transcripts were purified with Promega M13 Wizard kits. The final product was mixed 1:1 with a mixture of 6 M GuSCN, 100 mM EDTA and 200 µg/mL herring sperm DNA and stored at 4° C.

(c) Preparation of Capture Plates

The capture DNA plasmid (HSV UL13 region in pUC) was linearized by cutting with Xba I, denatured for 15 min at 95° C. and diluted immediately into Reacti-Bind DNA Coating Solution (Pierce, 17250, diluted 1:1 with TE buffer, pH 8) at 1 ng/µL 75 µL/well were added to Corning (#3922 or 9690) white 96-well plates and incubated at room temperature for at least 4 hrs before washing twice with 300 µL/well 0.2×SSC/0.05% Tween-20 (SSC/T buffer). The plates were then incubated overnight at room temperature with 150 µL/well 0.2 N NaOH, 1% IGEPAL and 10 µg/mL herring sperm DNA.

(d) Hybridization

Twenty-seven (27) µL of lysate was combined with 45 µL of hybridization solution (final concentration: 3M GuSCN, 50 mM EDTA, 100 µg/ml salmon sperm DNA, 5×Denhardt's solution, 0.25×APE, and 5 ng of the digoxigenin-labeled detection probe). APE is 1.5 M NH$_4$-acetate, 0.15 M NH$_4$H$_2$ phosphate, and 5 mM EDTA adjusted to pH 6.0 Mineral oil (50 µL) was added to prevent evaporation. The hybridization plates were incubated at 95° C. for 10 minutes to denature the DNA, then incubated at 42° C. overnight. The wells were washed 6× with 300 µl/well SSC/T buffer then incubated with 75 µL/well anti-digoxigenin-HRP-conjugated antibody (Boehringer Mannheim 1207733, 1:5000 in TE) for 30 min at room temperature. The wells were washed 6× with 300 µL/well with PBS/0.05% Tween-20 before 75 µL/well SuperSignal LBA substrate (Pierce) was added. The plates were incubated at room temperature for 30 minutes and chemiluminescence was measured in a Wallac Victor reader.

Results

The following results were obtained for HSV-1.

| Example No. | IC$_{50}$ (µM) |
| --- | --- |
| 2 | 0.5 |
| 3 | 5 |
| 4 | 2 |

| Example No. | IC$_{50}$ (µM) |
| --- | --- |
| 5 | 0.24 |
| 6 | 1 |
| 7 | 1.2 |
| 8 | 1 |
| 9 | 2.9 |
| 10 | 0.2 |
| 12 | 0.8 |
| 13 | 3.0 |
| 14. | 1.9 |
| 15 | 3.5 |
| 16 | 2.8 |
| 17 | 2.5 |
| 18 | 1.2 |
| 19 | 0.5 |
| 20 | 0.3 |

The results demonstrate that the compounds of the present invention are useful for the treatment and prophylaxis of herpes viral infections.

The invention claimed is:

1. A compound of formula (I):

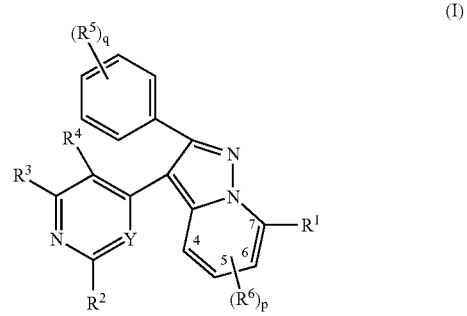

wherein:

$R^1$ is H;

$R^2$ is selected from the group consisting of halo, alkyl, cycloalkyl, alkenyl, cycloalkenyl, Ay, Het, —OR$^7$, —OAy, —OHet, —OR$^{10}$Het, —S(O)$_n$R$^9$, —S(O)$_n$Ay, —S(O)$_n$Het, —S(O)$_n$NR$^7$R$^8$, —NR$^7$R$^8$, —NHHet, —NHR$^{10}$Het, —NHR$^{10}$Ay, —R$^{10}$NR$^7$R$^8$ and —R$^{10}$NR$^7$Ay;

each $R^7$ and $R^8$ are the same or different and are independently selected from the group consisting of H, alkyl, cycloalkyl, alkenyl, cycloalkenyl, —OR$^9$, —C(O)R$^9$, —CO$_2$R$^9$, —C(O)NR$^9$R$^{11}$, —C(S)NR$^9$R$^{11}$, —C(NH)NR$^9$R$^{11}$, —SO$_2$R$^{10}$, —SO$_2$NR$^9$R$^{11}$, —R$^{10}$cycloalkyl, —R$^{10}$OR$^9$, —R$^{10}$NR$^9$R$^{11}$, —R$^{10}$C(O)R$^9$, —R$^{10}$CO$_2$R$^9$, —R$^{10}$C(O)NR$^9$R$^{11}$, —R$^{10}$C(S)NR$^9$R$^{11}$, —R$^{10}$NHC(NH)NR$^9$R$^{11}$, —R$^{10}$C(NH)NR$^9$R$^{11}$, —R$^{10}$SO$_2$R$^{10}$, —R$^{10}$SO$_2$NR$^9$R$^{11}$, —R$^{10}$NHSO$_2$R$^9$, R$^{10}$NHCOR$^9$ and —R$^{10}$SO$_2$NHCOR$^9$;

each $R^9$ and $R^{11}$ are the same or different and are independently selected from the group consisting of H, alkyl, cycloalkyl, —R$^{10}$cycloalkyl, —R$^{10}$OH, —R$_{10}$(OR$^{10}$)$_w$ where w is 1–10, and —R$^{10}$NR$^{10}$R$^{10}$;

each $R^{10}$ is the same or different and is independently selected from the group consisting of alkyl, cycloalkyl, alkenyl, cycloalkenyl and alkynyl;

n is 0, 1 or 2;

Ay is aryl;

Het is a 5- or 6-membered heterocyclic or heteroaryl group;

Y is N;

$R^3$ and $R^4$ are the same or different and are each independently selected from the group consisting of H, halo, alkyl, cycloalkyl, alkenyl, Ay, Het, —$OR^7$, —OAy, —$C(O)R^7$, —C(O)Ay, —$CO_2R^7$, —$CO_2$Ay, —$SO_2NHR^9$, —$NR^7R^8$, —$NR^7$Ay, —NHHet, —$NHR^{10}$Het, —$R^{10}OR^7$, —$R^{10}$OAy, —$R^{10}NR^7R^8$ and —$R^{10}NR^7$Ay;

q is 0, 1, 2, 3, 4 or 5;

each $R^5$ is the same or different and is independently selected from the group consisting of halo, alkyl, cycloalkyl, alkenyl, cycloalkenyl, alkynyl, Ay, Het, —$OR^7$, —OAy, —OHet, —$C(O)R^9$, —$CO_2R^9$, —$C(O)NR^7R^8$, —C(O)Ay, —$C(O)NR^7$Ay, —C(O)Het, —$C(O)NHR^{10}$Het, —$C(S)NR^9R^{11}$, —$C(NH)NR^7R^8$, —$C(NH)NR^7$Ay, —$S(O)_nR^9$, —$S(O)_2NR^7R^8$, —$S(O)_2NR^7$Ay, —$NR^7R^8$, —$NR^7$Ay, —NHHet, —$NHR^{10}$Ay, —$NHR^{10}$Het, —$R^{10}$cycloalkyl, —$R^{10}OR^9$, —$R^{10}NR^7R^8$, —$R^{10}NR^7$Ay, —$R^{10}C(O)R^9$, —$R^{10}CO_2R^9$, —$R^{10}C(O)NR^9R^{11}$, —$R^{10}C(S)NR^9R^{11}$, $R^{10}NHC(NH)NR^9R^{11}$, —$R^{10}C(NH)NR^9R^{11}$, —$R^{10}SO_2R^9$, —$R^{10}SO_2NHCOR^9$, —$R^{10}SO_2NR^9R^{11}$, cyano, nitro and azido; or two adjacent $R^5$ groups together with the atoms to which they are bonded form a $C_{5-6}$ cycloalkyl or aryl;

p is 1, 2 or 3; and each $R^6$ is the same or different and is independently selected from the group consisting of halo, alkyl, cycloalkyl, alkenyl, cycloalkenyl, alkynyl, Ay, Het, —$OR^7$, —OAy, —OHet, —$OR^{10}$Ay, —$OR^{10}$Het, —$C(O)R^9$, —$CO_2R^9$, —$C(O)NR^7R^8$, —C(O)Ay, —$C(O)NR^7$Ay, —$C(O)NHR^{10}$Ay, —C(O)Het, —$C(O)NHR^{10}$Het, —$C(S)NR^9R^{11}$, —$C(NH)NR^7R^8$, —$C(NH)NR^7$Ay, —$S(O)_nR^9$, —$S(O)_n$Ay, —$S(O)_n$Het, —$S(O)_2NR^7R^8$, —$S(O)_2NR^7$Ay, —$NR^7R^8$, —$NR^7$Ay, —$NHR^{10}$Ay, —NHHet, —$NHR^{10}$Het, —$R^{10}$cycloalkyl, —$R^{10}$Ay, —$R^{10}$Het, —$R^{10}OR^9$, —$R^{10}$—O—$C(O)R^9$, —$R^{10}$—O—C(O)Ay, —$R^{10}$—O—C(O)Het, —$R^{10}$—O—$S(O)_nR^9$, —$R^{10}NR^7R^8$, —$R^{10}NR^7$Ay, —$R^{10}C(O)R^9$, —$R^{10}CO_2R^9$, —$R^{10}C(O)NR^9R^{11}$, —$R^{10}C(S)NR^9R^{11}$, —$R^{10}NHC(NH)NR^9R^{11}$, —$R^{10}C(NH)NR^9R^{11}$, —$R^{10}SO_2R^9$, —$R^{10}SO_2NHCOR^9$, —$R^{10}SO_2NR^9R^{11}$, cyano, nitro and azido; or two adjacent $R^6$ groups together with the atoms to which they are bonded form a $C_{5-6}$ cycloalkyl or a 5- or 6-membered heterocyclic group containing 1 or 2 heteroatoms;

wherein at least one $R^6$ is selected from the group consisting of —$NR^7R^8$, —$NR^7$Ay, —NHHet, —$NHR^{10}$Ay and —$NHR^{10}$Het; and or a pharmaceutically acceptable salt thereof.

2. The compound according to claim 1 wherein $R^2$ is selected from the group consisting of Ay, Het, —$OR^7$, —OAy, —OHet, —$OR^{10}$Het —$S(O)_nR^9$, —$S(O)_n$Ay, —$NR^7R^8$, —NHHet, —$NHR^{10}$Het, —$R^{10}NR^7R^8$ and —$R^{10}NR^7$Ay.

3. The compound according to claim 1 wherein $R^2$ is —$NR^7R^8$.

4. The compound according to claim 1 wherein $R^3$ and $R^4$ are the same or different and are each independently selected from the group consisting of H, halo, alkyl, —$OR^7$, —$CO_2R^7$ and—$NR^7R^8$.

5. The compound according to claim 1 -wherein $R^3$ and $R^4$ are each H.

6. The compound according to claim 1 wherein q is 0, 1 or 2.

7. The compound according to claim 1 wherein each $R^5$ is the same or different and is independently selected from the group consisting of halo, alkyl, alkenyl, Ay, Het, —$OR^7$, —$CO_2R^9$, —$C(O)NR^7R^8$, —$S(O)_2NR^7R^8$, —$NR^7R^8$, —$NHR^{10}$Ay, cyano, nitro and azido.

8. The compound according to claim 1, wherein each $R^5$ is the same or different and is independently selected from the group consisting of halo, alkyl, —$OR^7$ and cyano.

9. The compound according to claim 1 wherein p is 1 or 2.

10. The compound according to claim 1 -wherein p is 1.

11. The compound according to claim 1 -wherein p is 1 and $R^6$ is at the C-5 position.

12. The compound according to claim 1 wherein p is 1 and $R^6$ is at the C-6 position.

13. The compound according to claim 1 wherein each $R^6$ is the same or different and is independently selected from the group consisting of halo, alkyl, Ay, Het, —$OR^7$, —OAy, —OHet, —$CO_2R^9$, —$C(O)NR^7R^8$, —$C(O)NR^7$Ay, —$NR^7R^8$, —$NR^7$Ay, —NHHet, —$NHR^{10}$Het, —$NHR^{10}$Ay and cyano.

14. The compound according to claim 1 wherein each $R^6$ is the same or different and is independently selected from the group consisting of halo, —$NR^7R^8$, —$NR^7$Ay, —NHHet, —$NHR^{10}$Het and —$NHR^{10}$Ay.

15. A compound selected from the group consisting of:

N-Cyclopentyl-3-[2-(cyclopentylamino)-4-pyrimidinyl]-2-(4-fluorophenyl)pyrazolo-[1,5-α]pyridin-5-amine;

3-[2-(Cyclopentylamino)-4-pyrimidinyl]-2-(4-fluorophenyl)pyrazolo[1,5-α]pyridin-5-amine;

N-[3-[2-(Cyclopentylamino)-4-pyrimidinyl]-2-(4fluorophenyl)pyrazolo[1,5-α]pyridin-5yl]methanesulfonamide;

3-[2-(cyclopentylamino)-4-pyrimidinyl]-2-(4-fluorophenyl)pyrazolo[1,5-α]pyridin-6-amine;

N-Cyclopentyl;-3-[2-(cyclopentylamino)-4-pyrimidinyl]2-(4-fluorophenyl)pyrazolo[1,5-α]pyridin-6-amine;

3-[2-(Cyclopentylamino)-4-pyrimidinyl]-2-(4-fluorophenyl)-N-isopropylpyrazolo[1,5-α]pyridin-6-amine;

3-[2-(Cyclopentylamino)-4-pyrimidinyl]-2-(4-fluorophenyl)-N-(2-methoxyethyl)pyrazolo[1,5-α]pyridin-5-amine;

3-[2-(Cyclopentylamino)-4-pyrimidinyl]-2-(4-fluorophenyl)-N-isopropylpyrazolo[1,5-α]pyridin-5-amine;

N-Cyclopentyl-3-[2-(cyclopentylamino)-4-pyrimidinyl]-2-(4-methoxyphenyl)-pyrazolo[1,5-α]pyridin-5-amine; and 3-[2-(Cyclopentylamino)-4-pyrimidinyl]-N-isopropyl-2-(4-methoxyphenyl)pyrazolo[1,5-α]pyridin-5-amine;

4-Bromo-N-cyclopentyl-3-[2-(cyclopentylamino)pyrimidin-4-yl]-2-(4-fluorophenyl)pyrazolo[1,5-α]pyridin-5-amine;

4-Chloro-N-cyclopentyl-3-[2-(cyclopentylamino)pyrimidin-4-yl]-2-(4-fluorophenyl)pyrazolo[1,5-α]pyridin-5-amine;

4-Bromo-N-cyclopentyl-3-[2-(cyclopentylamino)pyrimidin-4-yl]-2-(4-methoxyphenyl)pyrazolo[1,5-α]pyridin-5-amine;

4-Chloro-N-cyclopentyl-3-[2-(cyclopentylamino)pyrimidin-4-yl]-2-(4-methoxyphenyl)pyrazolo[1,5-α]pyridin-5-amine;

4-{5-(Cyclopentylamino)-3-[2-(cyclopentylamino)-4-pyrimidinyl]pyrazolo[1,5-α]pyridin-2-yl}phenol;

N-Cyclopentyl-3-[2-(cyclopentylamino)-4-pyrimidinyl]-2-(4-isobutoxyphenyl)pyrazolo[1,5-α]pyridin-5-amine; and N-Cyclopentyl-3-[2-(cyclopentylamino)-4-pyrimidinyl]-2-[4-(cyclopropylmethoxy)phenyl]pyrazolo[1,5-α]pyridin-5-amine, and pharmaceutically acceptable salts thereof.

16. A pharmaceutical composition comprising a compound according to claim 1.

17. The pharmaceutical composition according to claim 16 further comprising a pharmaceutically acceptable carrier or diluent.

18. The pharmaceutical composition according to claim 16 further comprising an antiviral agent selected from the group consisting of aciclovir and valaciclovir.

19. A method for the treatment of a herpes viral infection selected from HSV-1 and HSV-2 in an animal, said method comprising administering to the animal a therapeutically effective amount of a compound according to claim 1.

20. A method for treatment of a condition or disease associated with a herpes viral infection selected from HSV-1 and HSV-2 in an animal, comprising administering to the animal a therapeutically effective amount of the compound of formula (I) according to claim 1.

21. A process for preparing a compound according to claim 1 wherein $R^2$ is selected from the group consisting of alkyl, cycloalkyl, alkenyl, cycloalkenyl, Ay, Het, —$OR^7$, —OAy, —OHet, —$OR^{10}$Het —$S(O)_nR^9$, —$S(O)_n$Ay, —$S(O)_n$Het, —$S(O)_nNR^7R^8$, —$NR^7R^8$, —NHHet, —$NHR^{10}$Het, —$NHR^{10}$Ay, —$R^{10}NR^7R^8$ and —$R^{10}NR^7$Ay; and $R^3$ and $R^4$ are H, said process comprising reacting a compound of formula (IX):

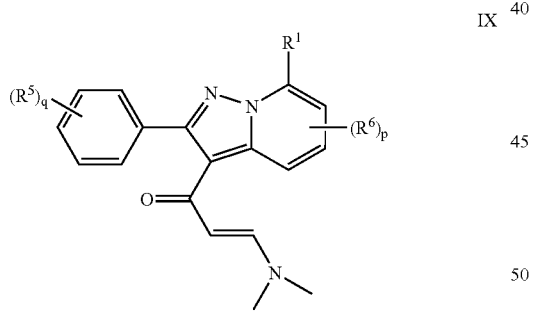

IX wherein at least one $R^6$ is selected from the group consisting of —$NR^7R^8$, —$NR^7$Ay, —NHHet, —$NHR^{10}$Ay and —$NHR^{10}$Het;

with an amine of formula (X):

X

22. A process for preparing a compound according to claim 1, said process comprising the steps of:

(a) reacting the compound of formula (XXXII)

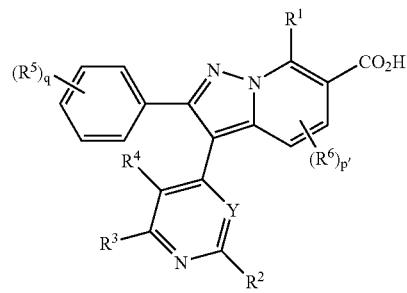

XXXII wherein p' is 0, 1 or 2;
with diphenylphosphoryl azide in tert-butanol to give the compound of formula (I-X)

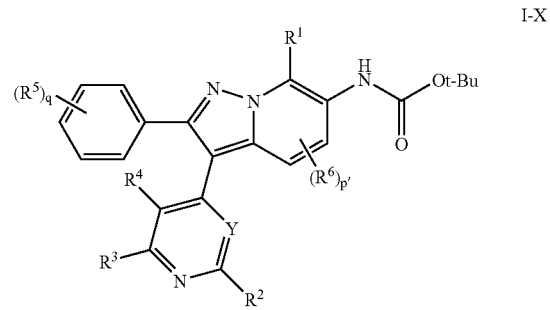

I-X (b) optionally cleaving the compound of formula (I-X) to give the compound of formula (I-Y)

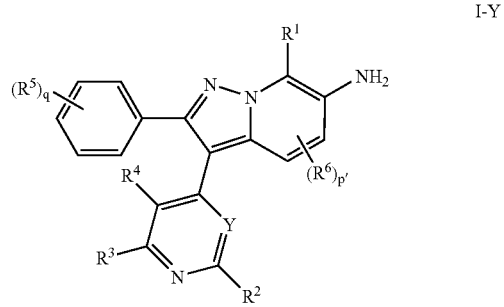

I-Y and (c) optionally converting the compound of formula (I-Y) to a compound of formula (I-Z)

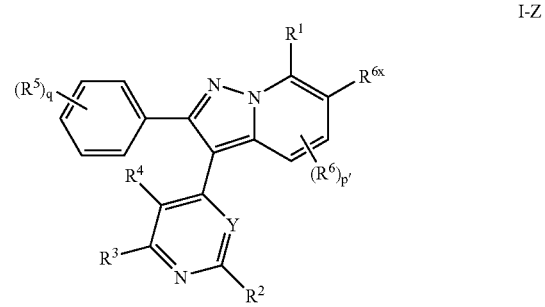

I-Z wherein $R^{6x}$ is selected from the group consisting of —$NR^7R^8$ where $R^7$ and $R^8$ are not both H, —$NR^7Ay$, —NHHet, —$NHR^{10}Ay$ and —$NHR^{10}$Het; using conditions selected from the group consisting of cross coupling, reductive amination, alkylation, acylation and sulfonylation.

23. A process for preparing a compound according to claim 1 wherein $R^2$ is selected from the group consisting of alkyl, cycloalkyl, alkenyl, cycloalkenyl, Ay, Het, —$OR^7$, —OAy, —OHet, —$OR^{10}$Het —$S(O)_nR^9$, —$S(O)_nAy$, —$S(O)_n$Het, —$S(O)_nNR^7R^8$, —$NR^7R^8$, —NHHet, —$NHR^{10}$Het, —$NHR^{10}$Ay, —$R^{10}NR^7R^8$ and —$R^{10}NR^7Ay$; $R^3$ is selected from the group consisting of H, alkyl, cycloalkyl, alkenyl, Ay, Het, —$C(O)R^7$, —C(O)Ay, —$CO_2R^7$, —$CO_2Ay$, —$SO_2NHR^9$, —$NR^7R^8$ (where $R^7$ and $R^8$ are not H), —$NR^7Ay$ (where $R^7$ is not H), —$R^{100}R^7$, —$R^{10}OAy$, —$R^{10}NR^7R^8$ and —$R^{10}NR^7Ay$; $R^4$ is H; and at least one $R^6$ is selected from the group consisting of —$NR^7R^8$, —$NR^7Ay$, —NHHet, —$NHR^{10}Ay$ and —$NHR^{10}$Het, said process comprising the steps of:

a) reacting a compound of formula (XVI):

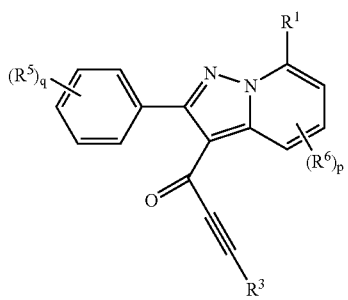

XVI wherein each $R^6$ is the same or different and is independently selected from the group consisting of halo, alkyl, cycloalkyl, alkenyl, cycloalkenyl, alkynyl, Ay, Het, —$OR^7$, —OAy, —OHet, —$OR^{10}Ay$, —$OR^{10}$Het, —$C(O)R^9$, —$CO_2R^9$, —$C(O)NR^7R^8$, —C(O)Ay, —$C(O)NR^7Ay$, —$C(O)NHR^{10}Ay$, —C(O)Het, —$C(O)NHR^{10}$Het, —$C(S)NR^9R^{11}$, —$C(NH)NR^7R^8$, —$C(NH)NR^7Ay$, —$S(O)_nR^9$, —$S(O)_nAy$, —$S(O)_n$Het, —$S(O)_2NR^7R^8$, —$S(O)_2NR^7Ay$, —$NR^7R^8$, —$NR^7Ay$, —$NHR^{10}Ay$, —NHHet, —$NHR^{10}$Het, —$R^{10}$cycloalkyl, —$R^{10}Ay$, —$R^{10}$Het, —$R^{10}OR^9$, —$R^{10}$—O—$C(O)R^9$, —$R^{10}$—O—C(O)Ay, —$R^{10}$—O—C(O)Het, —$R^{10}$—O—$S(O)_nR^9$, —$R^{10}NR^7R^8$, —$R^{10}NR^7Ay$, —$R^{10}C(O)R^9$, —$R^{10}CO_2R^9$, —$R^{10}C(O)NR^9R^{11}$, —$R^{10}C(S)NR^9R^{11}$, —$R^{10}NHC(NH)NR^9R^{11}$, —$R^{10}C(NH)NR^9R^{11}$, —$R^{10}SO_2R^9$, —$R^{10}SO_2NHCOR^9$, —$R^{10}SO_2NR^9R^{11}$, cyano, nitro and azido; or two adjacent $R^6$ groups together with the atoms to which they are bonded form a $C_{5-6}$ cycloalkyl or a 5- or 6-membered heterocyclic group containing 1 or 2 heteroatoms;

wherein at least one $R^6$ is selected from the group consisting of halo, —$NR^7R^8$, —$NR^7Ay$, —NHHet, —$NHR^{10}Ay$ and —$NHR^{10}$Het;

with an amine of formula (X):

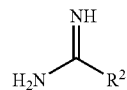

X to prepare a compound of formula (XVII):

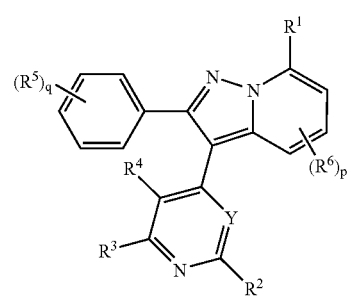

XVII wherein at least one $R^6$ is selected from the group consisting of halo, —$NR^7R^8$, —$NR^7Ay$, —NHHet, —$NHR^{10}Ay$ and —$NHR^{10}$Het; and b) in the embodiment wherein no $R^6$ is —$NR^7R^8$, —$NR^7Ay$, —NHHet, —$NHR^{10}Ay$ or —$NHR^{10}$Het, replacing $R^6$ halo of the compound of formula (XVII) with an amine substituent selected from the group consisting of —$NR^7R^8$, —$NR^7Ay$, —NHHet, —$NHR^{10}Ay$ and-$NHR^{10}$Het;

to prepare a compound of formula (I).

24. A process for preparing a compound according to claim 1 wherein $R^2$ is selected from the group consisting of alkyl, cycloalkyl, alkenyl, cycloalkenyl, Ay, Het, —$OR^7$, —OAy, —OHet, —$OR^{10}$Het —$S(O)_nR^9$, —$S(O)_nAy$, —$S(O)_n$Het, —$S(O)_nNR^7R^8$, —$NR^7R^8$, —NHHet, —$NHR^{10}$Het, —$NHR^{10}Ay$, —$R^{10}NR^7R^8$ and —$R^{10}NR^7Ay$; and at least one $R^6$ is selected from the group consisting of —$NR^7R^8$, —$NR^7Ay$, —NHHet, —$NHR^{10}Ay$ and —$NHR^{10}$Het, said process comprising the steps of:

a) reacting a compound of formula (XX):

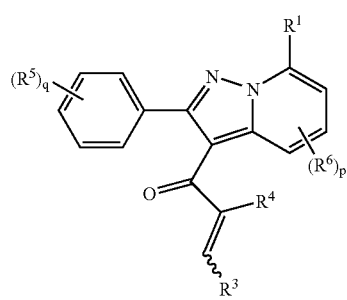

XX wherein each $R^6$ is the same or different and is independently selected from the group consisting of halo, alkyl, cycloalkyl, alkenyl, cycloalkenyl, alkynyl, Ay, Het, —$OR^7$, —OAy, —OHet, —$OR^{10}Ay$, —$OR^{10}$Het, —$C(O)R^9$, —$CO_2R^9$, —$C(O)NR^7R^8$, —C(O)Ay, —$C(O)NR^7Ay$, —$C(O)NHR^{10}Ay$, —C(O)Het, —$C(O)NHR^{10}$Het, —$C(S)NR^9R^{11}$, —$C(NH)NR^7R^8$, —$C(NH)NR^7Ay$, —$S(O)_nR^9$, —$S(O)_nAy$, —$S(O)_n$Het, —$S(O)_2NR^7R^8$, —$S(O)_2NR^7Ay$, —$NR^7R^8$, —$NR^7Ay$, —$NHR^{10}Ay$, —NHHet, —$NHR^{10}$Het, —$R^{10}$cycloalkyl, —$R^{10}Ay$, —$R^{10}$Het, —$R^{10}OR^9$, —$R^{10}$—O—$C(O)R^9$, —$R^{10}$—O—C(O)Ay, —$R^{10}$—O—C(O)Het, —R¹⁰—O—S(O)ₙR⁹, —R¹⁰NR⁷R⁸, —R¹⁰NR⁷Ay, —R¹⁰C(O)R⁹, —R¹⁰CO₂R⁹, —R¹⁰C(O)NR⁹R¹¹, —R¹⁰C(S)NR⁹R¹¹, —R¹⁰NHC(NH)NR⁹R¹¹, —R¹⁰C(NH)NR⁹R¹¹, —R¹⁰SO₂R⁹, —R¹⁰SO₂NHCOR⁹, —R¹⁰SO₂NR⁹R¹¹, cyano, nitro and azido; or two adjacent R⁶ groups together with the atoms to which they are bonded form a C₅₋₆cycloalkyl or a 5- or 6-membered heterocyclic group containing 1 or 2 heteroatoms;

wherein at least one R⁶ is selected from the group consisting of halo, —NR⁷R⁸, —NR⁷Ay, —NHHet, —NHR¹⁰Ay and —NHR¹⁰Het;

with an amine of formula (X):

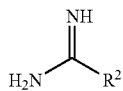

X to prepare an intermediate compound;

b) oxidizing the intermediate compound to prepare a compound of formula (XVII):

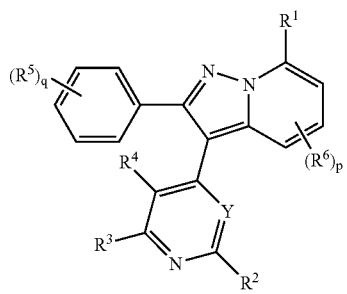

XVII wherein at least one R⁶ is selected from the group consisting of halo, —NR⁷R⁸, —NR⁷Ay, —NHHet, —NHR¹⁰Ay and —NHR¹⁰Het; and c) in the embodiment wherein no R⁶ is —NR⁷R⁸, —NR⁷Ay, —NHHet, —NHR¹⁰Ay or —NHR¹⁰Het, replacing R⁶ halo of the compound of formula (XVII) with an amine substituent selected from the group consisting of —NR⁷R⁸, —NR⁷Ay, —NHHet, —NHR¹⁰Ay and—NHR¹⁰Het; to prepare a compound of formula (I).

25. A process for preparing a compound according to claim 1 wherein at least one R⁶ is selected from the group consisting of —NR⁷R⁸, —NR⁷Ay, —NHHet, —NHR¹⁰Ay and —NHR¹⁰Het, said process comprising the steps of:

a) reacting a compound of formula (XXII):

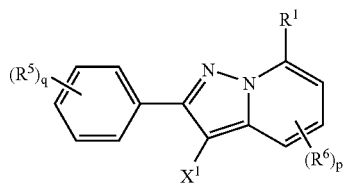

XXII wherein each R⁶ is the same or different and is independently selected from the group consisting of halo, alkyl, cycloalkyl, alkenyl, cycloalkenyl, alkynyl, Ay, Het, —OR⁷, —OAy, —OHet, —OR¹⁰Ay, —OR¹⁰Het, —C(O)R⁹, —CO₂R⁹, —C(O)NR⁷R⁸, —C(O)Ay, —C(O)NR⁷Ay, —C(O)NHR¹⁰Ay, —C(O)Het, —C(O)NHR¹⁰Het, —C(S)NR⁹R¹¹, —C(NH)NR⁷R⁸, —C(NH)NR⁷Ay, —S(O)ₙR⁹, —S(O)ₙAy, —S(O)ₙHet, —S(O)₂NR⁷R⁸, —S(O)₂NR⁷Ay, —NR⁷R⁸, —NR⁷Ay, —NHR¹⁰Ay, —NH-Het, —NHR¹⁰Het, —R¹⁰cycloalkyl, —R¹⁰Ay, —R¹⁰Het, —R¹⁰OR⁹, —R¹⁰—O—C(O)R⁹, —R¹⁰—O—C(O)Ay, —R¹⁰—O—C(O)Het, —R¹⁰—O—S(O)ₙR⁹, —R¹⁰NR⁷R⁸, —R¹⁰NR⁷Ay, —R¹⁰C(O)R⁹, —R¹⁰CO₂R⁹, —R¹⁰C(O)NR⁹R¹¹, —R¹⁰C(S)NR⁹R¹¹, —R¹⁰NHC(NH)NR⁹R¹¹, —R¹⁰C(NH)NR⁹R¹¹, —R¹⁰SO₂R⁹, —R¹⁰SO₂NHCOR⁹, —R¹⁰SO₂NR⁹R¹¹, cyano, nitro and azido; or two adjacent R⁶ groups together with the atoms to which they are bonded form a C₅₋₆cycloalkyl or a 5- or 6-membered heterocyclic group containing 1 or 2 heteroatoms;

wherein at least one R⁶ is selected from the group consisting of halo, —NR⁷R⁸, —NR⁷Ay, —NHHet, —NHR¹⁰Ay and —NHR¹⁰Het; and X¹ is chloro, bromo or iodo;

with a compound of formula (XXIV):

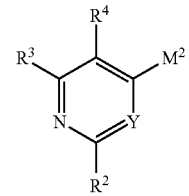

XXIV wherein M² is selected from the group consisting of —B(OH)₂, —B(ORa)₂, —B(Ra)₂, —Sn(Ra)₃, Zn-halide, ZnRa, and Mg-halide where Ra is alkyl or cycloalkyl and halide is halo;

to prepare a compound of formula (XVII):

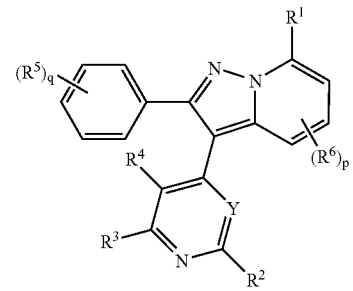

XVII wherein at least one R⁶ is selected from the group consisting of halo, —NR⁷R⁸, —NR⁷Ay, —NHHet, —NHR¹⁰Ay and —NHR¹⁰Het; and b) in the embodiment wherein no R⁶ is —NR⁷R⁸, —NR⁷Ay, —NHHet, —NHR¹⁰Ay or —NHR¹⁰Het, replacing R⁶ halo of the compound of formula (XVII) with an amine substituent selected from the group consisting of —NR⁷R⁸, —NR⁷Ay, —NHHet, —NHR¹⁰Ay and—NHR¹⁰Het;

to prepare a compound of formula (I).

* * * * *

UNITED STATES PATENT AND TRADEMARK OFFICE
CERTIFICATE OF CORRECTION

PATENT NO. : 7,141,569 B2
APPLICATION NO. : 10/473491
DATED : November 28, 2006
INVENTOR(S) : Cheung et al.

It is certified that error appears in the above-identified patent and that said Letters Patent is hereby corrected as shown below:

Column 108, line 57
Should read:
-- $-R^{10}SO_2NR^9R^{11}$, $-R^{10}NHSO_2R^9$, $-R^{10}NHCOR^9$. --

Column 110, Line 33
Should read:
-- N-[3-[2-(Cyclopentylamino)-4-pyrimidinyl]-2-(4-fluo- --

Column 110, Line 38
Should read:
-- N-Cyclopentyl-3-[2-(cyclopentylamino)-4-pyrimidinyl] --

Column 113, Line 14
Should read:
-- $R^8$ are not H), $-NR^7Ay$ (where $R^7$ is not H), $-R^{10}R^7$, --

Signed and Sealed this

Tenth Day of April, 2007

JON W. DUDAS
*Director of the United States Patent and Trademark Office*